(12) United States Patent
Kobayashi et al.

(10) Patent No.: US 10,359,060 B2
(45) Date of Patent: Jul. 23, 2019

(54) MOVING DEVICE AND MOVING METHOD OF MOVING DEVICE

(71) Applicants: OLYMPUS CORPORATION, Tokyo (JP); NPO INTERNATIONAL RESCUE SYSTEM INSTITUTE, Hyogo (JP); TOHOKU UNIVERSITY, Miyagi (JP)

(72) Inventors: Eiichi Kobayashi, Tama (JP); Yasuo Hirata, Hachioji (JP); Satoshi Tadokoro, Sendai (JP); Tomonari Yamamoto, Sendai (JP); Masashi Konyo, Sendai (JP); Kenjiro Tadakuma, Sendai (JP)

(73) Assignees: Olympus Corporation, Tokyo (JP); NIPO International Rescue System Institute, Hyogo (JP); Tohoku University, Miyagi (JP)

(*) Notice: Subject to any disclaimer, the term of this patent is extended or adjusted under 35 U.S.C. 154(b) by 195 days.

(21) Appl. No.: 15/686,941

(22) Filed: Aug. 25, 2017

(65) Prior Publication Data
US 2017/0350424 A1    Dec. 7, 2017

Related U.S. Application Data

(63) Continuation of application No. PCT/JP2016/054238, filed on Feb. 15, 2016.

(30) Foreign Application Priority Data

Feb. 27, 2015 (JP) ................................ 2015-039324

(51) Int. Cl.
*F15B 15/10* (2006.01)
*G02B 23/24* (2006.01)
(Continued)

(52) U.S. Cl.
CPC ........ *F15B 15/106* (2013.01); *A61B 1/00133* (2013.01); *F15B 15/06* (2013.01);
(Continued)

(58) Field of Classification Search
CPC ............ A61B 1/00133; A61B 1/00147; A61B 1/00154; F15B 15/106
See application file for complete search history.

(56) References Cited

U.S. PATENT DOCUMENTS 5,144,848 A    9/1992    Uenishi et al.
5,428,961 A    7/1995    Sakakibara et al.
(Continued)

FOREIGN PATENT DOCUMENTS

DE      10006769 A1 * 9/2001    ............. F15B 15/10
JP      H03-249721 A    11/1991
(Continued)

OTHER PUBLICATIONS

International Search Report dated Apr. 26, 2016 received in PCT/JP2016/054238.

*Primary Examiner* — Michael Leslie
*Assistant Examiner* — Matthew Wiblin
(74) *Attorney, Agent, or Firm* — Scully, Scott, Murphy & Presser, P.C.

(57) ABSTRACT

A moving device includes an elastic tube, a sectional shape of which is elastically deformable according to an internal pressure given by fluid, a slider unit capable of moving forward and backward in a longitudinal direction of the elastic tube according to a change in the sectional shape of the elastic tube, a brake provided in the slider unit and configured to be deformed in a direction perpendicular to the longitudinal direction of the elastic tube to be capable of coming into sliding contact with a target object, and a fluid adjusting section configured to supply air to or discharge air (Continued)

from the elastic tube respectively via first and second fluid supply pipes that respectively communicate with insides on a distal end side and a proximal end side of the elastic tube.

24 Claims, 47 Drawing Sheets

(51) Int. Cl.
  *F15B 15/06* (2006.01)
  *F16D 51/06* (2006.01)
  *F16D 63/00* (2006.01)
  *F16D 65/22* (2006.01)
  *A61B 1/00* (2006.01)
  *F16D 121/08* (2012.01)
  *F16D 125/14* (2012.01)
  *F16D 125/58* (2012.01)

(52) U.S. Cl.
  CPC ........... *F16D 51/06* (2013.01); *F16D 63/008* (2013.01); *F16D 65/22* (2013.01); *G02B 23/24* (2013.01); *F16D 2121/08* (2013.01); *F16D 2125/14* (2013.01); *F16D 2125/585* (2013.01); *G02B 23/2476* (2013.01)

(56) References Cited

U.S. PATENT DOCUMENTS

| | | | |
|---|---|---|---|
| 2007/0049797 A1* | 3/2007 | Yoshida | A61B 1/00082 600/117 |
| 2007/0163597 A1* | 7/2007 | Mikkaichi | A61B 1/273 128/207.15 |
| 2008/0033246 A1* | 2/2008 | Matsui | A61B 1/00082 600/115 |
| 2008/0115606 A1 | 5/2008 | Suzuki | |
| 2011/0112410 A1* | 5/2011 | Hirota | A61B 5/0066 600/478 |
| 2011/0245616 A1* | 10/2011 | Kobayashi | A61B 1/0653 600/178 |
| 2012/0029283 A1* | 2/2012 | Yamakawa | A61B 1/00154 600/114 |

FOREIGN PATENT DOCUMENTS

| | | | |
|---|---|---|---|
| JP | H04-002565 A | 1/1992 | |
| JP | H06-046539 A | 2/1994 | |
| JP | 2008-022952 A | 2/2008 | |
| JP | 2010-155034 A | 7/2010 | |
| JP | 2011-156228 A | 8/2011 | |
| JP | 2014-228658 A | 12/2014 | |
| WO | WO-2010035296 A1 * | 4/2010 | ............ F15B 15/10 |

* cited by examiner

MOVING DEVICE AND MOVING METHOD OF MOVING DEVICE

CROSS REFERENCE TO RELATED APPLICATION

This application is a continuation application of PCT/JP2016/054238 filed on Feb. 15, 2016 and claims benefit of Japanese Application No. 2015-039324 filed in Japan on Feb. 27, 2015, the entire contents of which are incorporated herein by this reference.

BACKGROUND OF THE INVENTION

1. Field of the Invention

The present invention relates to a moving device that moves in a narrow space formed by wall sections having a narrow interval such as insides of various pipes, a space between flanges of H steel, a space between rips of I steel or channel steel, or an inside of debris and a moving method of the moving device.

2. Description of the Related Art

There has been proposed and put to practice use various moving devices for moving in narrow spaces for the purpose of performing inspection and maintenance of insides of various buildings and machines, searches at the time of disasters, or the like.

For example, Japanese Patent Application Laid-Open Publication No. H6-46539 discloses a self-propelled mechanism (a moving device) including a machine main body configured from a stretchable front main body and a stretchable rear main body, a plurality of stretchable front driving legs protruded on an outer circumferential surface of the front main body, and a plurality of stretchable rear driving legs protruded on an outer circumferential surface of the rear main body. In forward movement, first, the self-propelled mechanism is controlled to be in a state in which the front main body and the rear main body contract to each other and the front driving legs and the rear driving legs project to come into pressed contact with a pipe inner wall. The self-propelled mechanism contracts the front driving legs, further extends the front main body forward, thereafter extends the front driving legs to bring the front driving legs into pressed contact with the pipe inner wall, and, further, in a state in which the rear driving legs are contracted, contracts the rear main body to the front main body side to be capable of moving forward.

SUMMARY OF THE INVENTION

A moving device according to an aspect of the present invention includes: an elastic tube, a sectional shape of which is elastically deformable according to an internal pressure given by fluid; a slider unit capable of moving forward and backward in a longitudinal direction of the elastic tube according to a change in the sectional shape of the elastic tube; a brake provided in the slider unit and configured to be deformed in a direction perpendicular to the longitudinal direction of the elastic tube to be capable of coming into sliding contact with a target object; a first fluid supply pipe configured to communicate with an inside on a distal end side of the elastic tube; a second fluid supply pipe configured to communicate with an inside on a proximal end side of the elastic tube; and a fluid adjusting section configured to supply the fluid to or discharge the fluid from the elastic tube respectively via the first fluid supply pipe and a second fluid supply pipe.

A moving method of a moving device according to an aspect of the present invention includes: a slider-unit moving procedure for controlling, unequally on a distal end side and a proximal end side of an elastic tube, a pressure of fluid supplied to or discharged from the elastic tube via at least either one of a first fluid supply pipe that communicates with an inside on the distal end side of the elastic tube, a sectional shape of which is elastically deformable according to an internal pressure, and a second fluid supply pipe that communicates with an inside on the proximal end side of the elastic tube and relatively moving, in a desired moving direction, a slider unit capable of moving forward and backward in a longitudinal direction of the elastic tube according to a change in the sectional shape of the elastic tube; a brake actuating procedure for deforming a brake provided in the slider unit in a radial direction and bringing the brake into sliding contact with a target object; an elastic-tube moving procedure for controlling, unequally on the distal end side and the proximal end side of the elastic tube, the pressure of the fluid supplied to or discharged from the elastic tube via at least either one of the first fluid supply pipe and the second fluid supply pipe and relatively moving the elastic tube in the moving direction with respect to the slider unit; and a brake releasing procedure for releasing the sliding contact of the brake with the target object.

DETAILED DESCRIPTION OF THE PREFERRED EMBODIMENTS

Figure 1:
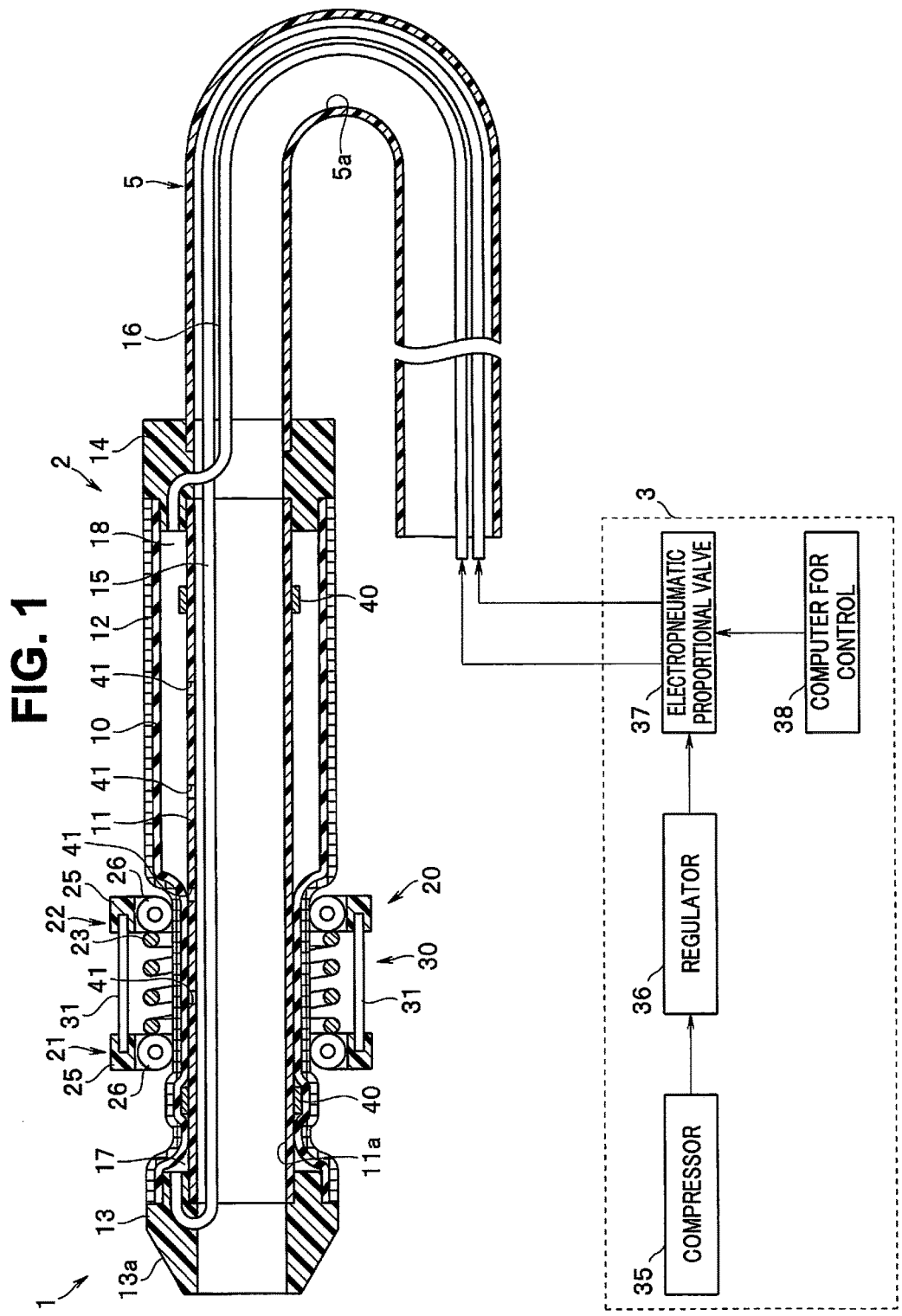
FIG. 1 relates to a first embodiment and is a schematic configuration diagram of a moving device.
Figure 2:
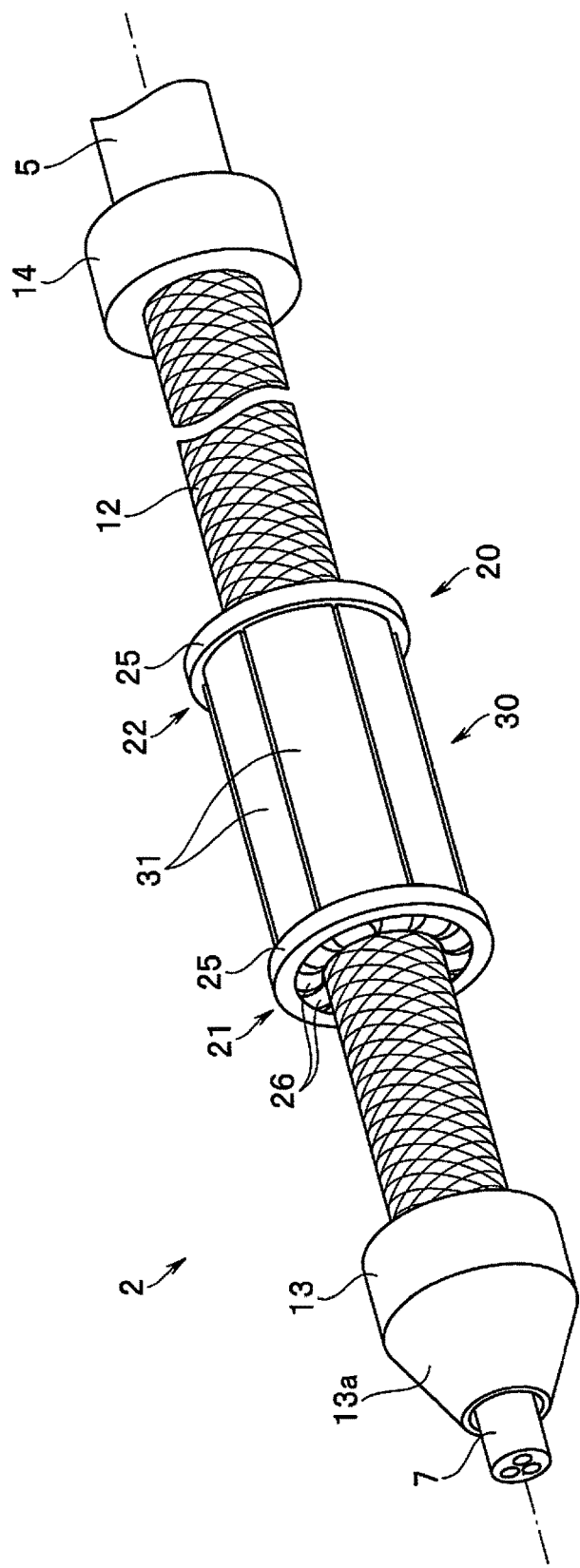
FIG. 2 relates to the first embodiment and is a perspective view of a driving unit.
Figure 3:
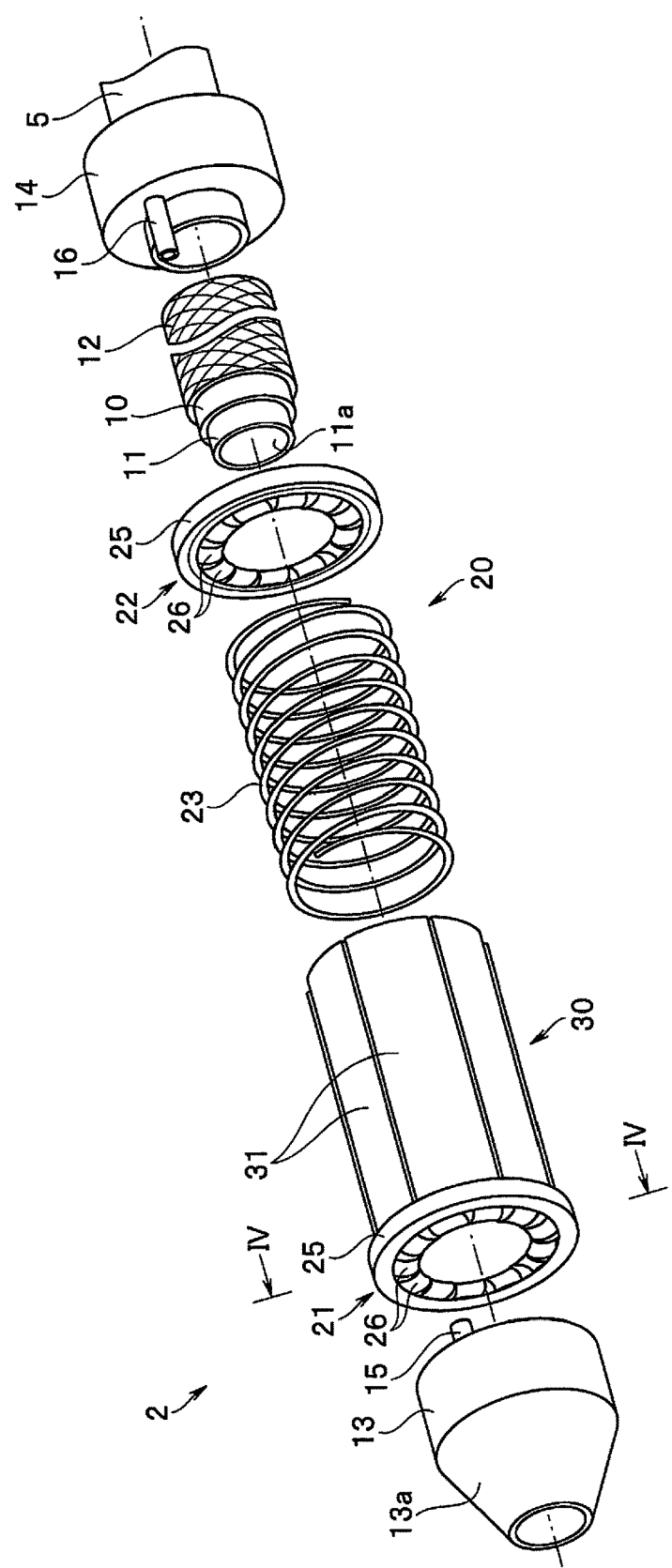
FIG. 3 relates to the first embodiment and is an exploded perspective view of the driving unit.
Figure 4:
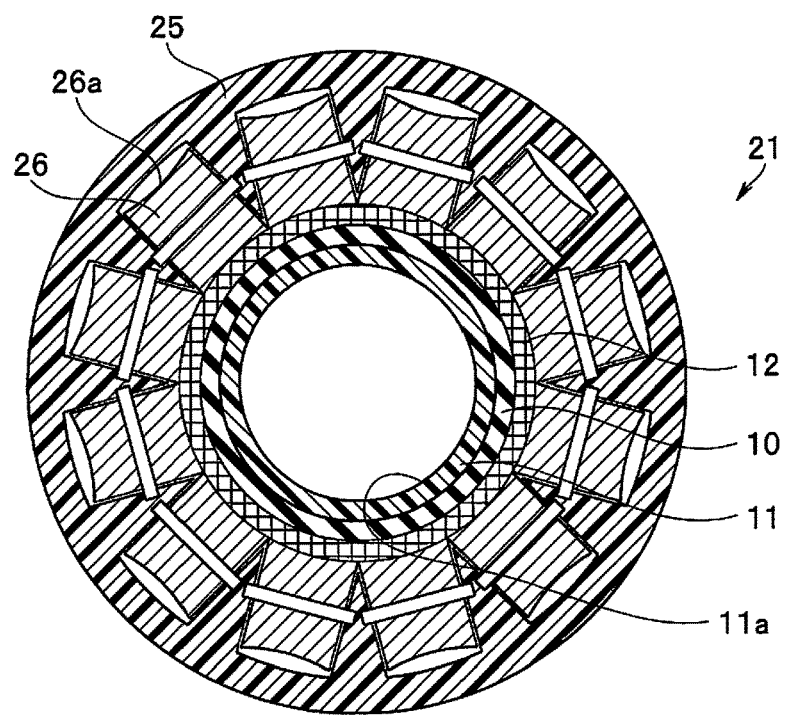
FIG. 4 relates to the first embodiment and is a main part sectional view taken along a IV-IV line of FIG. 3.
Figure 5:
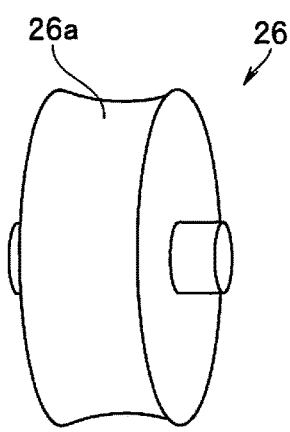
FIG. 5 relates to the first embodiment and is a perspective view of a roller.

Embodiments of the present invention are explained below with reference to the drawings. The drawings relate to a first embodiment of the present invention. FIG. 1 is a schematic configuration diagram of a moving device. FIG. 2 is a perspective view of a driving unit. FIG. 3 is an exploded perspective view of the driving unit. FIG. 4 is a main part sectional view taken along a IV-IV line of FIG. 3. FIG. 5 is a perspective view of a roller. FIGS. 6 to 9 are operation explanatory diagrams of the driving unit.

A moving device 1 of the present embodiment shown in FIG. 1 is applied to a guide tube 5 for guiding an endoscope 7 (see FIG. 2) into a pipe 50 (see FIGS. 6 to 9) provided in a building or the like. The moving device 1 includes a driving unit 2 provided at a distal end of the guide tube 5 and a fluid adjusting section 3 capable of supplying air serving as fluid to the driving unit 2 or discharging the air from the driving unit 2. The guide tube 5 is configured mainly from a long tube having flexibility formed of polyurethane or the like. An inside of the guide tube 5 is set as a channel 5a through which the endoscope 7 or the like can be inserted.

As shown in FIGS. 1 to 3, the driving unit 2 includes an elastic tube 10, a sectional shape of which is elastically deformable (expandable and contractible) according to an internal pressure given by the fluid supplied from the fluid adjusting section 3, a slider unit 20 capable of moving forward and backward in a longitudinal direction on the elastic tube 10 according to a change in the sectional shape of the elastic tube 10, and a brake 30 provided in the slider unit 20.

The elastic tube 10 is configured by an elastic member such as a rubber tube. A flexible tube 11 is inserted through an inner surface side of the elastic tube 10. An outer surface side of the elastic tube 10 is covered with a mesh tube 12.

The flexible tube 11 is configured by a tube made of, for example, polyurethane having rigidity undeformable against an internal pressure of the elastic tube 10. An outer diameter of the flexible tube 11 is formed equal to an inner diameter of the elastic tube 10 or slightly larger than the inner diameter of the elastic tube 10. Consequently, an inner circumferential surface of the elastic tube 10 in a natural state is set in surface contact with an outer circumferential surface of the flexible tube 11. The flexible tube 11 has predetermined flexibility and is capable of supporting the elastic tube 10. An inner diameter of the flexible tube 11 is formed equal to an inner diameter of the guide tube 5. Consequently, an inside of the flexible tube 11 is set as a series channel 11a of the guide tube 5 and the channel 5a.

The mesh tube 12 is configured by a tube in which, for example, unstretchable PET (polyethylene terephthalate) fiber is woven in a mesh shape. The mesh tube 12 is deformable in an outer diameter direction with a limit set to a range in which the mesh is deformable. Consequently, the mesh tube 12 allows the elastic tube 10 to expand at a substantially uniform predetermined outer diameter in the longitudinal direction while preventing the elastic tube 10 from locally expanding.

A distal-end-side end part member 13 formed in a ring shape is provided on distal end sides of the elastic tube 10, the flexible tube 11, and the mesh tube 12. The distal end side of the flexible tube 11 is bonded and fixed to an inner circumference side of the distal-end-side end part member 13. The distal end sides of the elastic tube 10 and the mesh tube 12 are bonded and fixed to an outer circumference side of the distal-end-side end part member 13. The distal end side of the elastic tube 10 is coupled to the distal end side of the flexible tube 11 in an airtight state by the bonding to the distal-end-side end part member 13.

A distal end side of a first fluid supply pipe 15 capable of circulating the air serving as the fluid is retained in the distal-end-side end part member 13. A distal end opening section of the first fluid supply pipe 15 is caused to communicate with an inside on the distal end side of the elastic tube 10 (more specifically, a space between the inner circumferential surface of the elastic tube 10 and the outer circumferential surface of the flexible tube 11).

Note that, in order to improve insertability into the pipe 50 and the like, a taper surface 13a formed in a taper shape is formed on an outer circumferential surface of the distal-end-side end part member 13.

Similarly, a proximal-end-side end part member 14 formed in a ring shape is provided on proximal end sides of the elastic tube 10, the flexible tube 11, and the mesh tube 12. The proximal end side of the flexible tube 11 is bonded and fixed to an inner circumference side of the proximal-end-side end part member 14. The proximal end sides of the elastic tube 10 and the mesh tube 12 are bonded and fixed to an outer circumference side of the proximal-end-side end part member 14. The proximal end side of the elastic tube 10 is coupled to the proximal end side of the flexible tube 11 in an airtight state by the bonding to the proximal-end-side end part member 14.

A distal end side of a second fluid supply pipe 16 capable of circulating the air serving as the fluid is retained in the proximal-end-side end part member 14. A distal end opening section of the second fluid supply pipe 16 is caused to communicate with an inside on the proximal end side of the elastic tube 10 (more specifically, a space between the inner circumferential surface of the elastic tube 10 and the outer circumferential surface of the flexible tube 11).

Further, a distal end side of the guide tube 5 is bonded and fixed to the inner circumference side of the proximal-end-side end part member 14. Note that, in the present embodiment, a configuration is illustrated in which the guide tube 5 and the flexible tube 11 are coupled via the proximal-end-side end part member 14. However, the guide tube 5 and the flexible tube 11 can also be configured by an integral tube.

The slider unit 20 includes a first slider 21 attached to an outer circumference side of the elastic tube 10 via the mesh tube 12, a second slider 22 attached to the outer circumference side of the elastic tube 10 via the mesh tube 12 further on the proximal end side than the first slider 21, and a coil spring 23 functioning as an urging member configured to urge the first and second sliders 21 and 22 in separating directions.

As shown in FIGS. 1 and 4, the respective sliders 21 and 22 include slider main bodies 25 formed in a ring shape and pluralities of rollers 26 axially supported by the slider main bodies 25.

As shown in FIGS. 4 and 5, the respective rollers 26 include rolling surfaces 26a, a sectional shape of which is formed in a partially arcuate shape. The respective rollers 26 are axially supported in a state in which the rollers 26 are annularly arrayed on an inner circumference side of the slider main bodies 25. Series of pressing surfaces formed in an annular shape are formed in inner circumferences of the respective sliders 21 and 22 by the rolling surfaces 26a of the respective rollers 26.

The first slider 21 is capable of moving while pressing, with the pressing surface formed in this way, the inner circumferential surface of the elastic tube 10 against the outer circumferential surface of the flexible tube 11 via the mesh tube 12. Consequently, deformation of a sectional shape of the elastic tube 10 is partially restricted in any position corresponding to a moving state of the first slider 21. A first pressure chamber 17 communicating with the first fluid supply pipe 15 is formed further on the distal end side than the first slider 21.

Similarly, the second slider 22 is capable of moving while pressing the inner circumferential surface of the elastic tube 10 against the outer circumferential surface of the flexible tube 11 via the mesh tube 12. Consequently, deformation of the sectional shape of the elastic tube 10 is partially restricted in any position corresponding to a moving state of the second slider 22. A second pressure chamber 18 communicating with the second fluid supply pipe 16 is formed further on the proximal end side than the second slider 22.

The coil spring 23 is interposed on an outer circumference side of the mesh tube 12 (i.e., the outer circumference side of the elastic tube 10) between the first slider 21 and the second slider 22.

The brake 30 includes a plurality of brake belts 31 functioning as brake members configured by thick belts or the like. As shown in FIGS. 2 and 3, the respective brake belts 31 are annularly arrayed on an outer circumference side of the coil spring 23 and suspended between slider main bodies 25, 25 of the first and second sliders 21 and 22. Consequently, the respective brake belts 31 are capable of bending to project in a bow shape in a radial direction of the elastic tube 10 when a relative interval between the first slider 21 and the second slider 22 is narrowed against an urging force of the coil spring 23. On the other hand, the respective brake belts 31 are capable of expanding to linearly retract along a longitudinal direction of the elastic tube 10 when the relative interval between the first slider 21 and the second slider 22 is widened by the urging force of the coil spring 23.

As shown in FIG. 1, the fluid adjusting section 3 includes a compressor 35 for compressing air serving as working fluid, a regulator 36 for adjusting an air pressure of the air compressed by the compressor 35 to a reference pressure set in advance, an electropneumatic proportional valve 37 for adjusting the air pressure of the air adjusted to the reference pressure by the regulator 36 to any control pressure P, and a computer for control 38 for performing driving control of the electropneumatic proportional valve 37.

In the present embodiment, the first fluid supply pipe 15 and the second fluid supply pipe 16 are connected to the electropneumatic proportional valve 37. The electropneumatic proportional valve 37 is capable of supplying the air adjusted to individual control pressures P respectively to the first and second pressure chambers 17 and 18 via the first and second fluid supply pipes 15 and 16.

In this case, the electropneumatic proportional valve 37 is capable of adjusting, for example, as the control pressures P of the air supplied to the first and second pressure chambers 17 and 18, a first control pressure P1 and a second control pressure P2 higher than the first control pressure P1 by a predetermined pressure.

The electropneumatic proportional valve 37 is capable of discharging the air supplied to the first and second pressure chambers 17 and 18 by individually opening the first and second fluid supply pipes 15 and 16 to the atmosphere.

When the first and second pressure chambers 17 and 18 repeat expansion and contraction according to the supply and the discharge of the air, in order to prevent a phenomenon in which, for example, a part of the elastic tube 10 is supported on the flexible tube 11 in an overlapping state because, for example, deviation occurs in relative positions of the elastic tube 10 and the flexible tube 11, it is desirable to interpose a stopper ring 40 for deviation prevention between the flexible tube 11 and the elastic tube 10. In this case, the stopper ring 40 is desirably caused to also function as a stopper for specifying a moving range of the slider unit 20 with respect to the longitudinal direction of the elastic tube 10.

For example, in order to prevent the air from remaining in the first and second pressure chambers 17 and 18 when the first and second fluid supply pipes 15 and 16 are opened to the atmosphere or in order to discharge the air leaking from the first and second pressure chambers 17 and 18 into between the first and second sliders 21 and 22 to an outside of the elastic tube 10, it is desirable to provide leak holes 41 in the flexible tube 11. In this case, the leak holes 41 are desirably set to a hole diameter capable of causing the air to leak in a leak amount sufficiently smaller than a flow rate of the air circulated by the first and second fluid supply pipes 15 and 16. The leak holes 41 are desirably provided at each predetermined interval along a longitudinal direction of the flexible tube 11. For example, the interval of the provision of the leak holes 41 is desirably set shorter than an interval at a time when the first and second sliders 21 and 22 are closest to each other. By setting the interval in this way, it is possible to discharge the air leaking into between the first pressure chamber 17 and the second pressure chamber 18 to the outside of the elastic tube 10 irrespective of an interval between the first and second sliders 21 and 22.

An example of a moving method of the moving device 1 configured as explained above is explained with reference to FIGS. 6 to 9. In the present embodiment, the endoscope 7 is inserted through the channels 5a and 11a set in the guide tube 5 and the driving unit 2 (see FIG. 2). Consequently, the driving unit 2 is capable of configuring an observation device in conjunction with the guide tube 5 and the endoscope 7.

Figure 6:
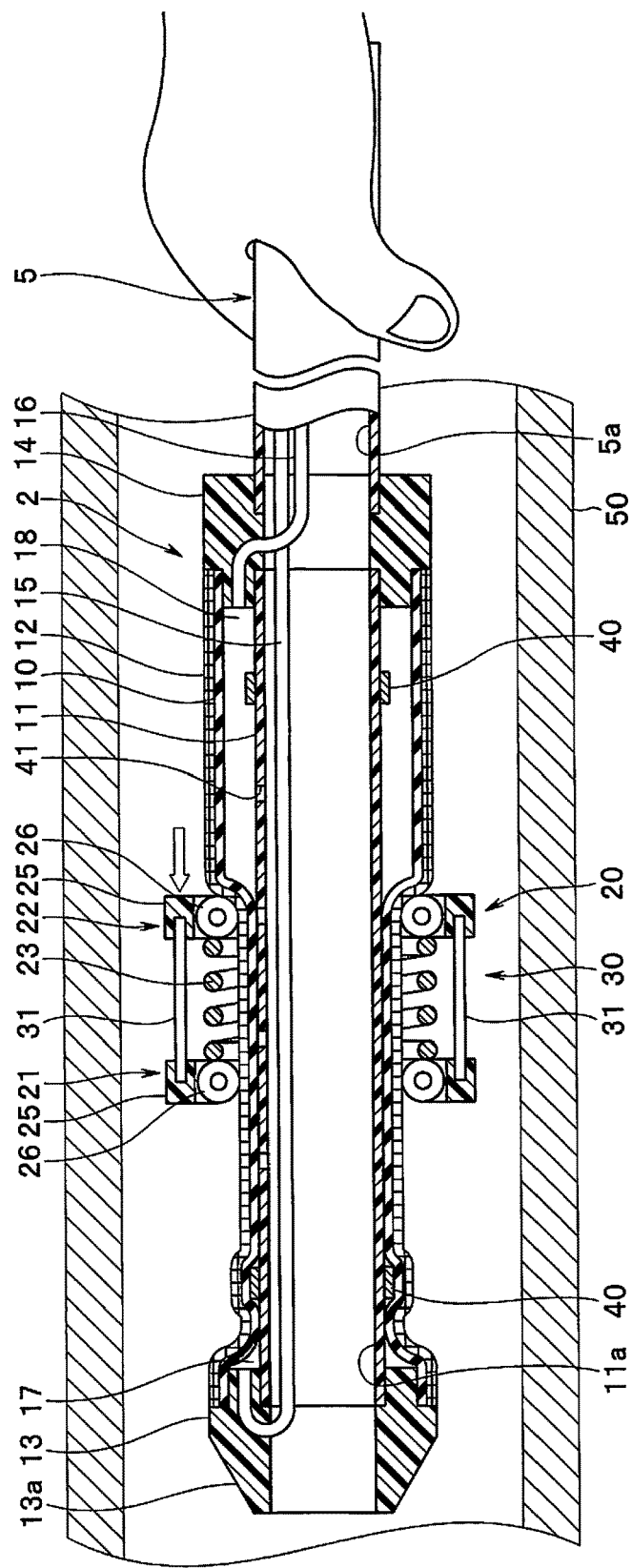
FIG. 6 relates to the first embodiment and is an operation explanatory diagram of the driving unit.

First, after the driving unit 2 of the moving device 1 is inserted into the pipe 50, as shown in FIG. 6, when a predetermined operation input to the fluid adjusting section 3 is performed in a state in which a user or the like grasps the guide tube 5 outside the pipe 50, the fluid adjusting section 3 supplies, according to control on the electropneumatic proportional valve 37 by the computer for control 38, the air adjusted to the first control pressure P1 to the second pressure chamber 18 through the second fluid supply pipe 16. Consequently, the second pressure chamber 18 starts expansion and the second slider 22 receives pressure by the expansion, whereby the slider unit 20 moves from the proximal end side to the distal end side on the elastic tube 10. That is, a slider unit moving procedure for relatively moving the slider unit 20 in a desired moving direction (in the examples shown in the figures, an advancing direction) with respect to the elastic tube 10 is realized.

Figure 7:
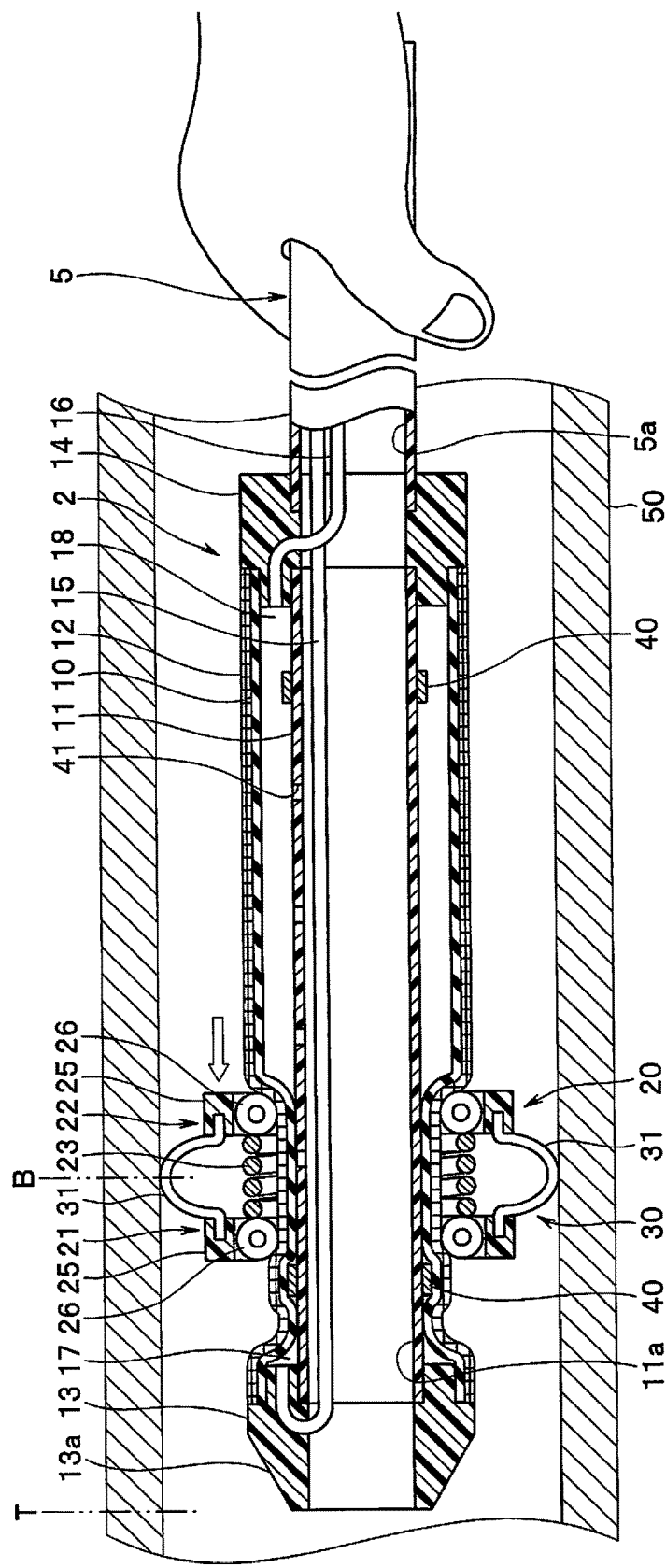
FIG. 7 relates to the first embodiment and is an operation explanatory diagram of the driving unit.

As shown in FIG. 7, even after the movement to the distal end side of the slider unit 20 is restricted by the stopper ring 40 located on the distal end side, if a force generated by the first control pressure P1 is large with respect to the urging force of the coil spring 23, the second slider 22 receives pressure from the second pressure chamber 18 and further moves to the distal end side and approaches the first slider 21 against the urging force of the coil spring 23. Consequently, the respective brake belts 31 of the brake 30 provided in the slider unit 20 are deformed in a bow shape in the radial direction of the elastic tube 10 and brought into sliding contact with an inner circumferential surface of the pipe 50. That is, a brake actuating procedure for bringing the brake 30 into sliding contact with the pipe 50, which is a target object, is realized.

Figure 8:
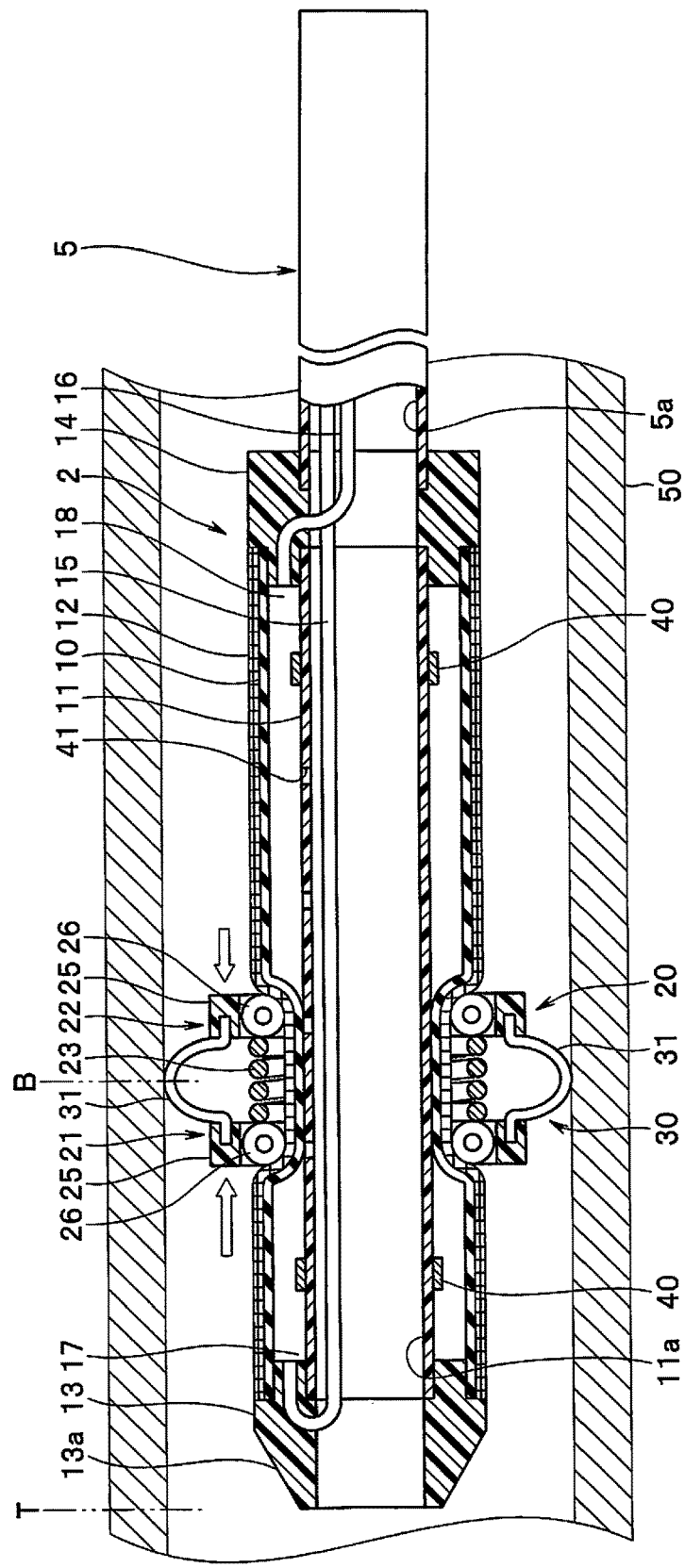
FIG. 8 relates to the first embodiment and is an operation explanatory diagram of the driving unit.

Thereafter, as shown in FIG. 8, after the user or the like releases the grasp of the guide tube 5, when a predetermined operation input to the fluid adjusting section 3 is performed, the fluid adjusting section 3 supplies, according to the control on the electropneumatic proportional valve 37 by the computer for control 38, the air adjusted to the second control pressure P2 to the first pressure chamber 17 through the first fluid supply pipe 15. Consequently, the first pressure chamber 17 starts expansion and the first slider 21 receives pressure by the expansion, whereby a force in a direction for moving from the distal end side to the proximal end side on the elastic tube 10 works on the slider unit 20 while an approached state of the first and second sliders 21 and 22 is maintained. That is, since the second control pressure P2 supplied to the first pressure chamber 17 is higher than the first control pressure P1 supplied to the second pressure chamber 18, a force in a direction for pushing back the second pressure chamber 18 to the proximal end side acts on the slider unit 20. In this case, since the respective brake belts 31 of the brake 30 provided in the slider unit 20 are set in sliding contact with an inner wall of the pipe 50, the driving unit 2 advances in the pipe 50 while a position of the slider unit 20 in the pipe 50 is unchanged. The guide tube 5 advances in the pipe 50 while being towed by the movement of the driving unit 2. That is, an elastic-tube moving procedure for relatively moving the elastic tube 10 in a desired moving direction (in the example shown in the figure, an advancing direction) with respect to the slider unit 20 is realized.

Figure 9:
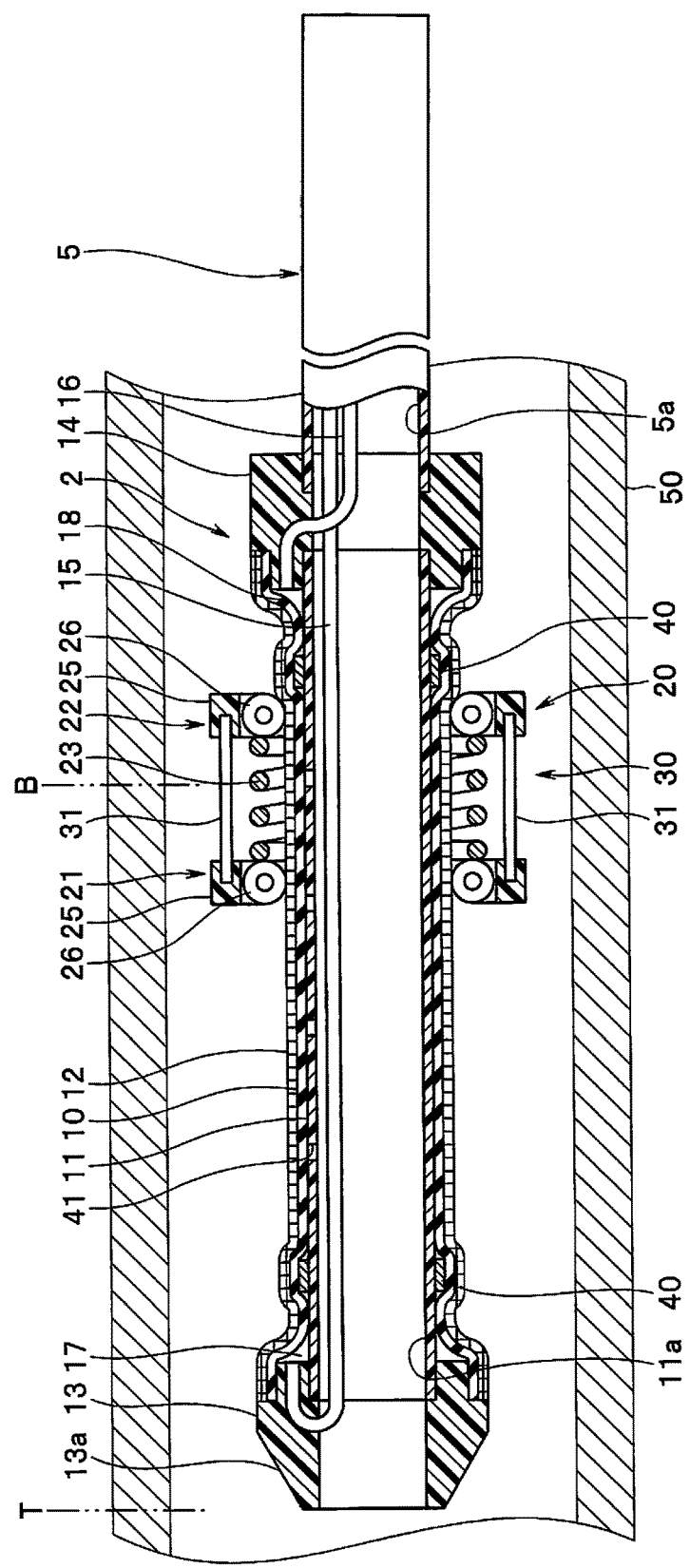
FIG. 9 relates to the first embodiment and is an operation explanatory diagram of the driving unit.

Thereafter, after the relative movement of the slider unit 20 and the elastic tube 10 is restricted by the stopper ring 40 located on the proximal end side, when an operation input to the fluid adjusting section 3 is performed by the user or the like, the fluid adjusting section 3 stops the supply of the air to the first and second pressure chambers 17 and 18 through the control on the electropneumatic proportional valve 37 by the computer for control 38 and further opens the first and second fluid supply pipes 15 and 16 to the atmosphere. Consequently, as shown in FIG. 9, the first and second sliders 21 and 22 of the slider unit 20 are separated by the urging force of the coil spring 23. The sliding contact with the inner wall of the pipe 50 by the respective brake belts 31 is released. That is, a brake releasing procedure for releasing the sliding contact of the brake 30 with the pipe 50 is realized.

Thereafter, the procedures shown in FIG. 6 to FIG. 9 are repeated, whereby it is possible to further advance the driving unit 2 in the pipe 50. In FIGS. 7 to 9, "B" indicates a reference position of the slider unit 20 at a time when the brake belts 31 come into sliding contact with the inner wall of the pipe 50. "T" indicates a distal end position of the driving unit 2 that relatively moves with respect to the reference position B. Note that, although detailed explanation is omitted, by performing procedures opposite to the procedures explained above, it is also possible to retract the driving unit 2 with performance same as the performance during the advance.

Note that, in the embodiment explained above, it is mentioned that the air adjusted to the first control pressure P1 is supplied to the second pressure chamber 18, the movement to the distal end side of the slider unit 20 is restricted by the stopper ring 40 located on the distal end side, and the respective brake belts 31 of the brake 30 provided in the slider unit 20 are deformed in a bow shape in the radial direction of the elastic tube 10 and brought into sliding contact with the inner circumferential surface of the pipe 50.

Independently of this, for example, the air adjusted to the second control pressure P2 may be supplied to the first pressure chamber 17 before reaching the stopper ring 40. In this case, the second control pressure P2 supplied to the first pressure chamber 17 is higher than the first control pressure P1 supplied to the second pressure chamber 18. Therefore, it is possible to cause a force for relatively pushing back the slider unit 20 in the proximal end side direction of the elastic tube 10 to act in a state in which the respective brake belts 31 of the brake 30 provided in the slider unit 20 are deformed in a bow shape in the radial direction of the elastic tube 10 and brought into sliding contact with the inner circumferential surface of the pipe 50. That is, it is possible to realize the brake actuating procedure and the guide-tube moving procedure as appropriate at timings before the slider unit 20 reaches the stopper ring 40.

The air adjusted to the first control pressure P1 may be supplied to the first pressure chamber 17 before reaching the stopper ring 40. In this case, both of the control pressures supplied to the first and second pressure chambers 17 and 18 are P1. Therefore, it is possible to stop the slider unit 20 and the elastic tube 10 in places of the slider unit 20 and the elastic tube 10 in the state in which the respective brake belts 31 of the brake 30 provided in the slider unit 20 are deformed in a bow shape in the radial direction of the elastic tube 10 and brought into sliding contact with the inner circumferential surface of the pipe 50. In this state, it is possible to perform observation using, for example, the endoscope 7. That is, it is possible to realize a retaining procedure for retaining a relative position of the elastic tube 10 with respect to the slider unit 20. Further, when it is desired to observe another place, it is possible to relatively move the slider unit 20 and the elastic tube 10 again by increasing one pressure (e.g., adjusting the one pressure to the second control pressure P2) or reducing the one pressure (e.g., discharging the one pressure by opening the one pressure to the atmosphere).

According to the embodiment explained above, the moving device 1 is configured to include the elastic tube 10, the sectional shape of which is elastically deformable according to an internal pressure given by the air, which is the fluid, the slider unit 20 capable of moving forward and backward in the longitudinal direction of the elastic tube 10 according to a change in the sectional shape of the elastic tube 10, the brake 30 provided in the slider unit 20 and deformed in the radial direction of the elastic tube 10 to be capable of coming into sliding contact with the inner wall of the pipe 50, which is the target object, the first and second fluid supply pipes 15 and 16 configured to respectively communicate with the insides on the distal end side and the proximal end side of the elastic tube 10, and the fluid adjusting section 3 configured to supply the air to or discharge the air from the inside of the elastic tube 10 respectively via the first and second fluid supply pipes 15 and 16. Consequently, it is possible to realize quick movement in a narrow space with a simple configuration.

That is, by performing the forward and backward movement of the slider unit 20 with the pressure of the air, which is the fluid, it is possible to move the slider unit 20 forward and backward in a quick motion compared with when an electric actuator or the like is used. A forward and backward movement distance of the slider unit 20 can be optionally set according to length adjustment of the elastic tube 10. If the elastic tube 10 is set long, it is possible to increase a stroke of the driving unit 2 advancing and retracting in the pipe 50 according to a series of operation. It is possible to more efficiently realize quick movement in the narrow space. In addition, the driving unit 2 is configured using a hydrodynamic actuator that operates the slider unit 20 with the air supplied into the elastic tube 10. Therefore, it is possible to simplify structure compared with when an electric actuator or the like is used.

In this case, the slider unit 20 is configured to include the first slider 21 configured to partially restrict the expansion of the sectional shape of the elastic tube 10 to form the first pressure chamber 17 communicating with the first fluid supply pipe 15 on the distal end side of the elastic tube 10 and receive a pressure from the first pressure chamber 17 and capable of moving on the elastic tube 10 and the second slider 22 configured to partially restrict the expansion of the sectional shape of the elastic tube 10 to form the second pressure chamber 18 communicating with the second fluid supply pipe 16 on the distal end side of the elastic tube 10 and receive pressure from the second pressure chamber 18 and capable of moving on the elastic tube 10. Further, the brake 30 is configured using the brake belts 31 suspended between the first and second sliders 21 and 22. Consequently, it is possible to realize the forward and backward movement of the slider unit 20 and the operation of the brake 30 only with fluid supply in two systems to the distal end side and the proximal end side of the elastic tube 10. It is possible to further simplify the configuration of the driving unit 2.

By inserting the flexible tube 11 through the elastic tube 10, it is possible to cause the flexible tube 11 to function as a core material. It is possible to prevent bending and the like of the elastic tube 10 and improve insertability of the driving unit 2 into the pipe 50. It is possible to realize a stable advancing and retracting motion of the slider unit 20.

By interposing the mesh tube 12 configured to limit elastic deformation of the elastic tube 10 between the elastic tube 10 and the slider unit 20, it is possible to prevent local expansion and the like of the elastic tube 10 and efficiently transmit internal pressure of the elastic tube 10 to the slider unit 20. Further, by interposing the mesh tube 12, it is possible to markedly reduce sliding resistance of the slider unit 20 compared with when the slider unit 20 moves in the longitudinal direction while being in direct contact with the elastic tube 10.

Figure 10:
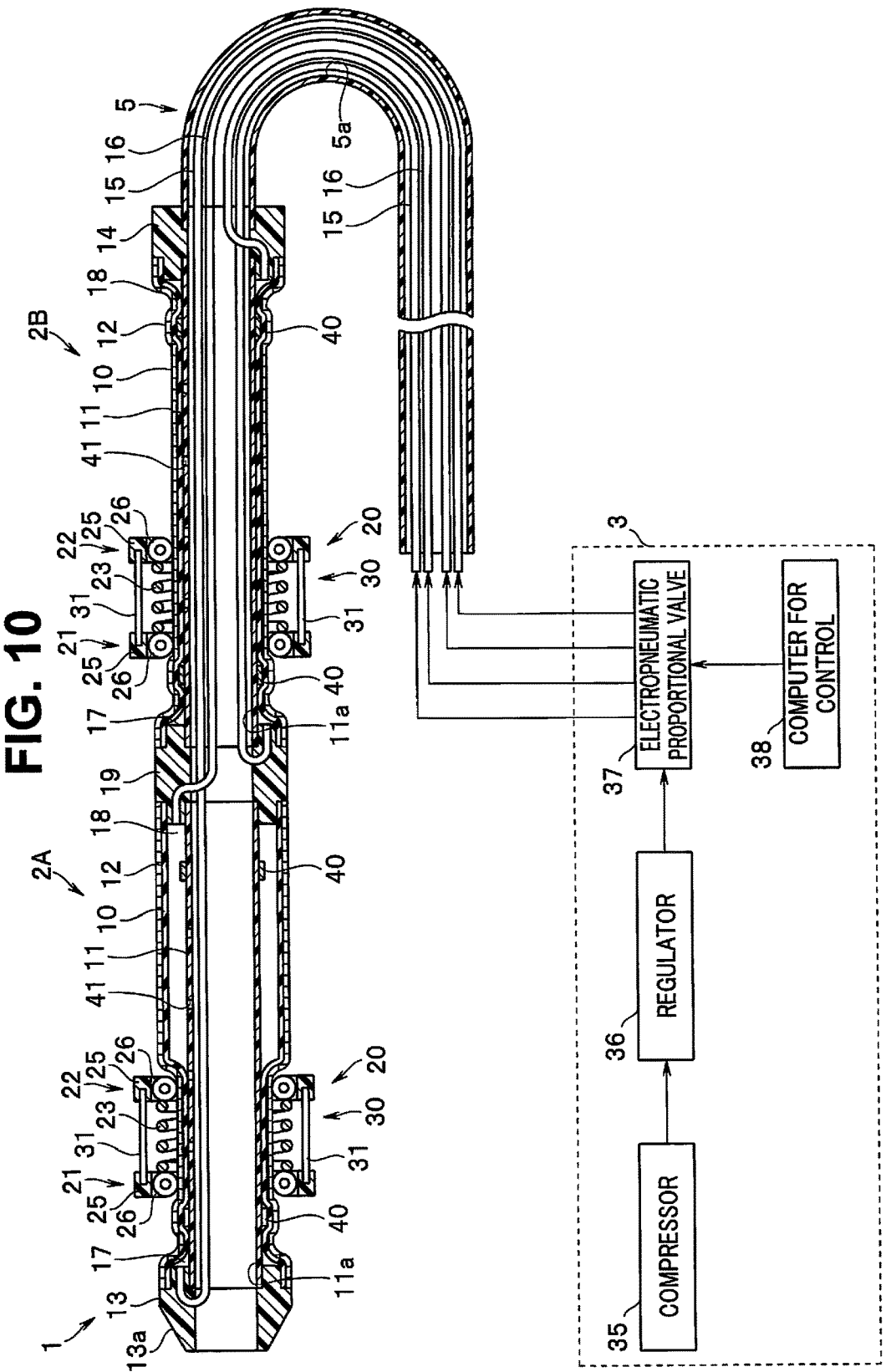
FIG. 10 relates to a second embodiment of the present invention and is a schematic configuration diagram of a moving device.
Figure 11:
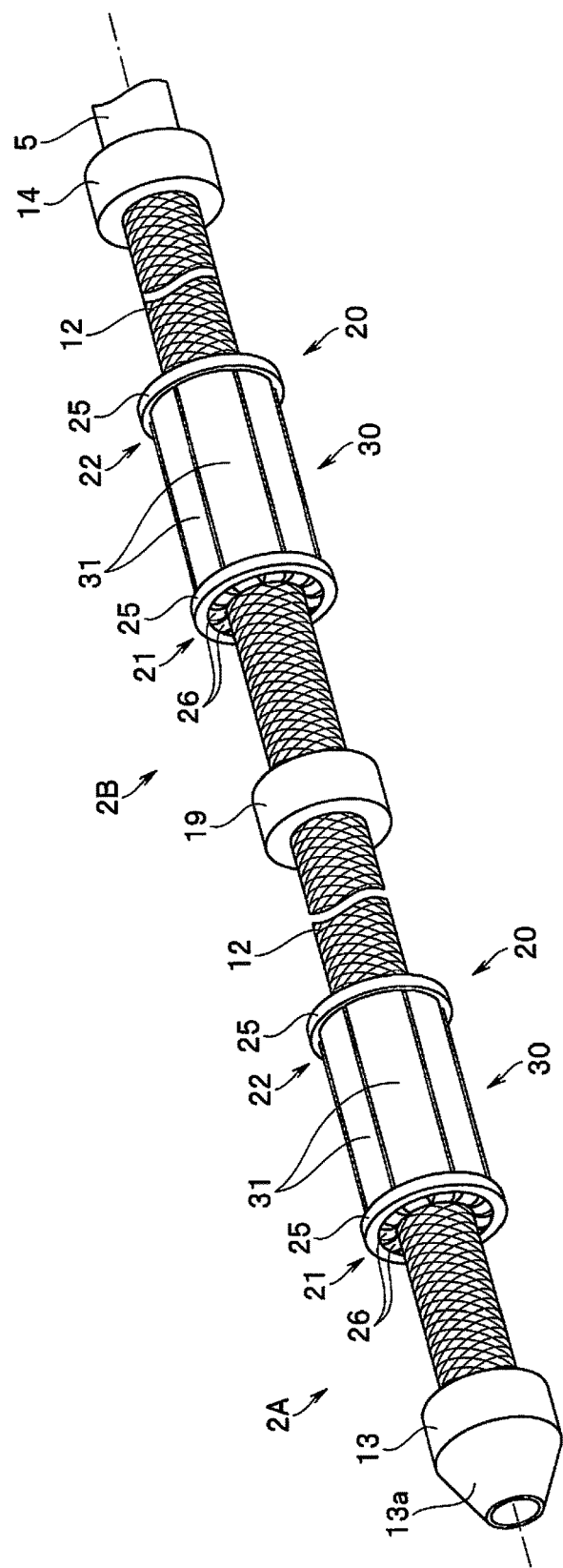
FIG. 11 relates to the second embodiment and is a perspective view of driving units.
Figure 12:
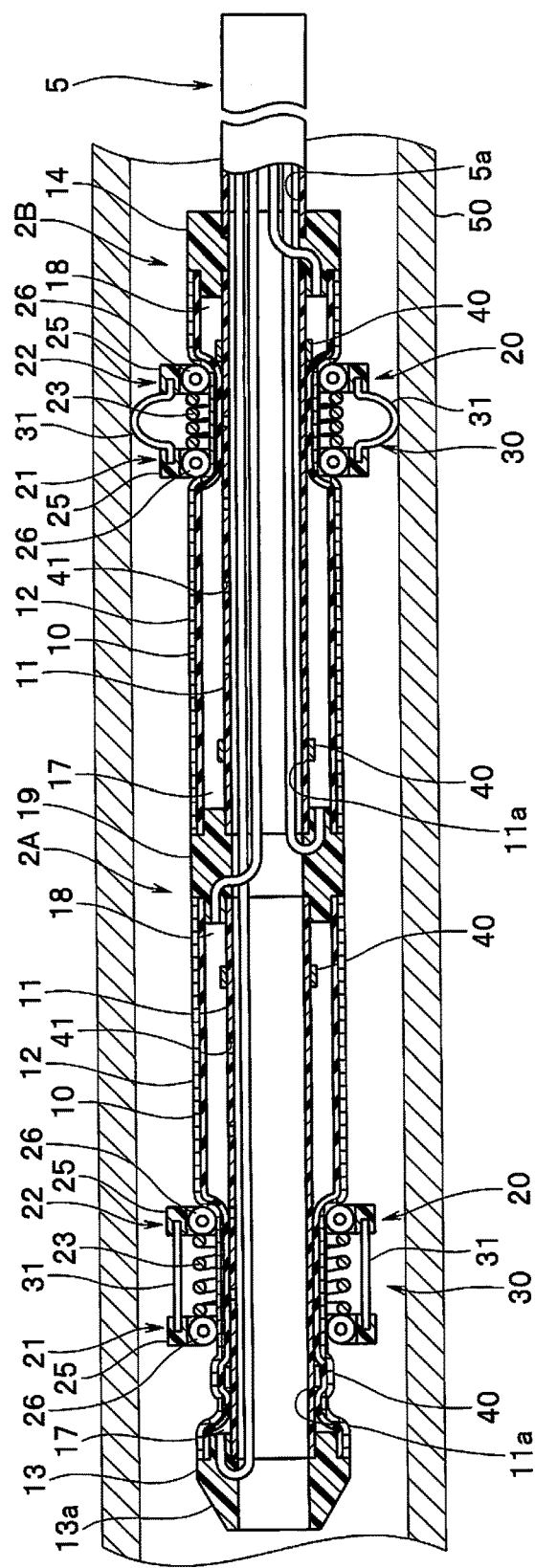
FIG. 12 relates to the second embodiment and is an operation explanatory diagram of the driving units.
Figure 13:
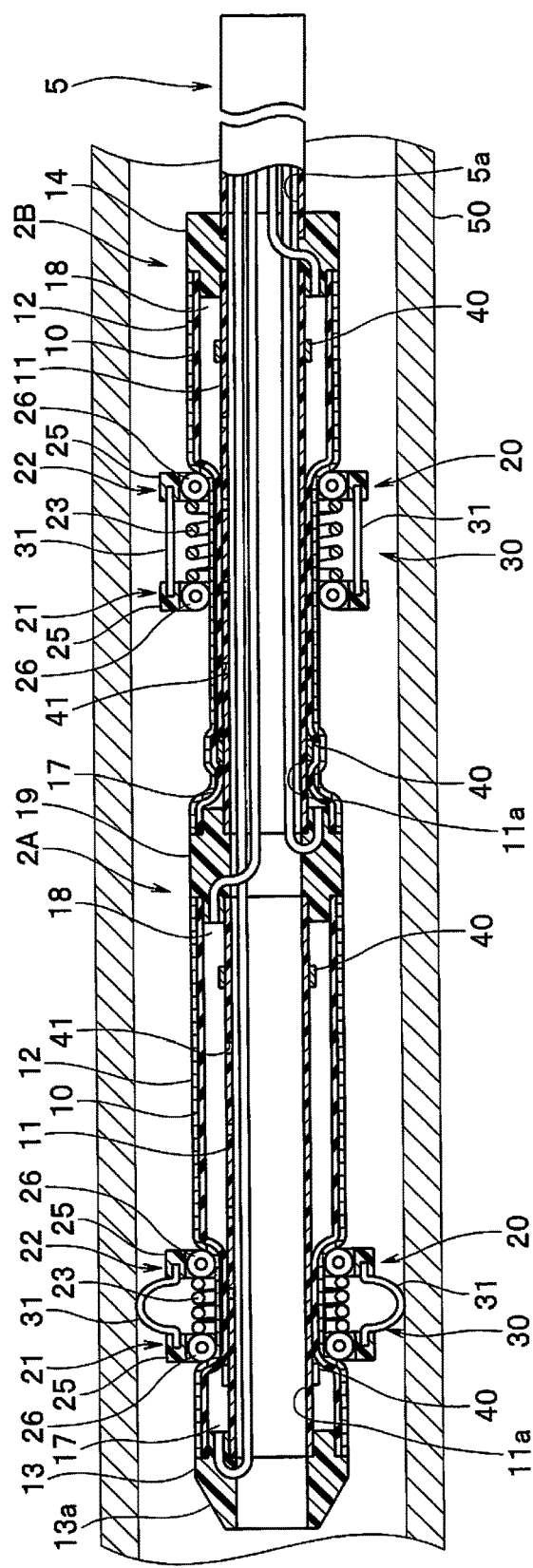
FIG. 13 relates to the second embodiment and is an operation explanatory diagram of the driving units.
Figure 14:
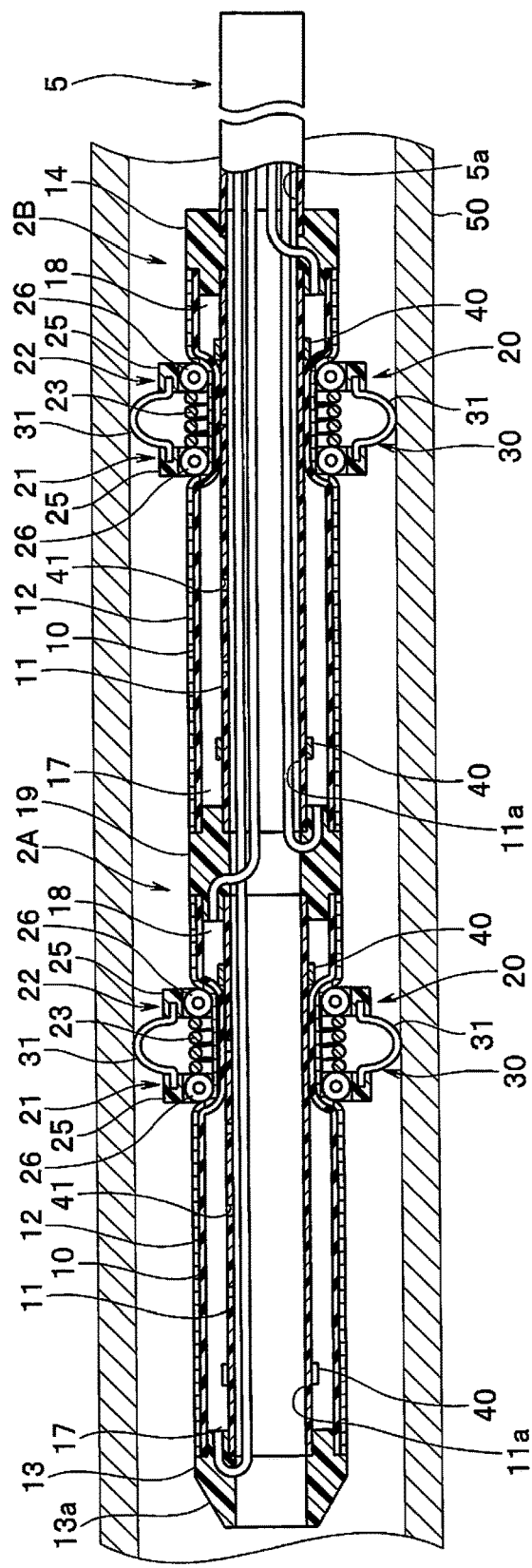
FIG. 14 relates to the second embodiment and is an operation explanatory diagram of the driving units.

FIG. 10 to FIG. 14 relate to a second embodiment of the present invention. FIG. 10 is a schematic configuration diagram of a moving device. FIG. 11 is a perspective view of driving units. FIG. 12 to FIG. 14 are operation explanatory diagrams of the driving units. Note that the present embodiment is mainly different from the first embodiment in that a front and rear pair of driving units are disposed on a distal end side of a guide pipe. Otherwise, components same as the components in the first embodiment are denoted by the same reference numerals and signs and explanation of the components is omitted.

As shown in FIGS. 10 and 11, the moving device 1 of the present embodiment includes first and second driving units 2A and 2B formed in a pair in a front-rear direction at a distal end of the guide tube 5 and the fluid adjusting section 3 capable of supplying air serving as fluid to and discharging the air from the first and second driving units 2A and 2B.

The first and second driving units 2A and 2B have a configuration substantially the same as the configuration of the driving unit 2 explained in the first embodiment. However, in the present embodiment, a proximal-end-side end part member of the first driving unit 2A and a distal-end-side end part member of the second driving unit 2B are configured by an integral end part member 19.

The fluid adjusting section 3 of the present embodiment is capable of individually supplying the air to or discharging the air from the respective first and second pressure chambers 17 and 18 formed in the first driving unit 2A and the respective first and second pressure chambers 17 and 18 formed in the second driving unit 2B.

An example of action of the moving device 1 configured as explained above is explained with reference to FIG. 11 to FIG. 14.

First, after the first and second driving units 2A and 2B of the moving device 1 are inserted into the pipe 50, when an operation input to the fluid adjusting section 3 is performed by a user or the like, the fluid adjusting section 3 supplies, according to control on the electropneumatic proportional valve 37 by the computer for control 38, the air adjusted to the first control pressure P1 to the first pressure chamber 17 through the first fluid supply pipe 15 of the second driving unit 2B. Consequently, the slider unit 20 of the second driving unit 2B moves from a distal end side to a proximal end side on the elastic tube 10. Even after the movement to the proximal end side of the slider unit 20 of the second driving unit 2B is restricted by the stopper ring 40 located on the proximal end side, if a force generated by the first control pressure P1 is large with respect to an urging force of the coil spring 23, the first slider 21 receives pressure from the first pressure chamber 17 and further moves to the proximal end side and approaches the second slider 22 against the urging force of the coil spring 23. Consequently, the respective brake belts 31 of the brake 30 provided in the slider unit 20 of the second driving unit 2B are deformed in a bow shape in the radial direction of the elastic tube 10 and brought into sliding contact with the inner circumferential surface of the pipe 50. Thereafter, when an operation input to the fluid adjusting section 3 is performed by the user or the like, the fluid adjusting section 3 supplies, according to the control on the electropneumatic proportional valve 37 by the computer for control 38, the air adjusted to the first control pressure P1 to the second pressure chamber 18 through the second fluid supply pipe 16 of the first driving unit 2A. Consequently, the slider unit 20 of the first driving unit 2A moves from the proximal end side to the distal end side on the elastic tube 10. That is, a first slider-unit moving procedure for relatively moving the slider unit 20 of the first driving unit 2A in a desired moving direction (in the example shown in the figures, an advancing direction) with respect to the elastic tube 10 of the first driving unit 2A is realized.

As shown in FIG. 13, even after the movement to the distal end side of the slider unit 20 of the first driving unit 2A is restricted by the stopper ring 40 located on the distal end side, if a force generated by the first control pressure P1 is large with respect to the urging force of the coil spring 23, the second slider 22 receives pressure from the second pressure chamber 18 and further moves to the distal end side and approaches the first slider 21 against the urging force of the coil spring 23. Consequently, the respective brake belts 31 of the brake 30 provided in the slider unit 20 of the first driving unit 2A are deformed in a bow shape in the radial direction of the elastic tube 10 and brought into sliding contact with the inner circumferential surface of the pipe 50. That is, a first brake actuating procedure for bringing the brake 30 of the first driving unit 2A into sliding contact with the pipe 50, which is the target object, is realized. Thereafter, when an operation input to the fluid adjusting section 3 is performed by the user or the like, according to the control on the electropneumatic proportional valve 37 by the computer for control 38, the fluid adjusting section 3 opens the first fluid supply pipe 15 of the second driving unit 2B to the atmosphere and supplies the air adjusted to the first control pressure P1 to the second pressure chamber 18 through the second fluid supply pipe 16 of the second driving unit 2B. Consequently, the slider unit 20 of the second driving unit 2B moves from the proximal end side to the distal end side on the elastic tube 10. That is, a second brake releasing procedure for releasing the sliding contact of the second driving unit 2B with the pipe of the brake 30 and a second slider-unit moving procedure for relatively moving the slider unit 20 of the second driving unit 2B in a desired moving direction (in the example shown in the figure, an advancing direction) with respect to the elastic tube 10 of the second driving unit 2B are sequentially realized.

Even after the movement to the distal end side of the slider unit 20 of the second driving unit 2B is restricted by the stopper ring 40 located on the distal end side, if force generated by the first control pressure P1 is large with respect to the urging force of the coil spring 23, the second slider 22 receives pressure from the second pressure chamber 18 and further moves to the distal end side and approaches the first slider 21 against the urging force of the coil spring 23. Consequently, the respective brake belts 31 of the brake 30 provided in the slider unit 20 of the second driving unit 2B are deformed in a bow shape in the radial direction of the elastic tube 10 and brought into contact with the inner circumferential surface of the pipe 50. That is, a second brake actuating procedure for bringing the brake 30 of the second driving unit 2B into sliding contact with the pipe 50 is realized. In this way, in a state in which both of the respective slider units 20 of the first and second driving units 2A and 2B are located on the distal end side and retained in the pipe 50 by the brake 30, when an operation input to the fluid adjusting section 3 is performed by the user or the like, the fluid adjusting section 3 supplies, according to the control on the electropneumatic proportional valve 37 by the computer for control 38, the air adjusted to the second control pressure P2 respectively to the first pressure chambers 17 through the respective first fluid supply pipes 15 of the first and second driving units 2A and 2B. Consequently, as shown in FIG. 14, the respective first pressure chambers 17 of the first and second driving units 2A and 2B start expansion and the respective first sliders 21 receive pressure by the expansion, whereby a force in a direction for moving from the distal end side to the proximal end side on the respective elastic tubes 10 works on the respective slider units 20 while the approached state of the respective first and second sliders 21 and 22 is maintained. That is, the second control pressure P2 supplied to the respective first pressure chambers 17 of the first and second driving units 2A and 2B is higher than the first control pressure P1 supplied to the respective second pressure chambers 18. Therefore, a force in a direction for pushing back the respective second pressure chambers 18 to the proximal end side acts on the respective slider units 20. In this case, the respective brake belts 31 of the respective brakes 30 provided in the respective slider units 20 are set in sliding contact with the inner wall of the pipe 50. Therefore, the first and second driving units 2A and 2B integrally advance in the pipe 50 while positions of the respective slider units 20 in the pipe 50 are unchanged. The guide tube 5 advances in the pipe 50 while being towed by the movement of the first and second driving units 2A and 2B. That is, a guide-tube moving procedure for relatively moving the elastic tube 10 of the first driving unit 2A in a desired moving direction (in the example shown in the figure, an advancing direction) with respect to the slider unit 20 of the first driving unit 2A and relatively moving the elastic tube 10 of the second driving unit 2B in a desired moving direction (in the example shown in the figure, the advancing direction) with respect to the slider unit 20 of the second driving unit 2B is realized. Note that, although detailed explanation is omitted, by performing procedures opposite to the procedures explained above, it is also possible to retract the first and second driving units 2A and 2B with performance same as the performance during the advance. Further, it is also possible to realize the retaining procedure and the like at any timing according to control and the like same as the control and the like in the first embodiment.

According to the embodiment explained above, in addition to the effects explained in the first embodiment, since the moving device 1 includes the first and second driving units 2A and 2B forming the pair in the front-rear direction, there is an effect that the moving device 1 is capable of autonomously moving without requiring a grasping motion or the like of the guide tube 5 by the user or the like.

Figure 15:
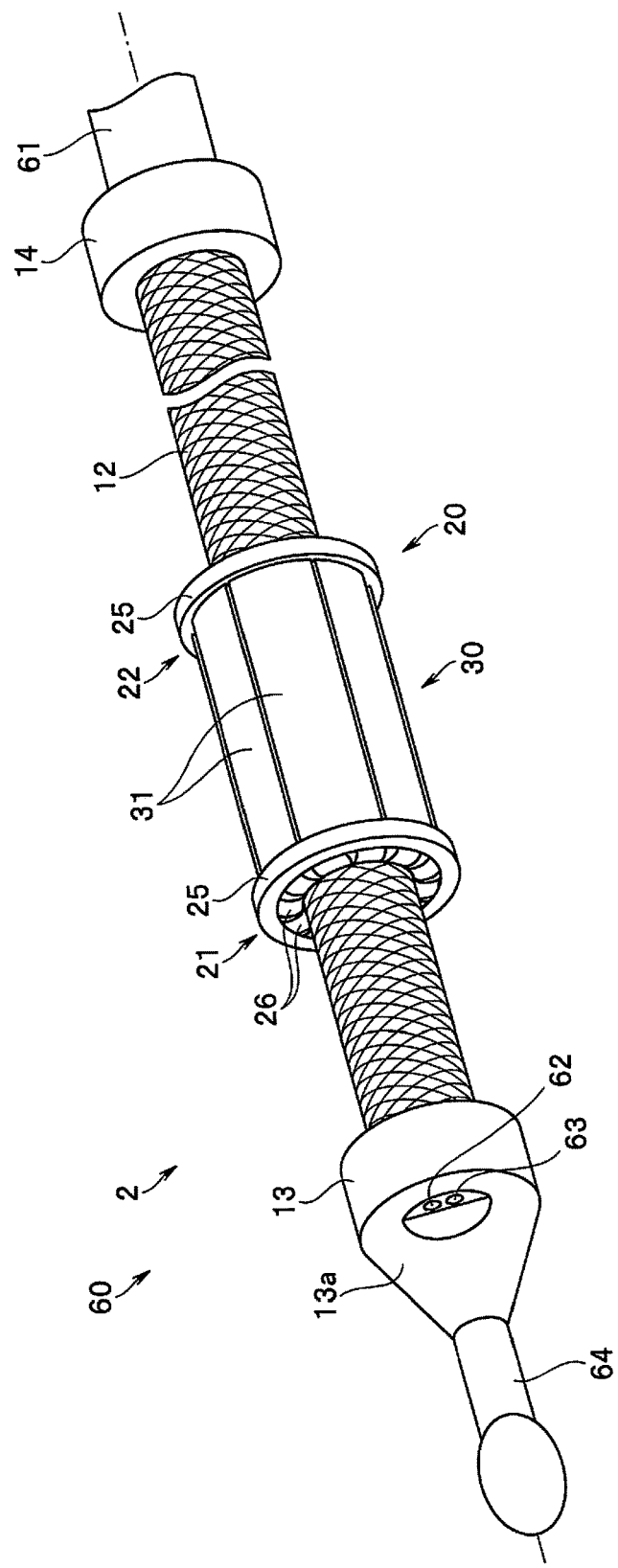
FIG. 15 relates to a third embodiment of the present invention and is a perspective view of a driving unit incorporated in an endoscope.

FIG. 15 relates to a third embodiment of the present invention. FIG. 15 is a perspective view of a driving unit incorporated in an endoscope. Note that the present embodiment is mainly different from the first embodiment in that a moving device is applied to an endoscope, which is an example of an observation device. Otherwise, components same as the components in the first embodiment are denoted by the same reference numerals and signs and explanation of the components is omitted.

As shown in FIG. 15, an endoscope 60 of the present embodiment includes the driving unit 2 at a distal end of a long insertion section 61.

In the distal-end-side end part member 13 configuring the driving unit 2, for example, an illumination lens 62, which is an illumination optical system, and an observation window 63, which is an objective optical system, for forming an object image on a not-shown image pickup device or the like are provided as an observing section.

Further, a protrusion for lead 64 for leading the driving unit 2 in the pipe 50 is protruded from the distal-end-side end part member 13.

According to the embodiment explained above, it is possible to achieve action and effects substantially the same as the action and effects in the first embodiment.

Figure 16:
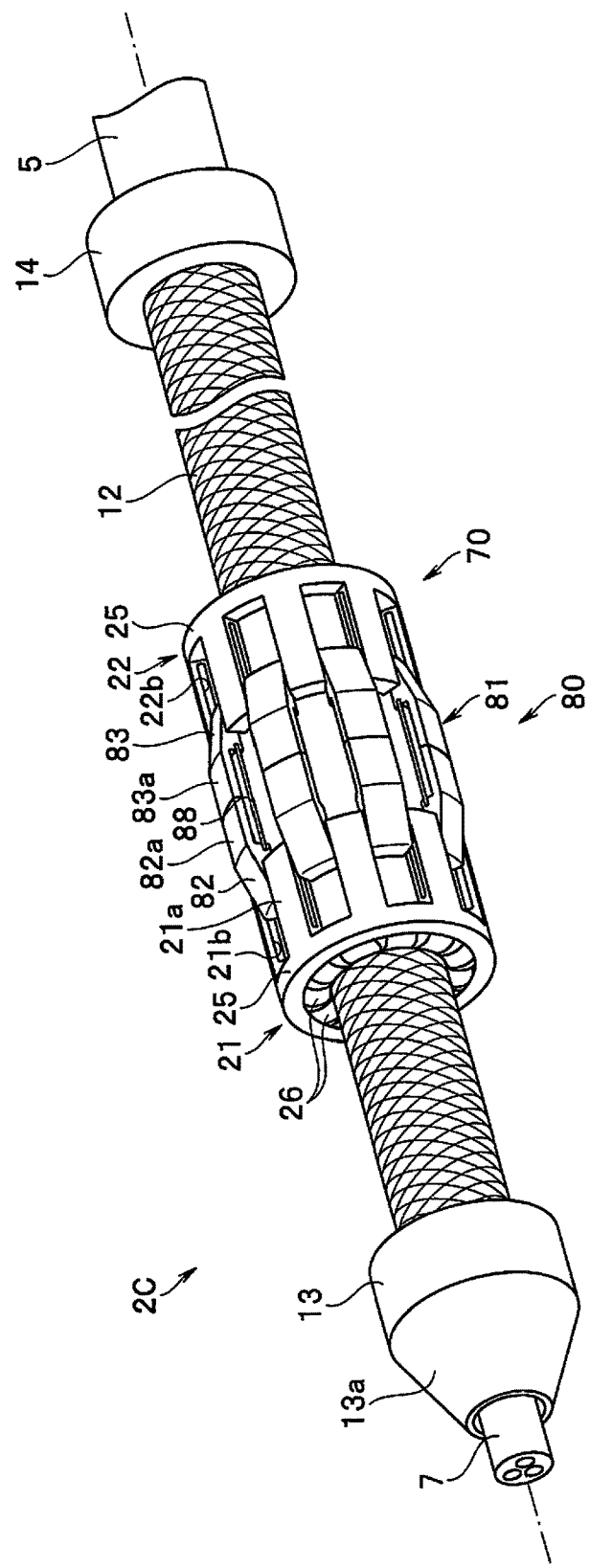
FIG. 16 relates to a fourth embodiment of the present invention and is a perspective view of a driving unit.
Figure 17:
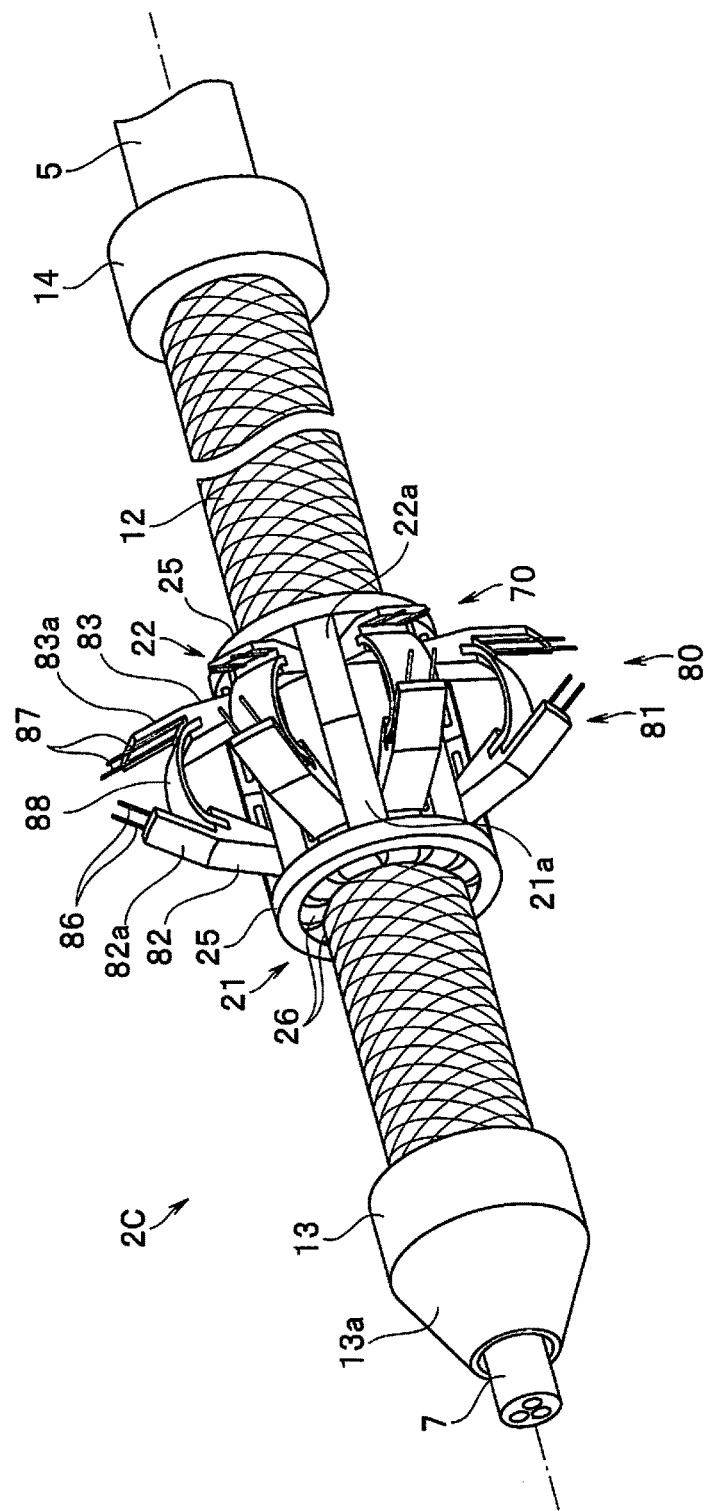
FIG. 17 relates to the fourth embodiment and is a perspective view of the driving unit at a time when a brake is in an actuated state.
Figure 18:
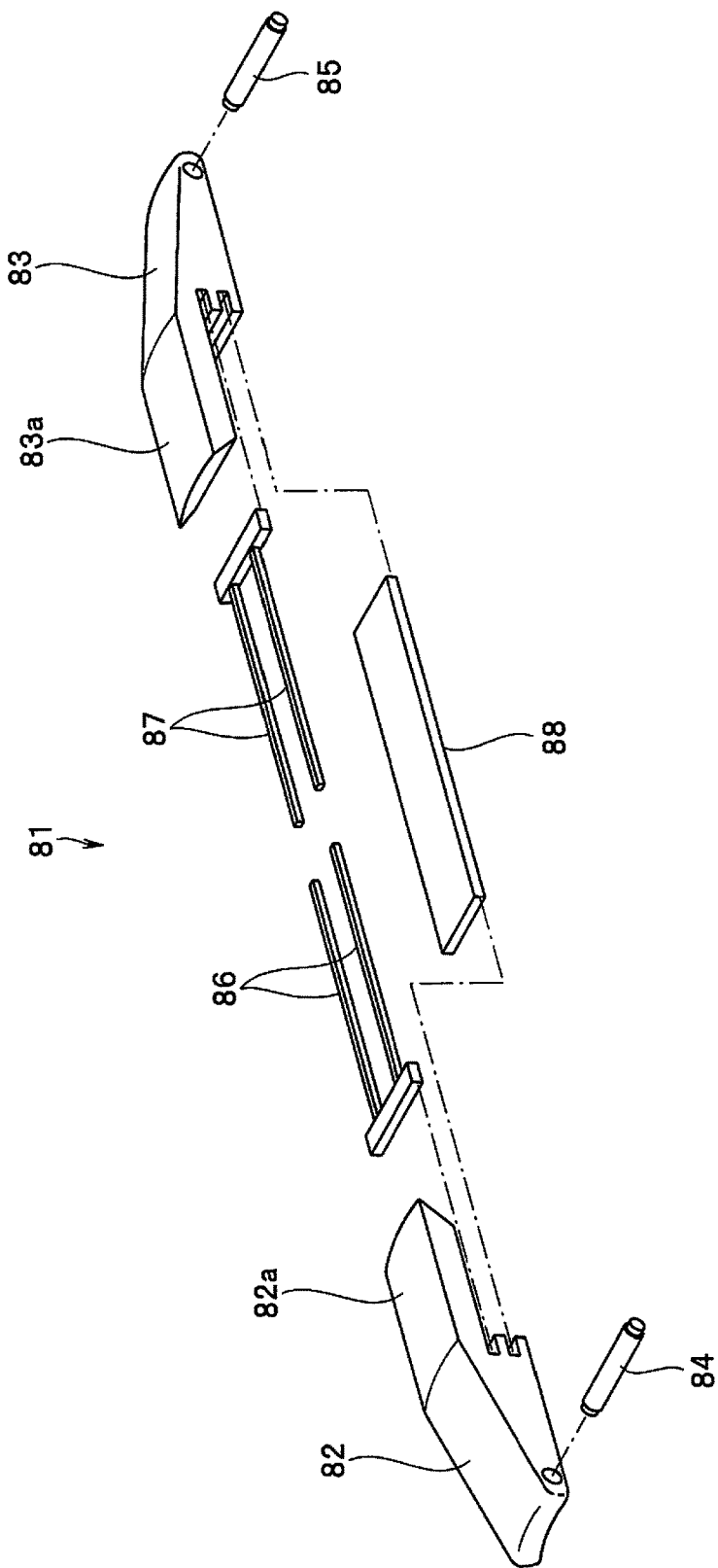
FIG. 18 relates to the fourth embodiment and is an exploded perspective view showing a main part of a brake member.
Figure 19:
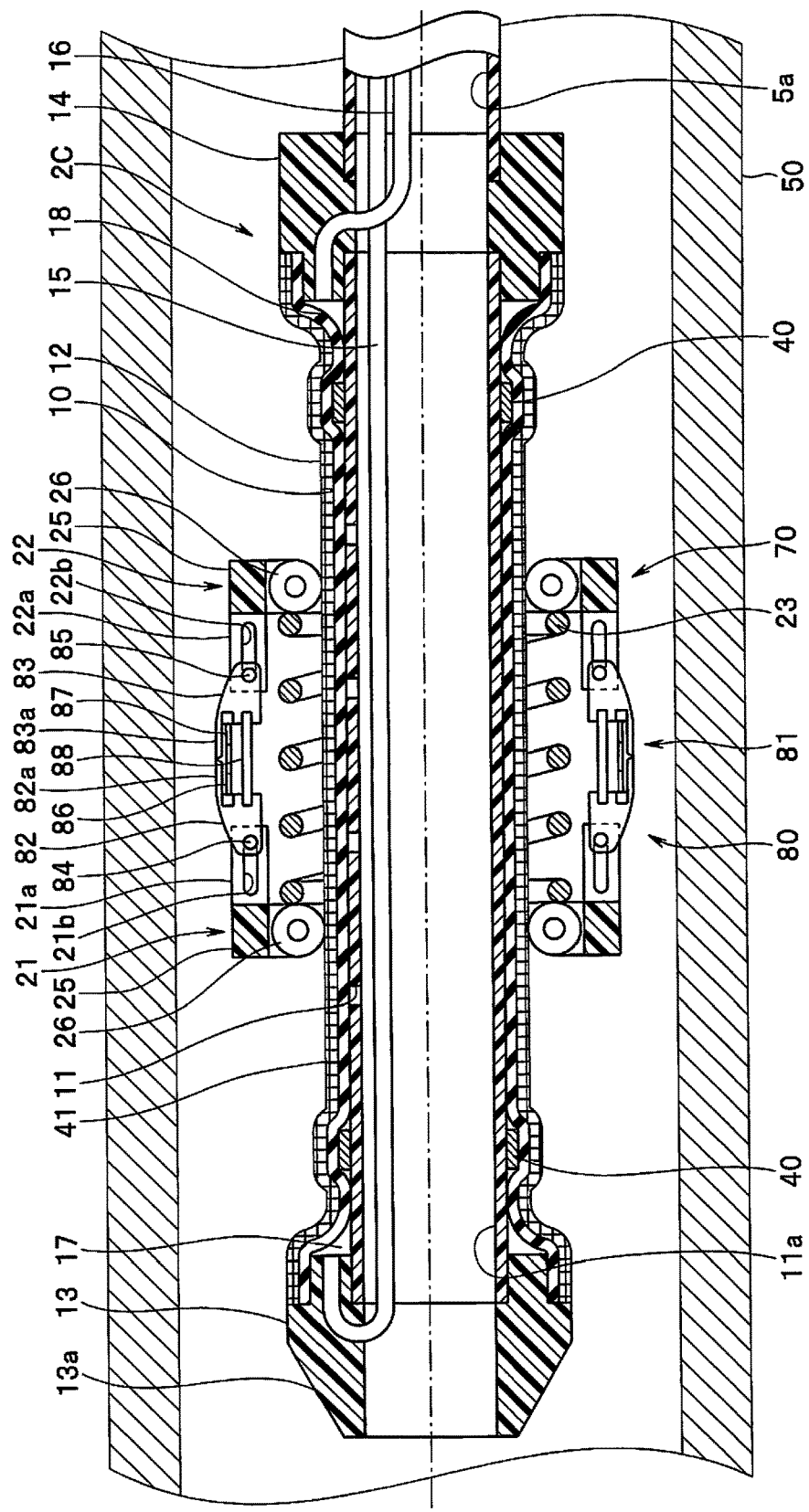
FIG. 19 relates to the fourth embodiment and is a main part sectional view schematically showing the driving unit at a time when the brake is in an unactuated state in a pipe.
Figure 20:
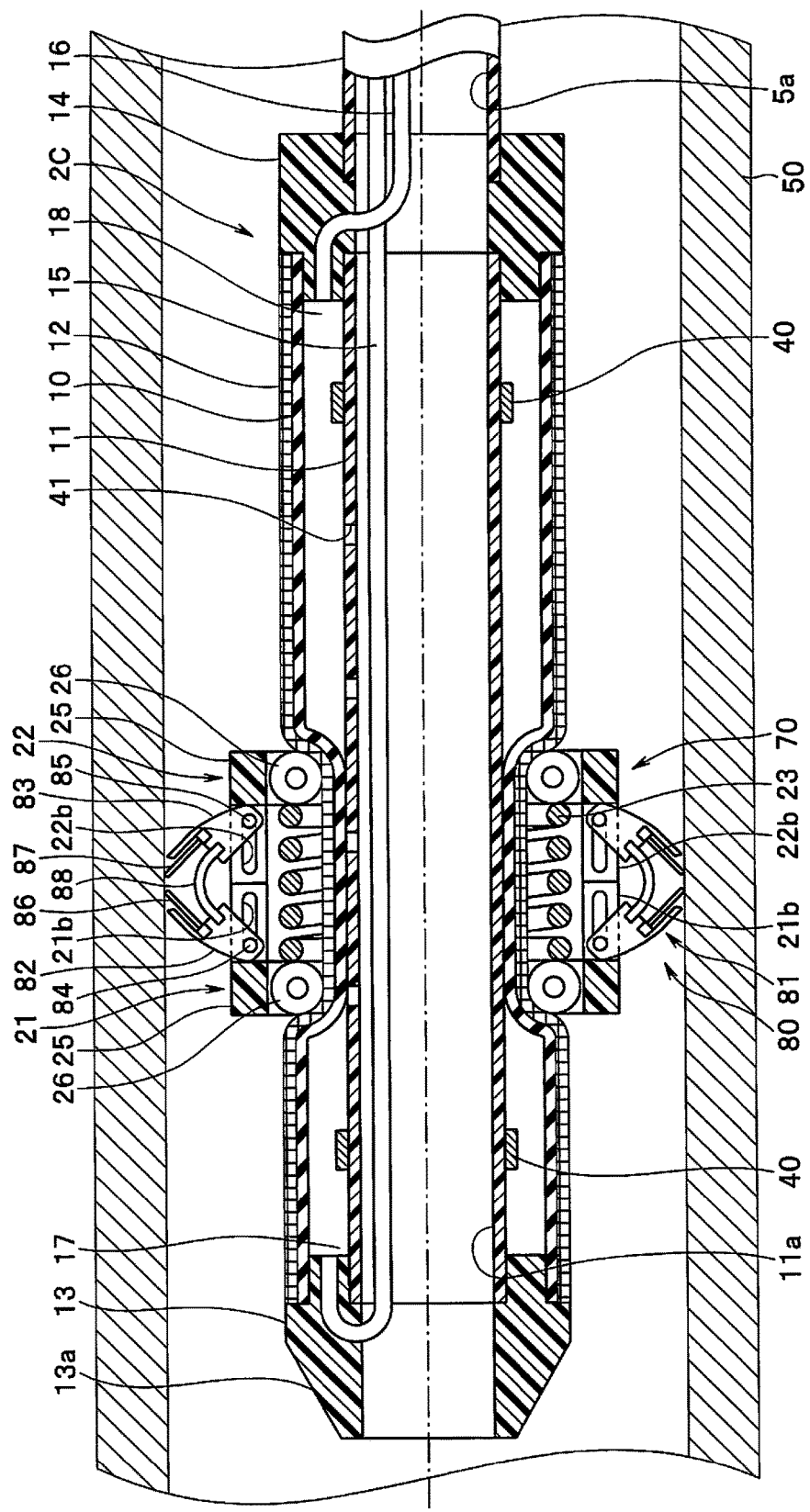
FIG. 20 relates to the fourth embodiment and is a main part sectional view schematically showing the driving unit at a time when the brake is in the actuated state in the pipe.
Figure 21:
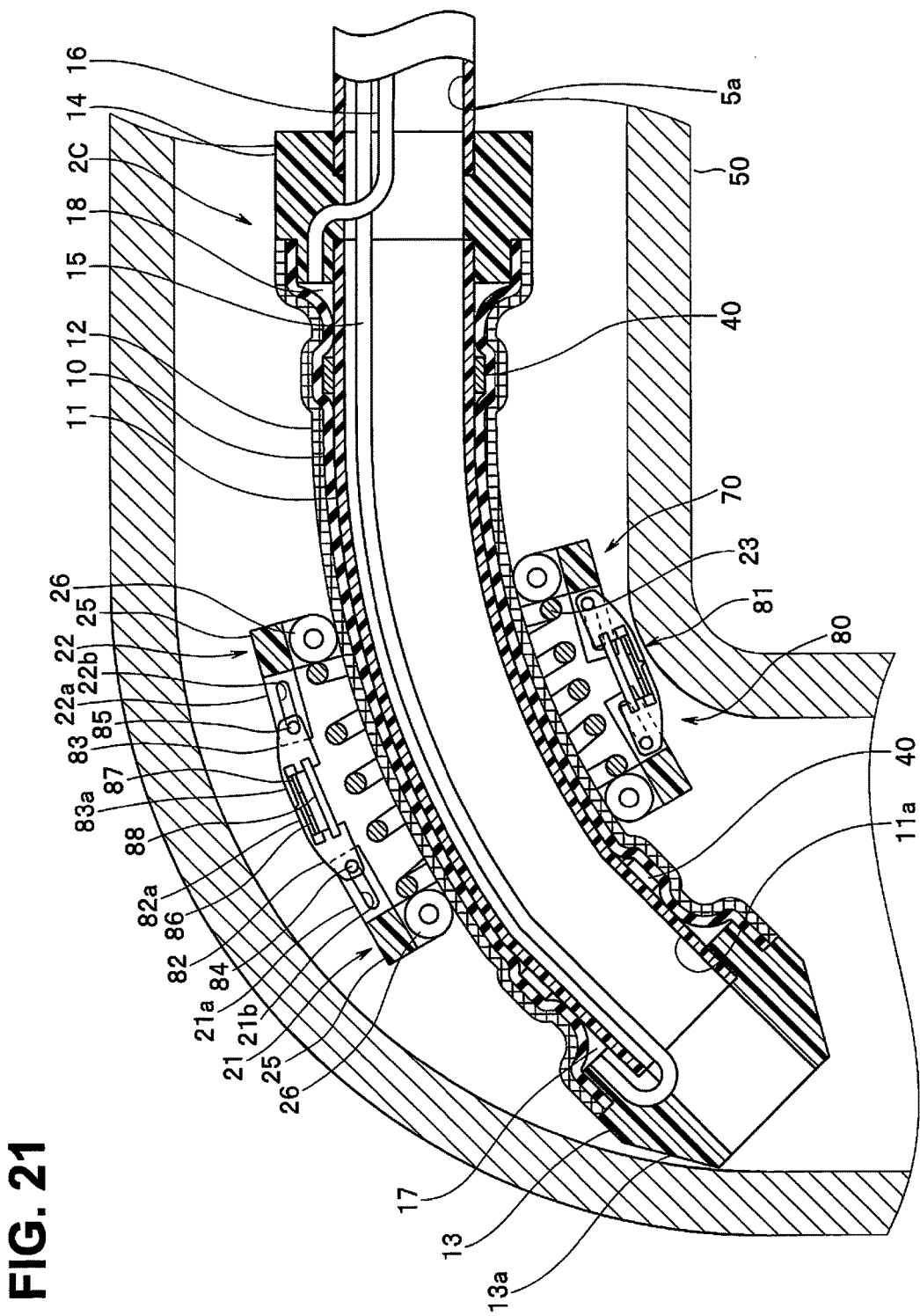
FIG. 21 relates to the fourth embodiment and is a main part sectional view schematically showing a state of a slider unit at a time when a slider passes through a bent pipe.

FIG. 16 to FIG. 21 relate to a fourth embodiment of the present invention. FIG. 16 is a perspective view of a driving unit. FIG. 17 is a perspective view of the driving unit at a time when a brake is in an actuated state. FIG. 18 is an exploded perspective view showing a main part of a brake member. FIG. 19 is a main part sectional view schematically showing the driving unit at a time when the brake is in an unactuated state in a pipe. FIG. 20 is a main part sectional view schematically showing the driving unit at a time when the brake is in the actuated state in the pipe. FIG. 21 is a main part sectional view schematically showing a state of a slider unit at a time when the slider unit passes through a bent pipe. Note that the present embodiment is mainly different from the first embodiment in a configuration of the brake provided in the slider unit. Otherwise, components same as the components in the first embodiment are denoted by the same reference numerals and signs as appropriate and explanation of the components is omitted.

As shown in FIGS. 19 and 20, a slider unit 70 configuring a driving unit 2C of the present embodiment includes the first slider 21 attached to the outer circumference side of the elastic tube 10 via the mesh tube 12, the second slider 22 attached to the outer circumference side of the elastic tube 10 via the mesh tube 12 further on a proximal end side than the first slider 21, and the coil spring 23 functioning as an urging member configured to urge the first and second sliders 21 and 22 in separating directions.

A plurality of protrusions for guide 21a extending to a proximal end side (the second slider 22 side) along an axial direction of the first slider 21 are provided in the first slider 21. The protrusions for guide 21a are annularly arrayed each predetermined interval apart from one another on the outer circumference side of the coil spring 23 (see FIGS. 16 and 17). Guide grooves 21b extending along the axial direction of the first slider 21 are respectively provided in both side portions of the respective protrusions for guide 21a.

A plurality of protrusions for guide 22a extending to a distal end side (the first slider 21 side) along an axial direction of the second slider 22 are provided in the second slider 22. The protrusions for guide 22a are annularly arrayed each predetermined interval apart from one another to be respectively opposed to the protrusions for guide 21a of the first slider 21 on the outer circumference side of the coil spring 23 (see FIGS. 16 and 17). Guide grooves 22b extending along the axial direction of the second slider 22 are respectively provided in both side portions of the protrusions for guide 22a.

As shown in FIG. 16 to FIG. 18, a plurality of brake members 81 configuring a brake 80 are suspended between the first and second sliders 21 and 22 of the slider unit 70.

The respective brake members 81 of the present embodiment includes a first swinging body 82 supported by the first slider 21 and a second swinging body 83 supported by the second slider 22.

The first swinging body 82 is disposed between the protrusions for guide 21a, 21a adjacent to each other in the first slider 21 (see FIGS. 16 and 17). A shaft section 84 is provided on a distal end side (a fixed end side) of the first swinging body 82 (see FIG. 18). Both ends of the shaft section 84 are respectively engaged in the guide grooves 21b, 21b provided in the protrusions for guide 21a, 21a (see FIGS. 19 and 20). Consequently, the first swinging body 82 is supported between the protrusions for guide 21a, 21a to be capable of moving forward and backward in the axial direction of the first slider 21 along the guide grooves 21b, 21b and capable of swinging in a diameter expansion direction of the first slider 21.

A locking claw section 86 functioning as a contact member is provided on a proximal end side (a free end side) of the first swinging body 82. The locking claw section 86 is capable of swinging integrally with the first swinging body 82. When the first swinging body 82 is displaced in the diameter expansion direction by swinging, the locking claw section 86 is capable of coming into sliding contact with an inner circumferential surface of a pipe or the like. Note that a claw cover 82a for covering a part of the locking claw section 86 is integrally formed in the first swinging body 82.

The second swinging body 83 is disposed between the protrusions for guide 22a, 22a adjacent to each other in the second slider 22 (see FIGS. 16 and 17). A shaft section 85 is provided on a proximal end side (a fixed end side) of the second swinging body 83 (see FIG. 18). Both ends of the shaft section 85 are respectively engaged in the respective guide grooves 22b, 22b provided in the protrusions for guide 22a, 22a (see FIGS. 19 and 20). Consequently, the second swinging body 83 is supported between the protrusions for guide 22a, 22a in a position opposed to the first swinging body 82 to be capable of moving forward and backward in the axial direction of the second slider 22 along the guide grooves 22b, 22b and capable of swinging in the diameter expansion direction of the second slider 22.

A locking claw section 87 functioning as a contact member is provided on a distal end side (a free end side) of the second swinging body 83. The locking claw section 87 is capable of swinging integrally with the second swinging body 83. When the second swinging body 83 is displaced in the diameter expansion direction by swinging, the locking claw section 87 is capable of coming into sliding contact with an inner circumferential surface of a pipe or the like. Note that a claw cover 83a for covering a part of the locking claw section 87 is integrally formed in the second swinging body 83.

Further, a coupling member 88 for coupling the free end sides of the first and second swinging bodies 82 and 83 (i.e., the proximal end side of the first swinging body 82 and the distal end side of the second swinging body 83) is provided between the first and second swinging bodies 82 and 83. In the present embodiment, the coupling member 88 is configured by a belt-like rubber plate having predetermined elasticity.

In the driving unit 2C configured as explained above, when the first and second pressure chambers 17 and 18 are opened to the atmosphere, the first and second sliders 21 and 22 are urged by the urging force of the coil spring 23 in directions in which the first and second sliders 21 and 22 separate from each other. For example, as shown in FIGS. 16 and 19, the first and second swinging bodies 82 and 83 are laid flat along the axial direction of the first and second sliders 21 and 22 by the urging force.

That is, when the first and second sliders 21 and 22 are urged in the directions in which the first and second sliders 21 and 22 separate from each other, the fixed end side (the shaft section 84) of the first swinging body 82 is relatively moved to the proximal end side of the guide groove 21b and the fixed end side (the shaft section 85) of the second swinging body 83 is relatively moved to the distal end side of the guide groove 22b. Further, towing forces from the first and second sliders 21 and 22 are transmitted to the fixed end sides of the first and second swinging bodies 82 and 83, whereby the free end sides of the first and second swinging bodies 82 and 83 are towed to each other via the coupling member 88. Consequently, the first and second swinging bodies 82 and 83 are laid flat along the axial direction of the first and second sliders 21 and 22.

The first and second swinging bodies 82 and 83 are laid flat in this way, whereby the respective locking claw sections 86 and 87 are housed between the first and second sliders 21 and 22.

On the other hand, for example, when the air is supplied into the first and second pressure chambers 17 and 18 and the first and second sliders 21 and 22 are moved in directions in which the first and second sliders 21 and 22 approach each other against the urging force of the coil spring 23, as shown in FIGS. 17 and 20, the first and second swinging bodies 82 and 83 are erected in the diameter expansion direction.

That is, when the first and second sliders 21 and 22 are urged in the directions in which the first and second sliders 21 and 22 approach each other, the fixed end side (the shaft section 84) of the first swinging body 82 is moved to a distal end side of the guide groove 21b and the fixed end side (the shaft section 85) of the second swinging body 83 is moved to a proximal end side of the guide groove 22b. When the first and second sliders 21 and 22 further approach, pressing forces from the first and second sliders 21 and 22 are transmitted to the fixed end sides of the first and second swinging bodies 82 and 83. Consequently, the coupling member 88 is elastically deformed in a bow shape. The first and second swinging bodies 82 and 83 are erected in the diameter expansion direction by repulsion due to the elastic deformation of the coupling member 88. The first and second sliders 21 and 22 can be brought close to each other to positions where end portions of the protrusions for guide 21a and 22a opposed to each other come into contact with each other. When the first and second sliders 21 and 22 approach most in this way, the first and second swinging bodies 82 and 83 are erected in a state in which the first and second swinging bodies 82 and 83 are expanded in diameter most.

According to such displacement in the diameter expansion direction of the first and second swinging bodies 82 and 83, the locking claw sections 86 and 87 are displaced in the diameter expansion direction and brought into sliding contact with a target object such as the inner wall of the pipe 50. The slider unit 70 is prohibited from moving in the pipe 50 or the like by the sliding contact of the locking claw sections 86 and 87.

More specifically, the locking claw section 86 of the brake 80, which inclines with a predetermined angle of elevation toward a proximal end side of the slider unit 70, is brought into sliding contact with, for example, the inner wall of the pipe 50, whereby the slider unit 70 is prohibited from moving to a proximal end side (a retracting side). On the other hand, the locking claw section 87, which inclines with a predetermined angle of elevation toward a distal end side of the slider unit 70 is brought into sliding contact with, for example, the inner wall of the pipe 50, whereby the slider unit 70 is prohibited from moving to a distal end side (an advancing side).

In this case, the fixed end sides (the respective shaft sections 84 and 85) of the first and second swinging bodies 82 and 83 are supported by the slider unit 70 via the guide grooves 21b and 22b. Therefore, even when the first and second sliders 21 and 22 start movement in the directions in which the first and second sliders 21 and 22 approach each other, pressing forces from the first and second sliders 21 and 22 are not immediately transmitted to the first and second swinging bodies 82 and 83. In other words, clearance is provided between the first and second sliders 21 and 22 and the first and second swinging bodies 82 and 83 by the respective guide grooves 21b and 22b. Therefore, as shown in FIG. 21, even when the driving unit 2C of the present embodiment moves forward and backward in the bent pipe 50, in a range in which the respective guide grooves 21b and 22b allow movement of the respective shaft sections 84 and 85, it is possible to relatively displace the first and second sliders 21 and 22 without causing the first and second swinging bodies 82 and 83 to perform a diameter expansion operation.

Note that projecting length of the respective protrusions for guide 21a and 22a, length of the respective guide grooves 21b and 22b, length of the respective locking claw sections 86 and 87, and the like are tuned as appropriate according to, for example, an inner diameter of the pipe 50 to which the driving unit 2C is applied.

According to the embodiment explained above, in addition to the effects explained in the first embodiment, by adopting a configuration in which the locking claw sections 86 and 87 are brought into sliding contact with the target object such as the pipe 50, it is possible to surely retain the slider unit 70 in the pipe 50. It is possible to more surely transmit propulsion to the guide tube 5.

In the present embodiment, two or more kinds of locking claw sections having different projecting lengths can also be respectively provided as contact members with respect to the first and second swinging bodies 82 and 83.

Figure 22:
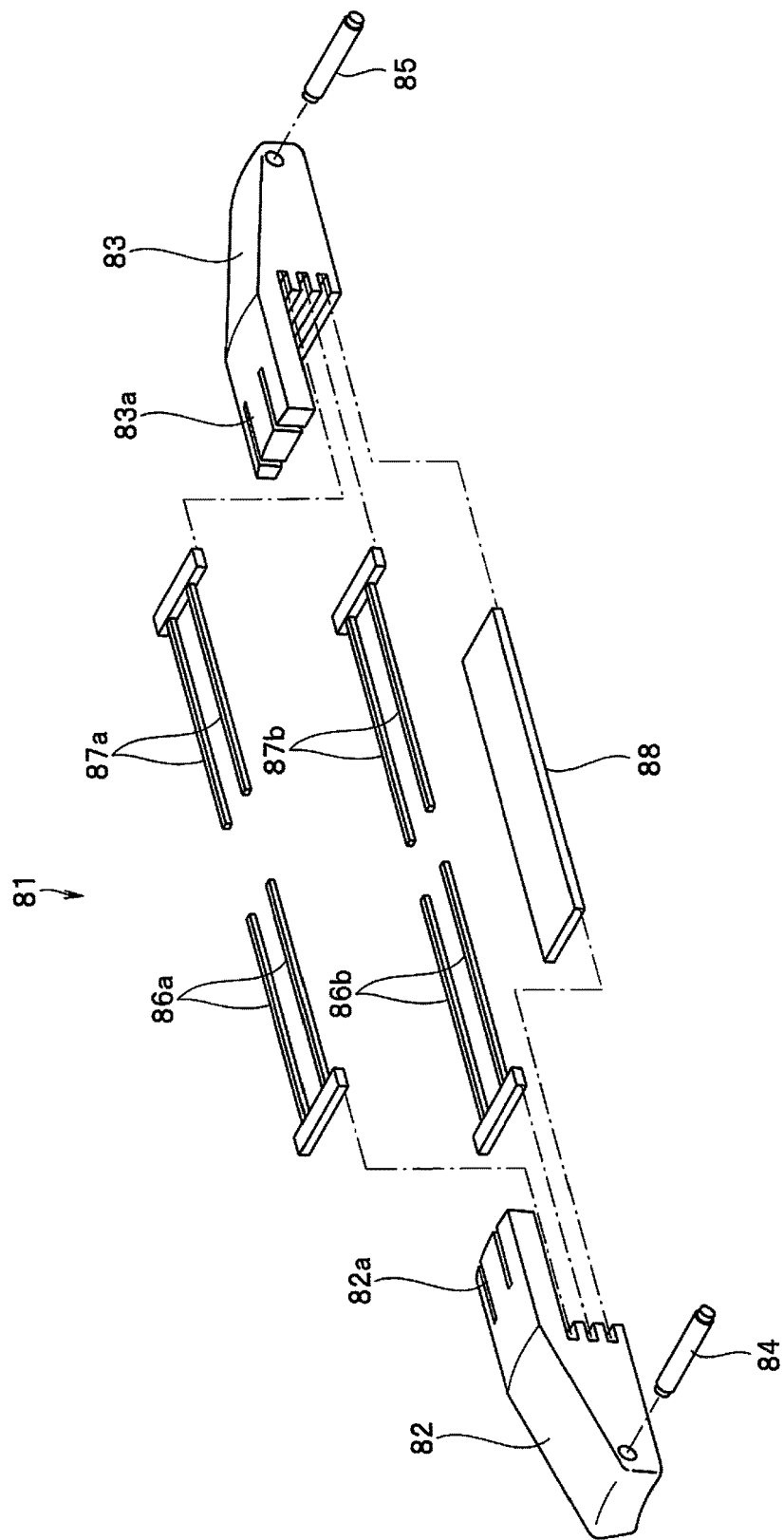
FIG. 22 relates to a first modification of the fourth embodiment and is an exploded perspective view showing a main part of a brake member.
Figure 23:
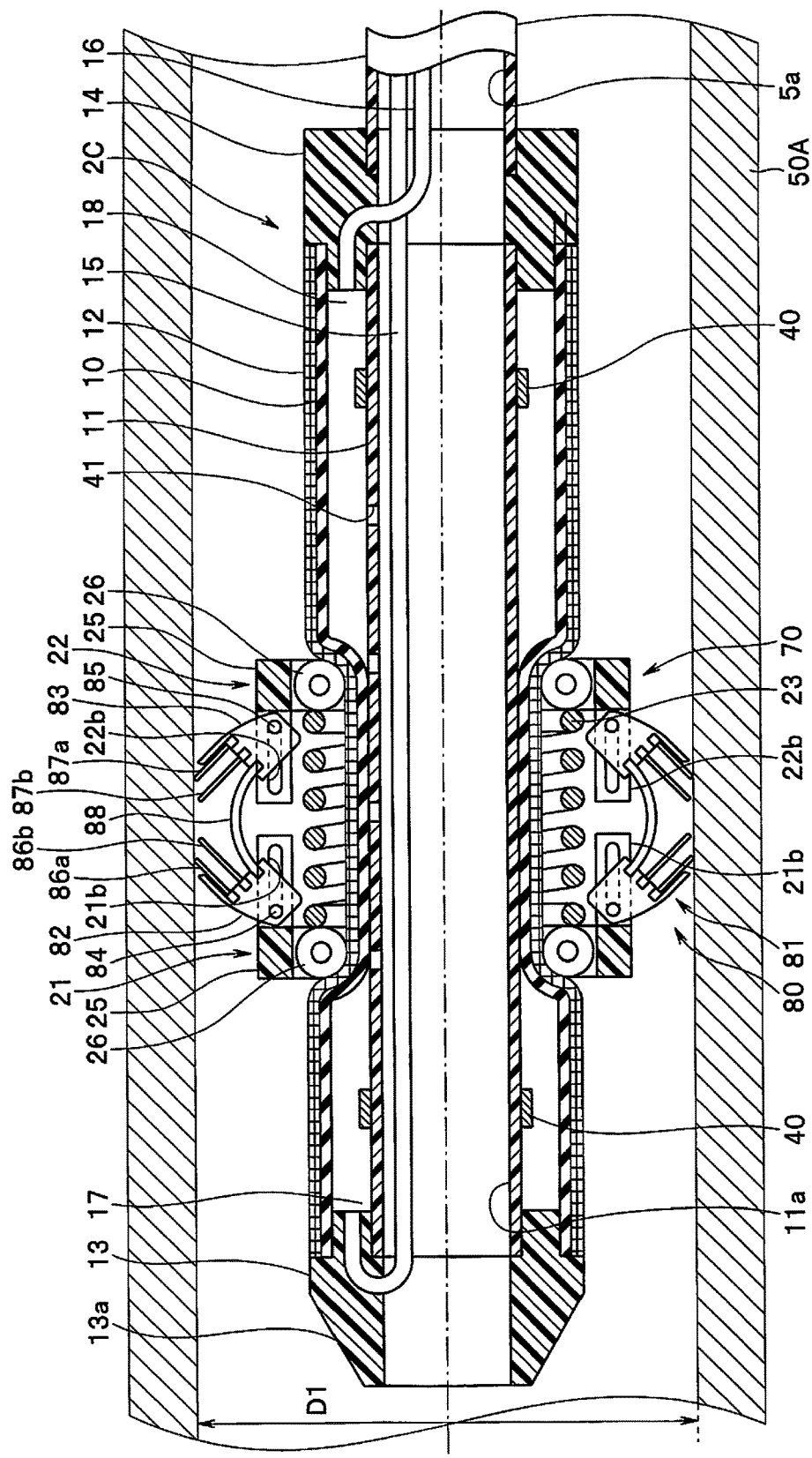
FIG. 23 relates to the first modification and is a main part sectional view schematically showing a driving unit at the time when a brake is in the actuated state in the pipe.
Figure 24:
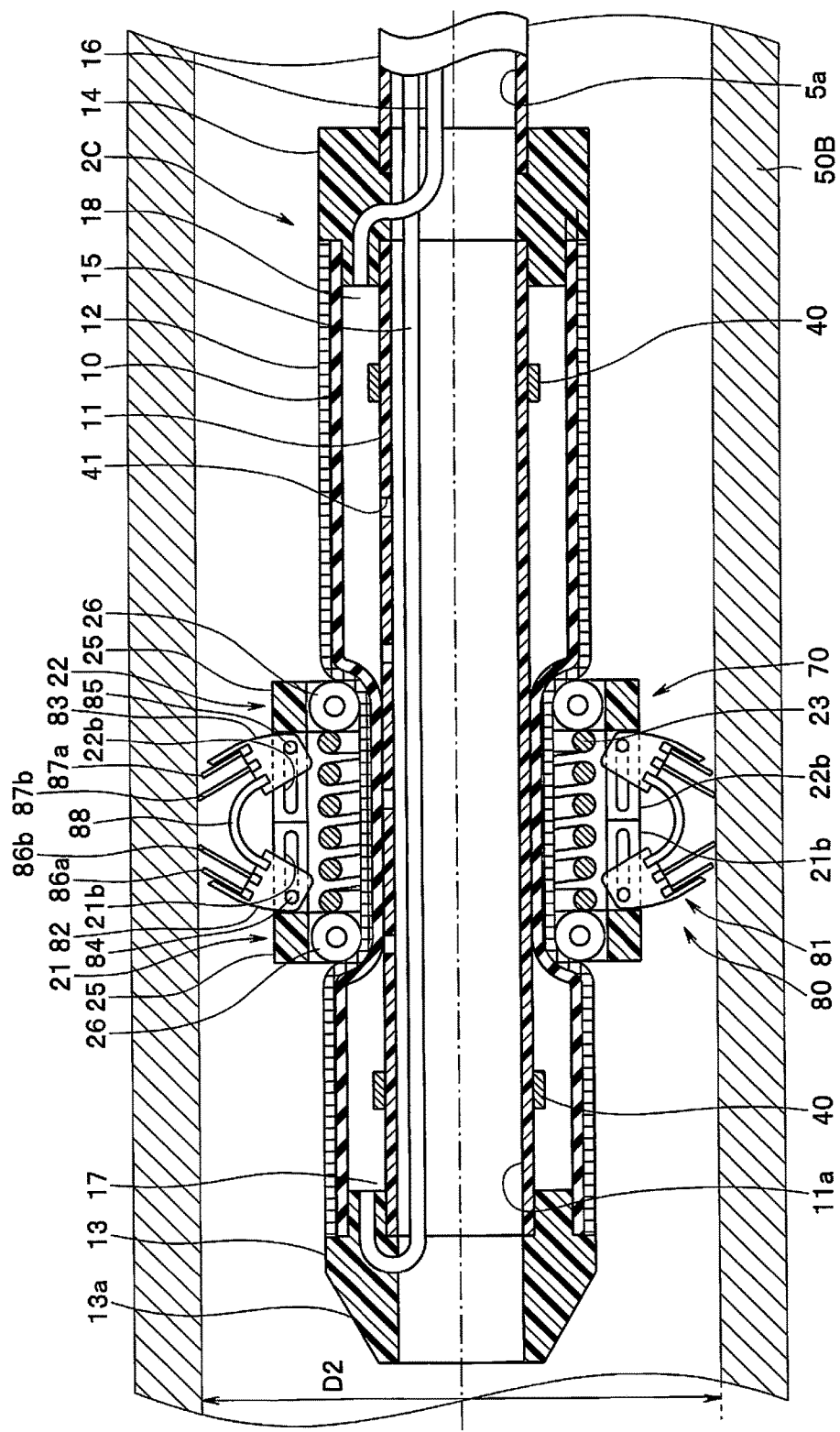
FIG. 24 relates to the first modification and is a main part sectional view schematically showing the driving unit at the time when the brake is in the actuated state in the pipe.

For example, in a modification shown in FIG. 22 to FIG. 24, a first locking claw section 86a and a second locking claw section 86b having different projecting lengths are provided on the free end side of the first swinging body 82. A first locking claw section 87a and a second locking claw section 87b having different projecting lengths are provided on the free end side of the second swinging body 83.

Of the first and second locking claw sections 86a and 86b, the first locking claw section 86a provided on an outer side in the diameter expansion direction of the first swinging body 82 is set relatively shorter than the second locking claw section 86b.

In this case, the first locking claw section 86a matches, for example, a pipe 50A having an inner diameter D1. Length of the first locking claw section 86a is set such that, for example, as shown in FIG. 23, the first locking claw section 86a comes into sliding contact with an inner circumferential surface of the pipe 50A in a diameter expansion position before the first swinging body 82 reaches a maximum diameter expansion position.

The second locking claw section 86b matches, for example, a pipe 50B having an inner diameter D2 (D2>D1). Length of the second locking claw section 86b is set such that, for example, as shown in FIG. 24, the second locking claw section 86b comes into sliding contact with an inner circumferential surface of the pipe 50B when the first swinging body 82 reaches the maximum diameter expansion position.

Similarly, of the first and second locking claw sections 87a and 87b, the first locking claw section 87a provided on an outer side in the diameter expansion direction of the second swinging body 83 is set relatively shorter than the second locking claw section 87b.

In this case, the first locking claw section 87a matches, for example, the pipe 50A having the inner diameter D1. Length of the first locking claw section 87a is set such that, for example, as shown in FIG. 23, the first locking claw section 87a comes into sliding contact with the inner circumferential surface of the pipe 50A in a diameter expansion position before the first swinging body 83 reaches a maximum diameter expansion position.

The second locking claw section 87b matches, for example, the pipe 50B having the inner diameter D2 (D2>D1). Length of the second locking claw section 87b is set such that, for example, as shown in FIG. 24, the second locking claw section 87b comes into sliding contact with the inner circumferential surface of the pipe 50B when the second swinging body 83 reaches the maximum diameter expansion position.

With the configuration explained above, for example, even in a conduit or the like in which an inner diameter of a pipe changes halfway, it is possible to surely retain the slider unit 70. It is possible to more surely transmit propulsion to the guide tube 5.

Figure 25:
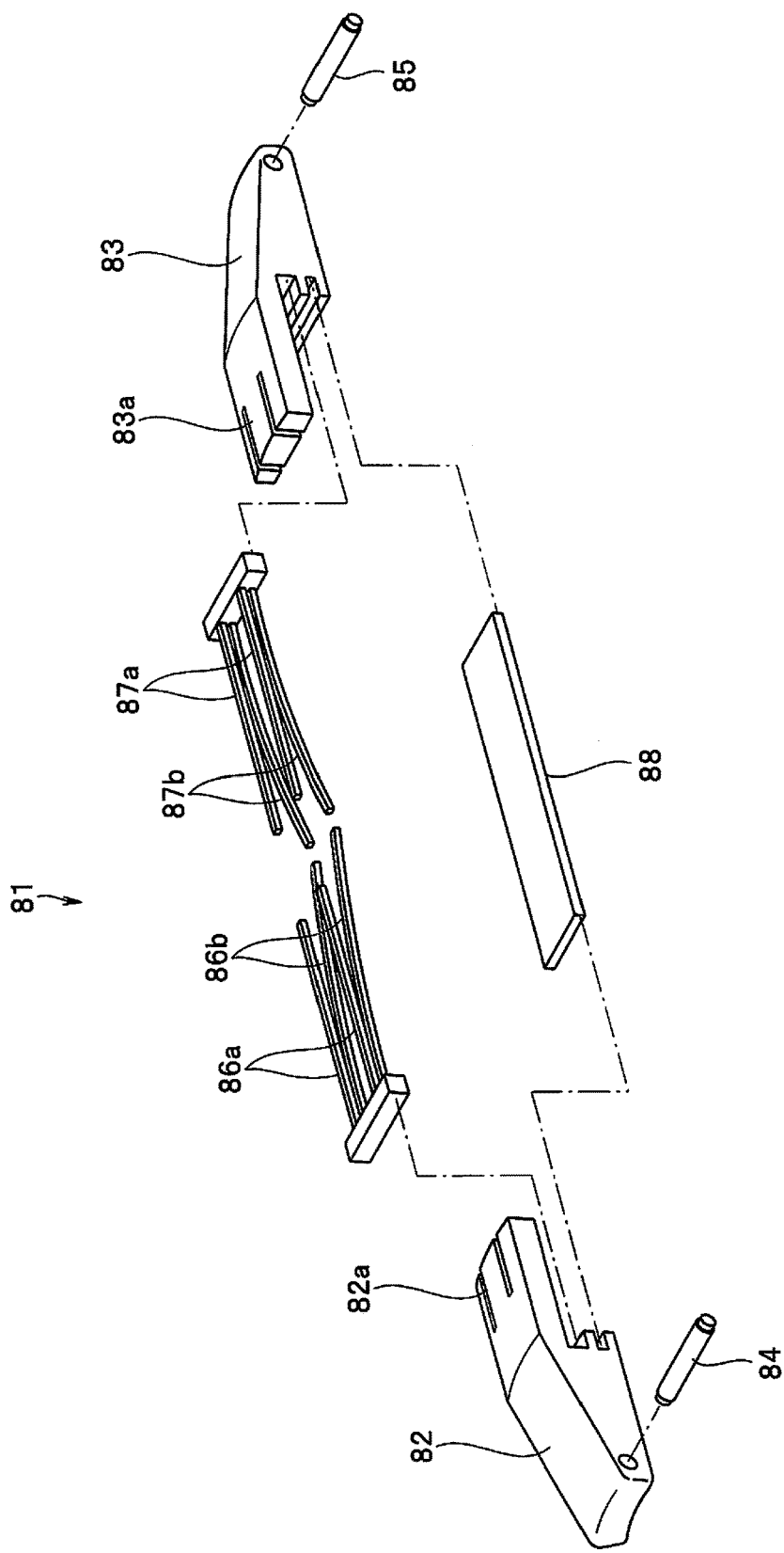
FIG. 25 relates to a second modification of the fourth embodiment and is an exploded perspective view showing a main part of a brake member.
Figure 26:
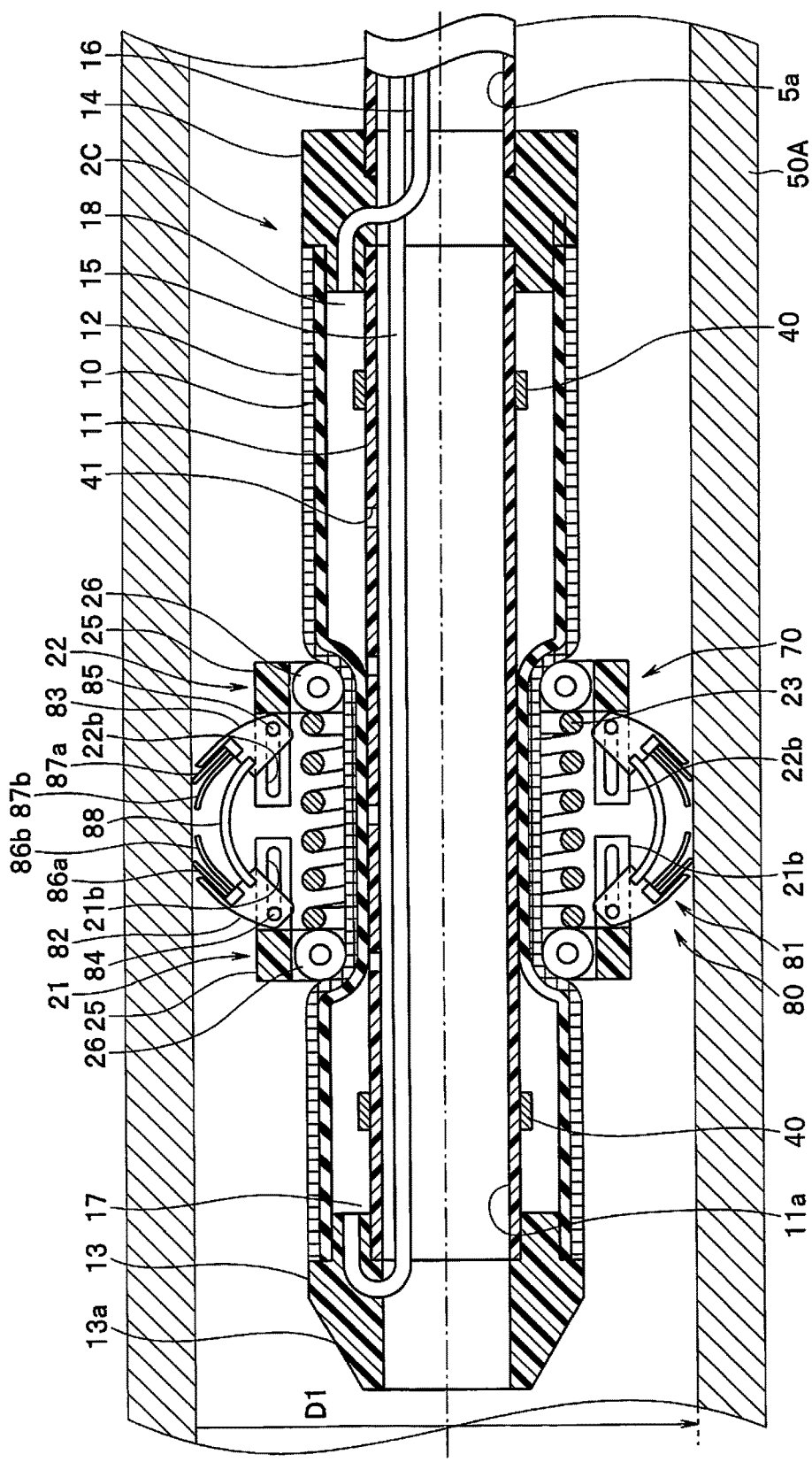
FIG. 26 relates to the second modification and is a main part sectional view schematically showing a driving unit at the time when a brake is in the actuated state in the pipe.
Figure 27:
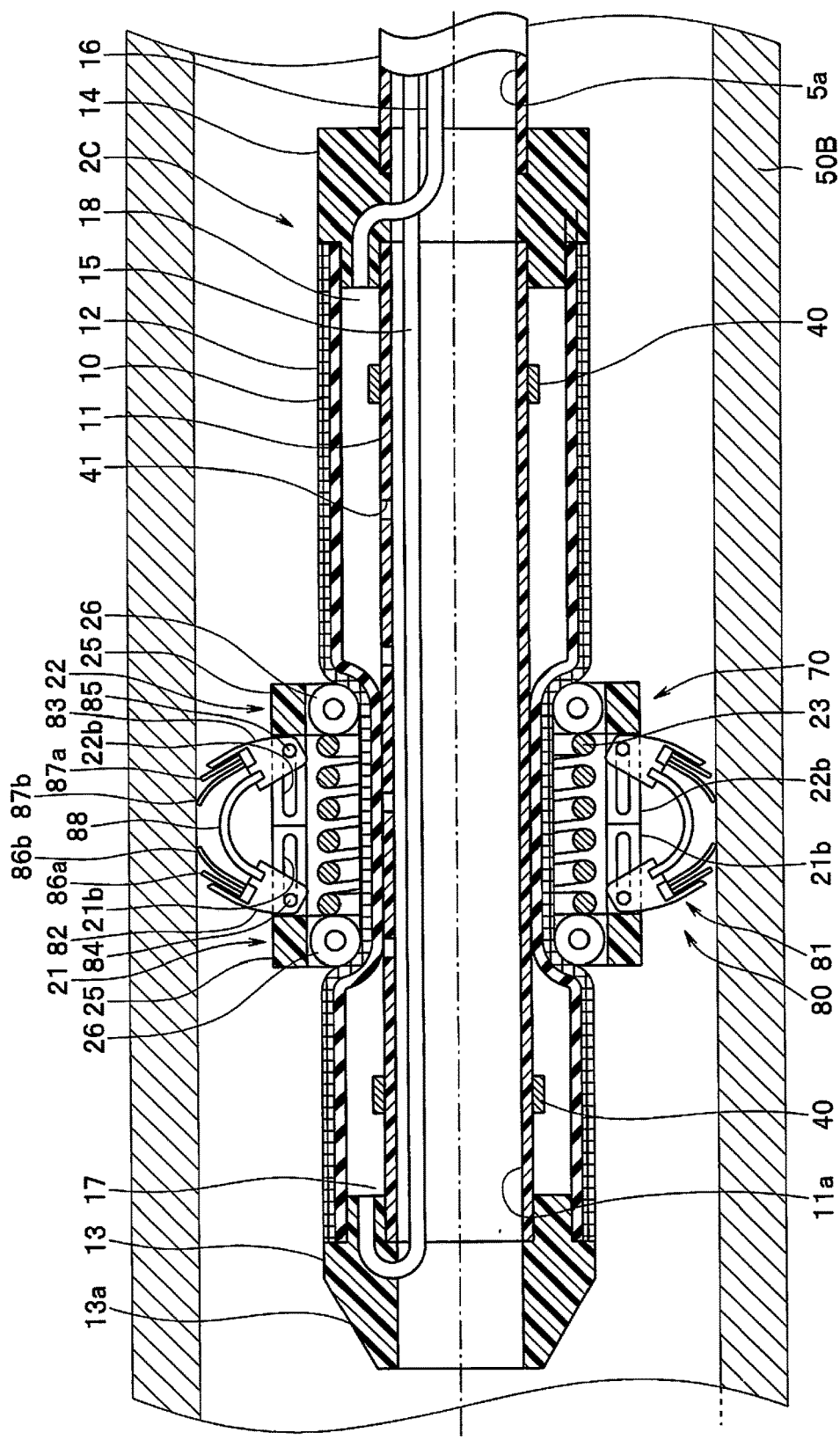
FIG. 27 relates to the second modification and is a main part sectional view schematically showing the driving unit at the time when the brake is in the actuated state in the pipe.

For example, as shown in FIG. 25 to FIG. 27, it is also possible to bend and form the second locking claw sections 86b and 87b in a bow shape or form the second locking claw sections 86b and 87b in a shape in which only distal end portions are bent. If the second locking claw sections 86b and 87b are formed in this way, it is possible to bring the second locking claw sections 86b and 87b into sliding contact with the pipes 50A and 50B having different inner diameters while disposing the second locking claw sections 86b and 87b in substantially the same positions as the first locking claw sections 86a and 87a. It is possible to bring the second locking claw sections 86b and 87b into sliding contact with the pipes 50A and 50B having the different inner diameters at angles for most easy retention.

In the present embodiment, it is also possible to configure the locking claw sections 86 and 87 to be replaceable with respect to the first and second swinging bodies 82 and 83.

Figure 28:
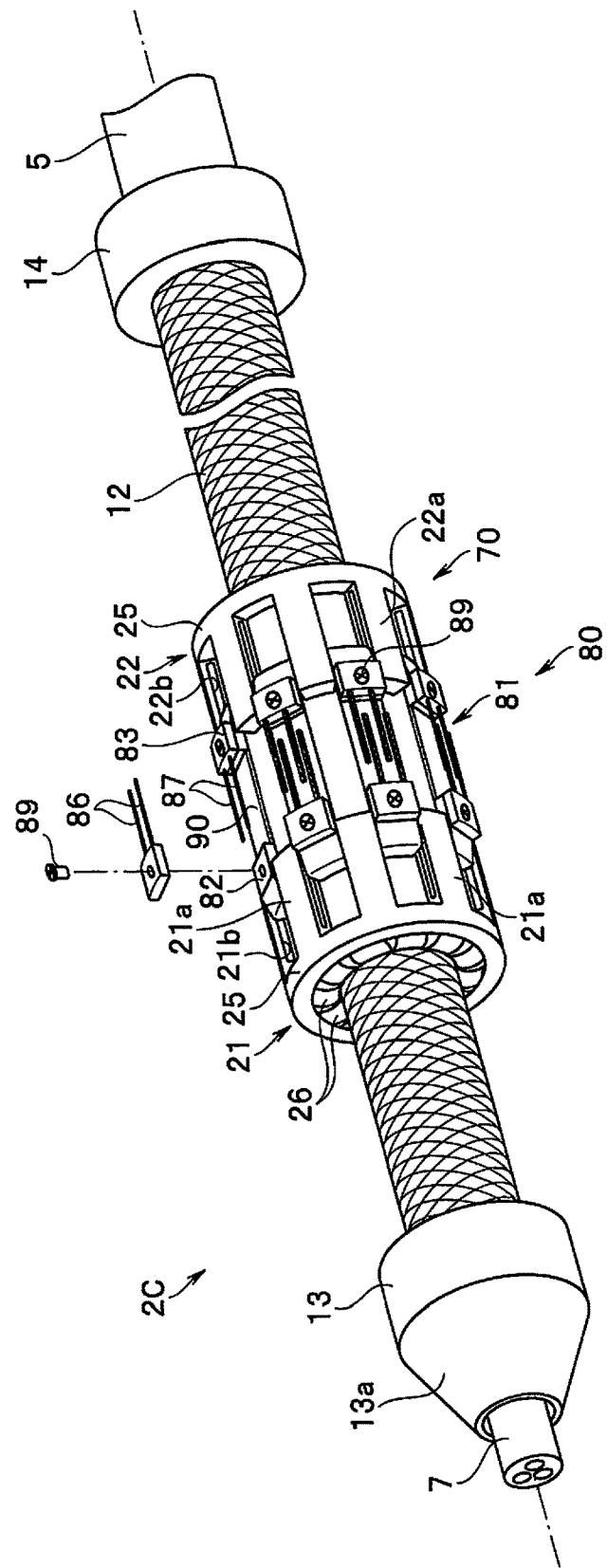
FIG. 28 relates to a third modification of the fourth embodiment and is a perspective view of a driving unit.
Figure 29:
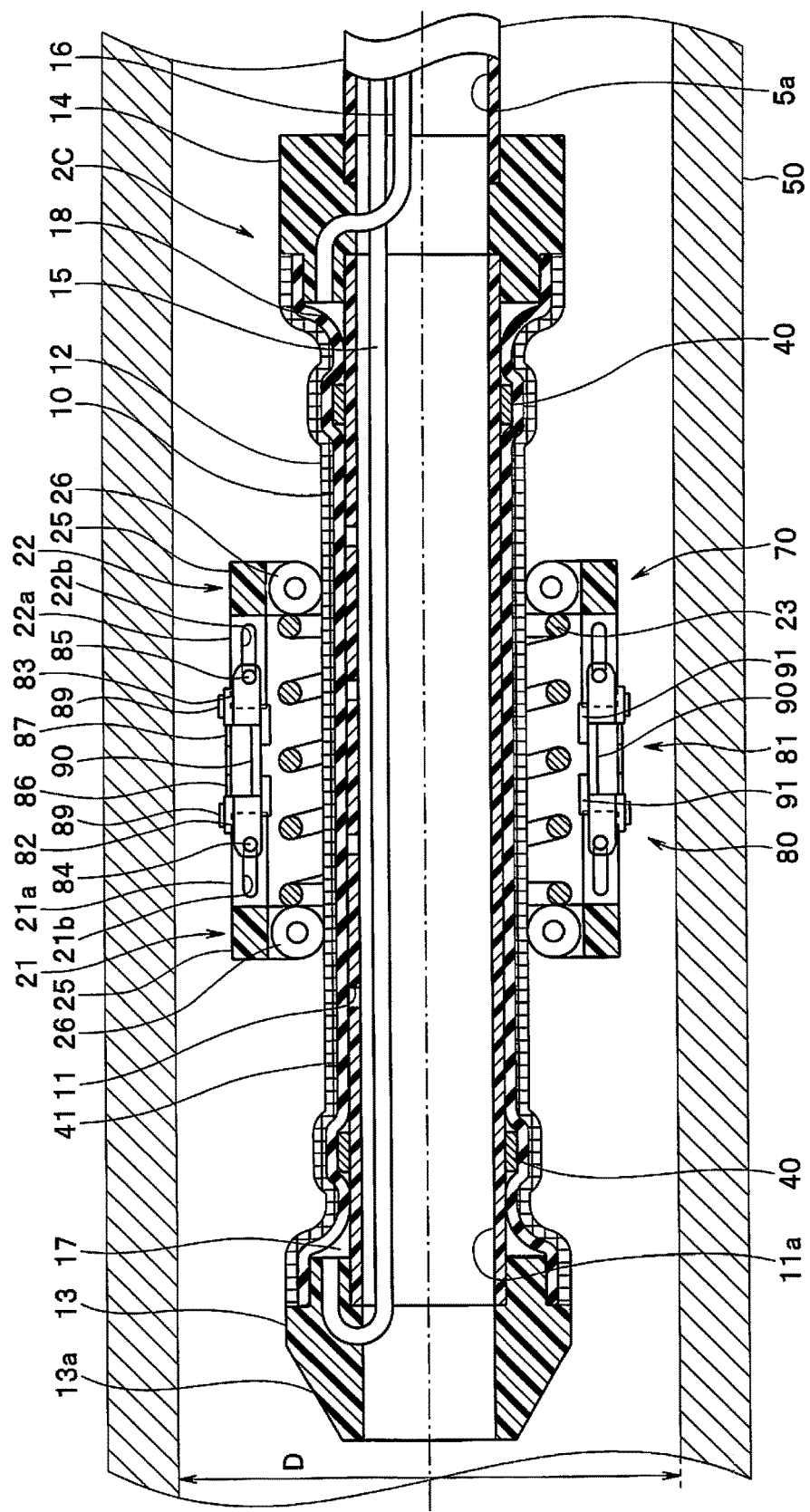
FIG. 29 relates to the third modification and is a main part sectional view schematically showing the driving unit at the time when a brake is in the unactuated state in the pipe.
Figure 30:
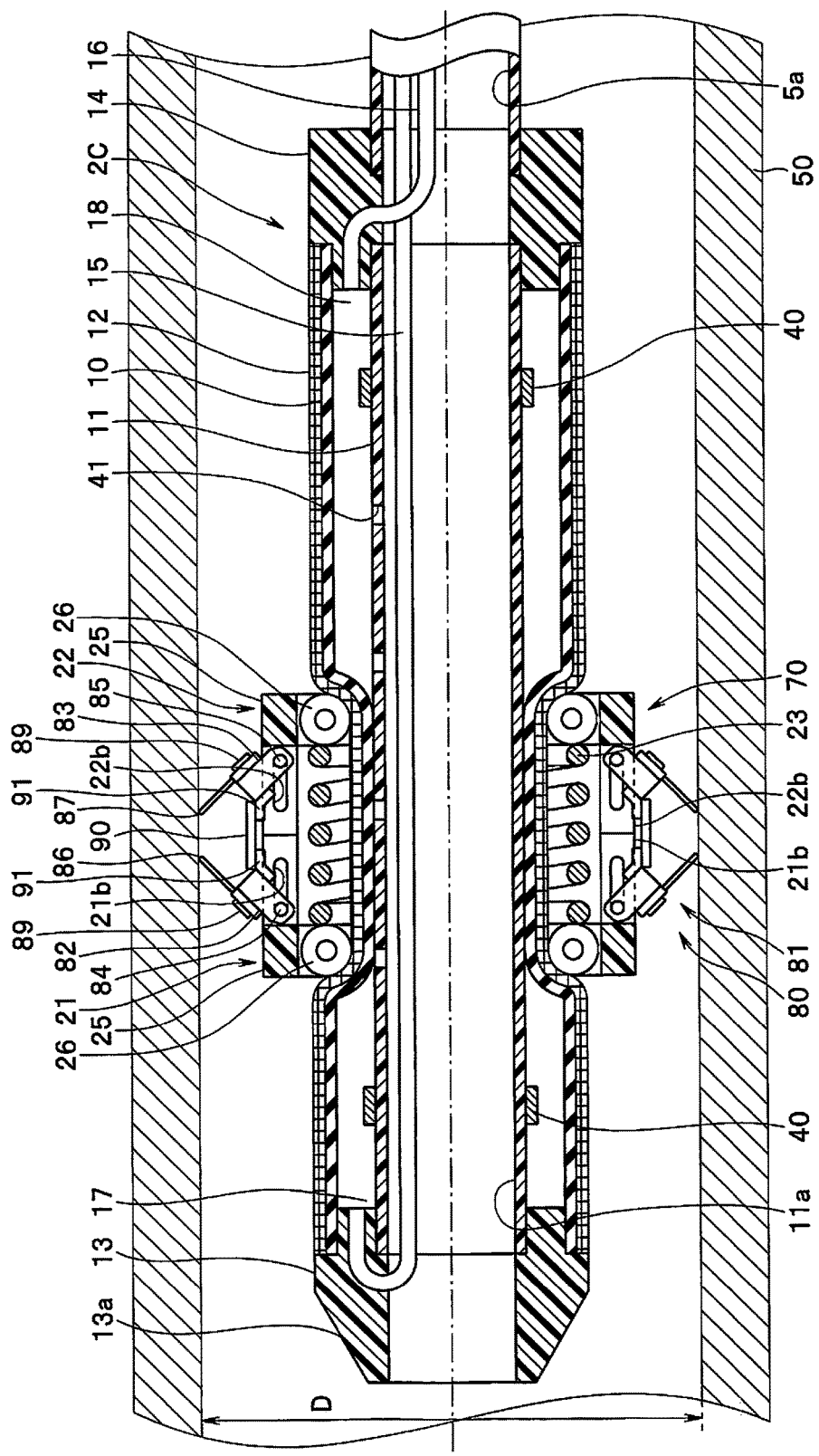
FIG. 30 relates to the third modification and is a main part sectional view schematically showing the driving unit at the time when the brake is in the actuated state in the pipe.

For example, in a modification shown in FIG. 28 to FIG. 30, the locking claw sections 86 and 87 are detachably fixed to the first and second swinging bodies 82 and 83 using screws 89.

Note that, in this modification, for example, as shown in FIGS. 29 and 30, a rigid tabular coupling member 90 is adopted. The coupling member 90 is coupled to the respective free end sides of the first and second swinging bodies 82 and 83 via a sheet-like elastic body 91.

With the configuration explained above, the locking claw sections 86 and 87 having optimum length can be used according to the inner diameter D of the applied pipe 50. Therefore, it is possible to surely retain the slider unit 70 in the pipe 50. It is possible to more surely transmit propulsion to the guide tube 5.

Figure 31:
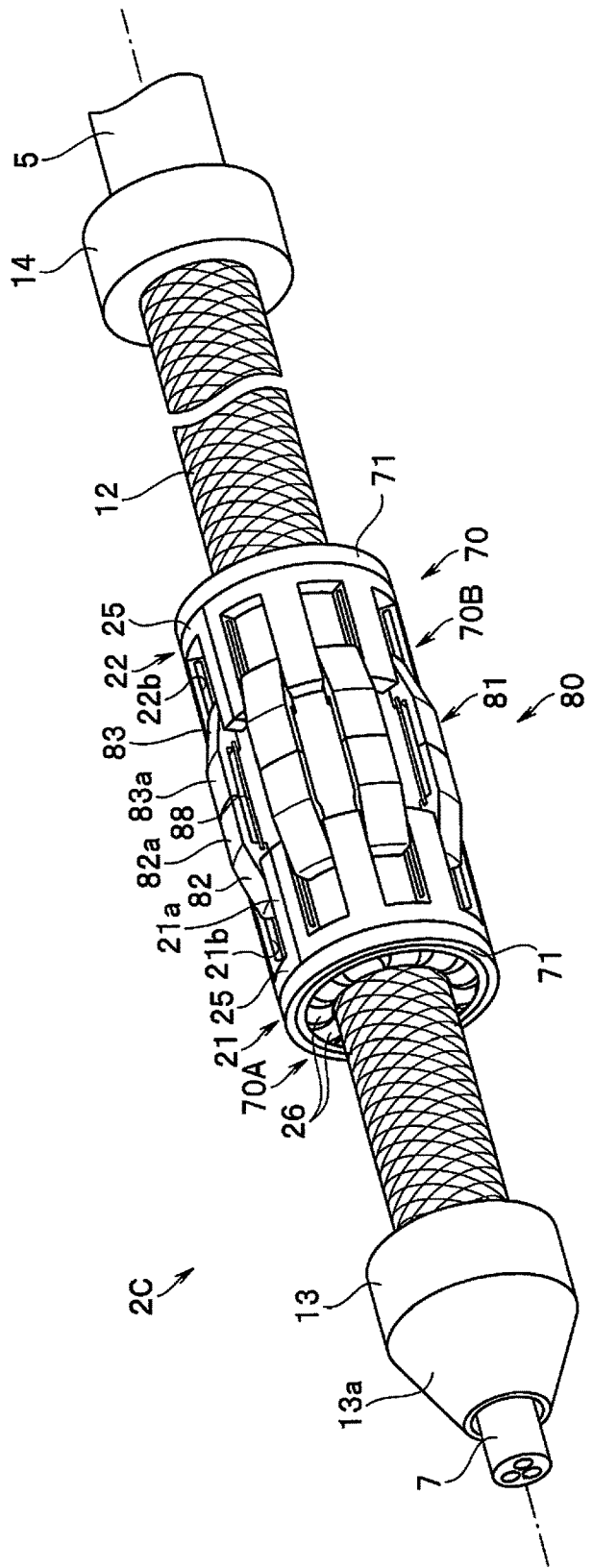
FIG. 31 relates to a fourth modification of the fourth embodiment and is a perspective view showing main parts of a slider unit and a brake.
Figure 32:
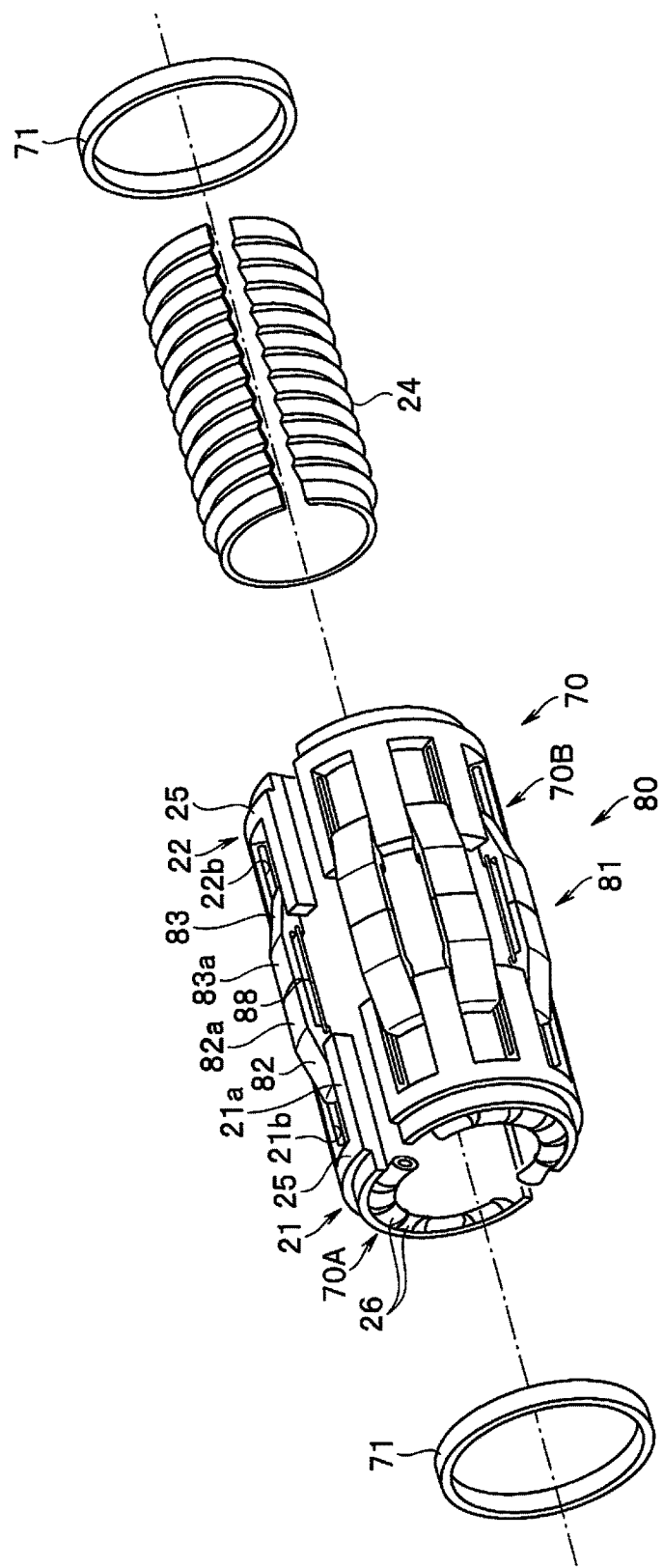
FIG. 32 relates to the fourth modification and is an exploded perspective view showing the main parts of the slider unit and the brake.

As shown in FIGS. 31 and 32, the slider unit 70 may be divided into two to be capable of being assembled such that the slider unit 70 can be easily attached to and detached from the outer circumference side of the mesh tube 12 (the elastic tube 10 and the flexible tube 11). In an example shown in FIGS. 31 and 32, the slider unit 70 is divided into a first slider unit divided body 70A and a second slider unit divided body 70B along the longitudinal direction. A bellows member 24 having a spring property is provided on an inside of the slider unit 70 instead of the coil spring 23. A notch for facilitating attachment and detachment to and from the outer circumference side of the mesh tube 12 (the elastic tube 10 and the flexible tube 11) is provided in the bellows member 24 along the longitudinal direction.

In this modification, the bellows member 24 is attached to the outer circumference side of the mesh tube 12 by deforming to expand and open the notch. Thereafter, the first and second slider unit divided bodies 70A and 70B are bonded to cover the bellows member 24 from both sides. Fixing rings 71 are fixed to both ends of the bonded first and second slider unit divided bodies 70A and 70B, whereby the bonded first and second slider unit divided bodies 70A and 70B are inseparably retained. Note that both ends of the slider unit 70 and respective fixing rings 71 respectively have male thread and female thread shapes such that both the ends of the slider unit 70 and the respective fixing rings 71 can be fixed in a screw shape. Alternatively, besides, both the ends of the slider unit 70 and the respective fixing rings 71 can also be fixed by set screws from a side.

Figure 33:
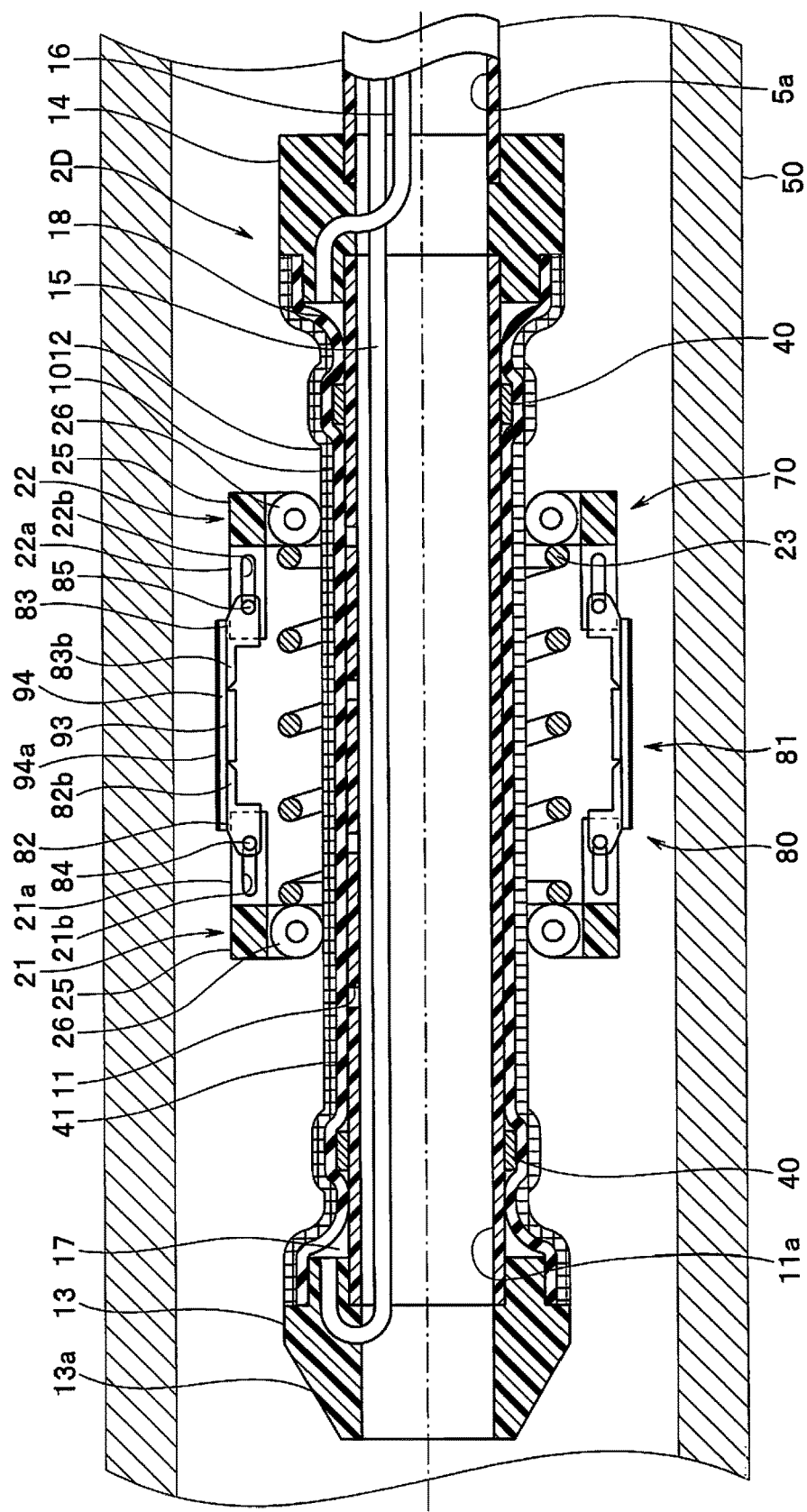
FIG. 33 relates to a fifth embodiment of the present invention and is a main part sectional view schematically showing a driving unit at a time when a brake is in an unactuated state in a pipe.
Figure 34:
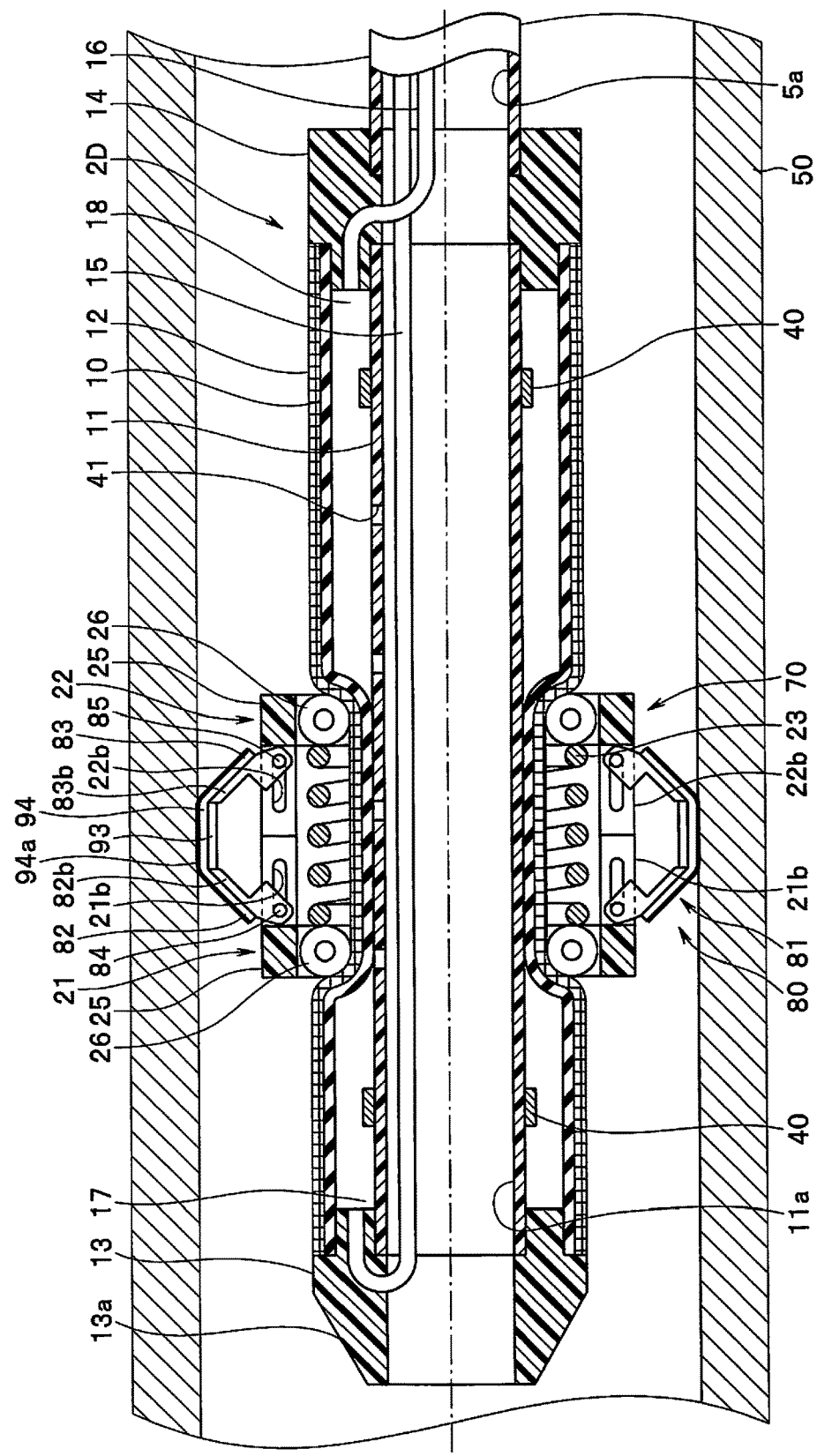
FIG. 34 relates to the fifth embodiment and is a main part sectional view schematically showing the driving unit at a time when the brake is in an actuated state in the pipe.

FIG. 33 and FIG. 34 relate to a fifth embodiment of the present invention. FIG. 33 is a main part sectional view schematically showing a driving unit at a time when a brake is in an unactuated state in a pipe. FIG. 34 is a main part sectional view schematically showing the driving unit at a time when the brake is in an actuated state in the pipe. Note that the present embodiment is mainly different from the fourth embodiment in that a brake section provided in a slider unit is configured by a link mechanism. Otherwise, components same as the components in the fourth embodiment are denoted by the same reference numerals and signs as appropriate and explanation of the components is omitted.

As shown in FIGS. 33 and 34, in a driving unit 2D of the present embodiment, a first arm section 82b capable of swinging integrally with the first swinging body 82 is provided on a proximal end side (the free end side) of the first swinging body 82.

A second arm section 83b capable of swinging integrally with the second swinging body 83 is provided on a distal end side (the free end side) of the second swinging body 83.

A brake plate 93 functioning as a contact member having rigidity is provided between the first arm section 82b and the second arm section 83b.

A series of sheet material 94 having elasticity is stuck to surfaces of the first arm section 82b, the brake plate 93, and the second arm section 83b. The first arm section 82b, the brake plate 93, and the second arm section 83b are coupled via the sheet material 94, whereby the brake plate 93 is capable of bending to be displaced with respect to the first arm section 82b and the second arm section 83b.

Further, an oblique bristle 94a functioning as a friction member for increasing frictional resistance at a time of contact with the inner circumferential surface of the pipe 50 is provided on a surface of the sheet material 94. Shapes having angles are alternately disposed or mixed in the oblique bristle 94a such that the oblique bristle 94a can be retained in different directions (forward and backward).

Note that, rather than providing the oblique bristle, the surface of the sheet material 94 may be roughened to generate friction or a rubber sheet may be stuck to the surface of the sheet material 94.

In the driving unit 2D configured as explained above, when the first and second pressure chambers 17 and 18 are opened to the atmosphere, the first and second sliders 21 and 22 are urged by the urging force of the coil spring 23 in directions in which the first and second sliders 21 and 22 separate from each other. For example, as shown in FIG. 33, the first and second swinging bodies 82 and 83 are laid flat along the axial direction of the first and second sliders 21 and 22 by the urging force and the first arm section 82b, the brake plate 93, and the second arm section 83b are located in substantially linearly arranged retracted positions by the urging force.

On the other hand, for example, when the air is supplied into the first and second pressure chambers 17 and 18 and the first and second sliders 21 and 22 are moved in directions in which the first and second sliders 21 and 22 approach each other against the urging force of the coil spring 23, for example, as shown in FIG. 34, the first and second arm sections 82b and 83b are displaced in the diameter expansion direction together with the first and second swinging bodies 82 and 83 while moving the brake plate 93 in the diameter expansion direction. Consequently, the brake plate 93 is brought into sliding contact with the inner circumferential surface of the pipe 50 via the sheet material 94.

According to the embodiment explained above, it is possible to achieve effects substantially the same as the effects in the first embodiment.

In the present embodiment, the brake member 81 can also be configured by a link mechanism having another configuration.

Figure 35:
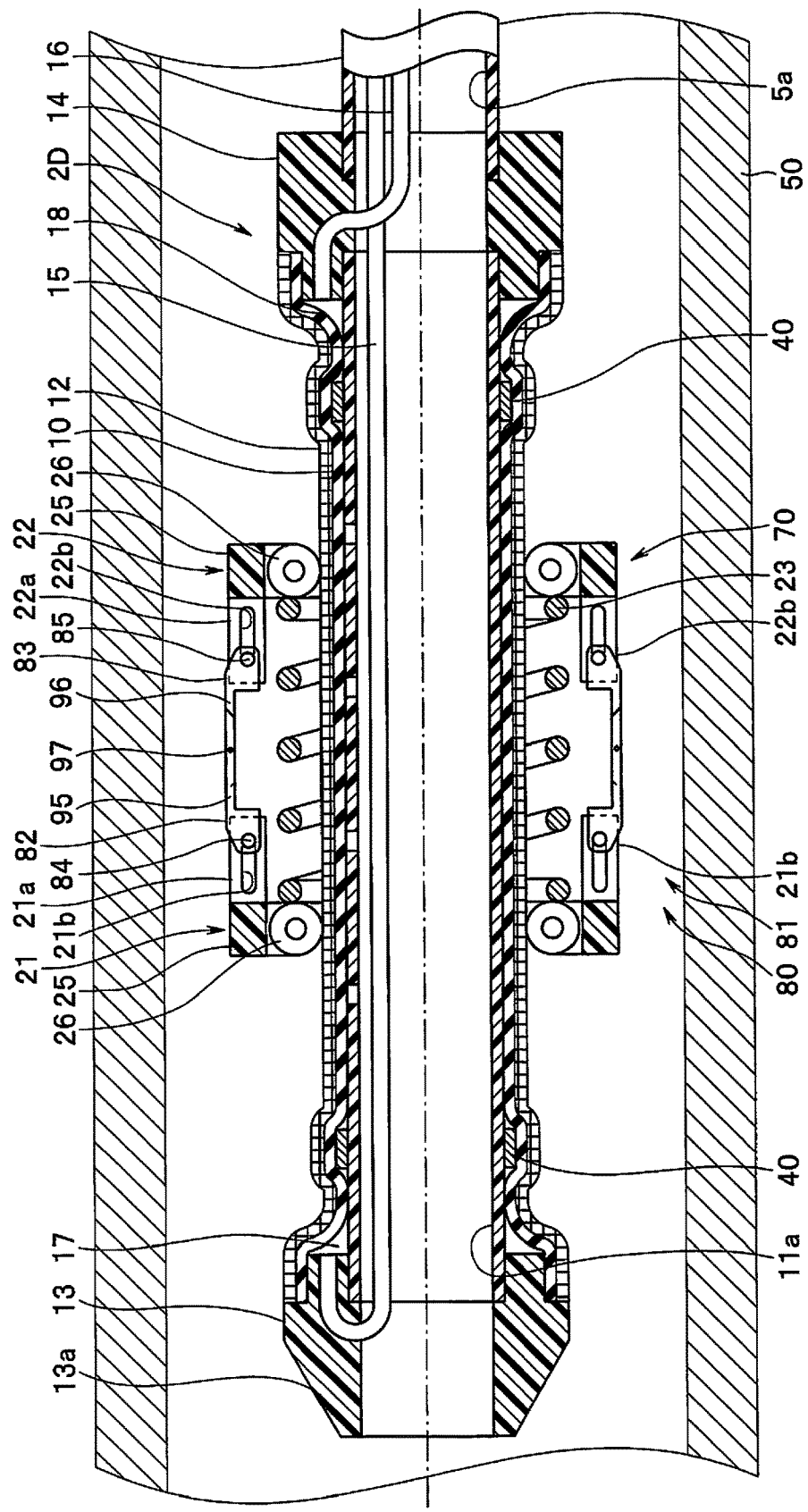
FIG. 35 relates to a first modification of the fifth embodiment and is a main part sectional view schematically showing a driving unit at the time when a brake is in the unactuated state in the pipe.
Figure 36:
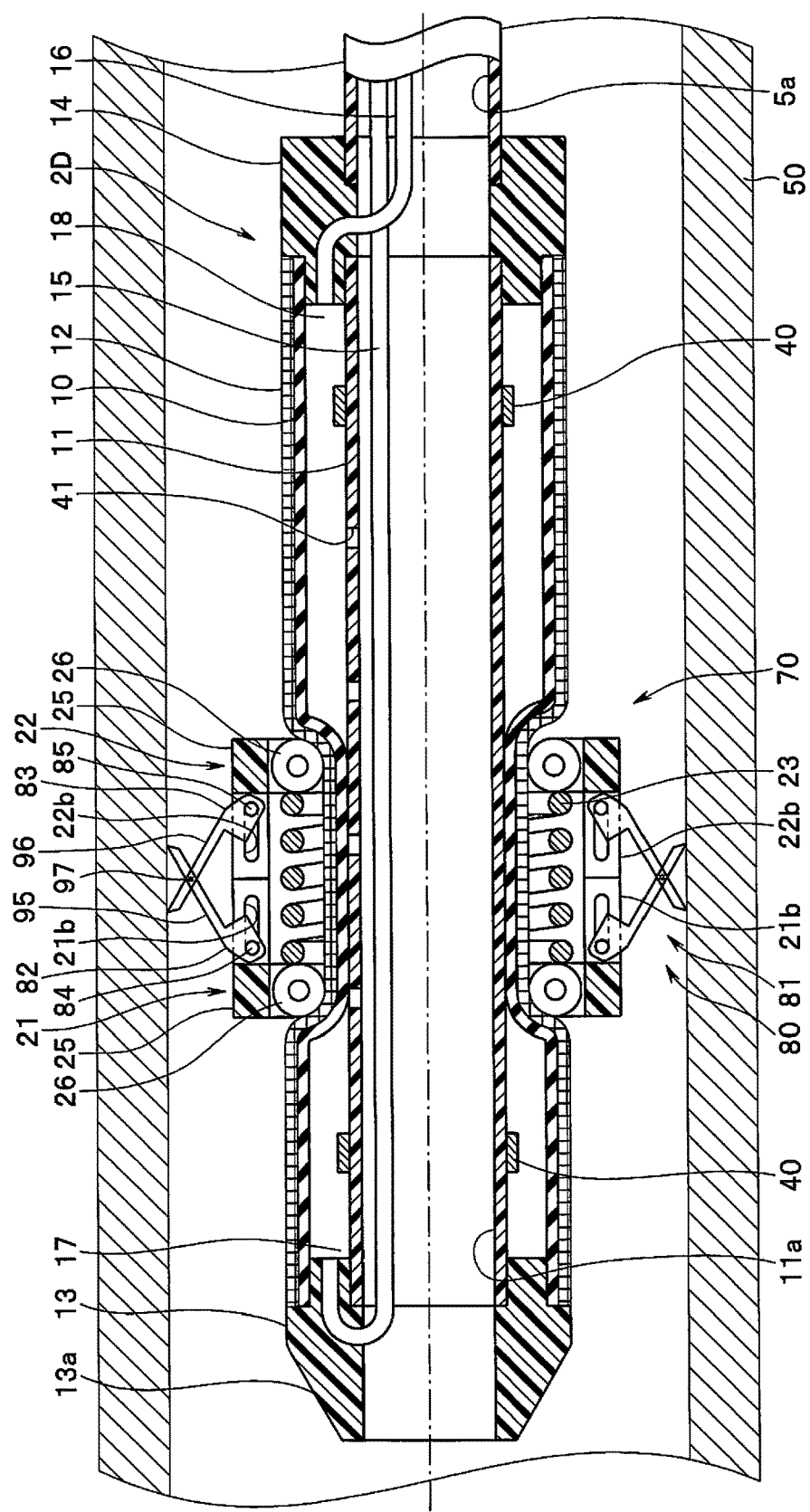
FIG. 36 relates to the first modification and is a main part sectional view schematically showing the driving unit at the time when the brake is in the actuated state in a pipe.

For example, in a modification shown in FIGS. 35 and 36, a locking claw section 95 functioning as a contact member capable of swinging integrally with the first swinging body 82 is provided on the free end side of the first swinging body 82. A locking claw section 96 functioning as a contact member capable of swinging integrally with the second swinging body 83 is provided on the free end side of the second swinging body 83.

Further, halfway parts of the respective locking claw sections 95 and 96 provided in the first and second swinging bodies 82 and 83 opposed to each other are coupled via a shaft section 97. Distal ends of the respective locking claw sections 95 and 96 are obliquely set and formed in a shape easily fixed to (caught by) a pipe.

In the configuration explained above, it is possible to achieve action and effects substantially the same as the action and effects in the embodiments explained above.

That is, when the first and second pressure chambers 17 and 18 are opened to the atmosphere, the first and second sliders 21 and 22 are urged by the urging force of the coil spring 23 in directions in which the first and second sliders 21 and 22 separate from each other. For example, as shown in FIG. 35, the first and second swinging bodies 82 and 83 are turned by the urging force in a laying-flat direction around the shaft section 97 together with the locking claw sections 95 and 96.

On the other hand, for example, when the air is supplied into the first and second pressure chambers 17 and 18 and the first and second sliders 21 and 22 are moved in directions in which the first and second sliders 21 and 22 approach each other against the urging force of the coil spring 23, for example, as shown in FIG. 36, the first and second arm sections 82b and 83b are turned in the diameter expansion direction around the shaft section 97 together with the locking claw sections 95 and 96. Consequently, the respective locking claw sections 95 and 96 are brought into sliding contact with an inner circumferential surface of the pipe.

Figure 37:
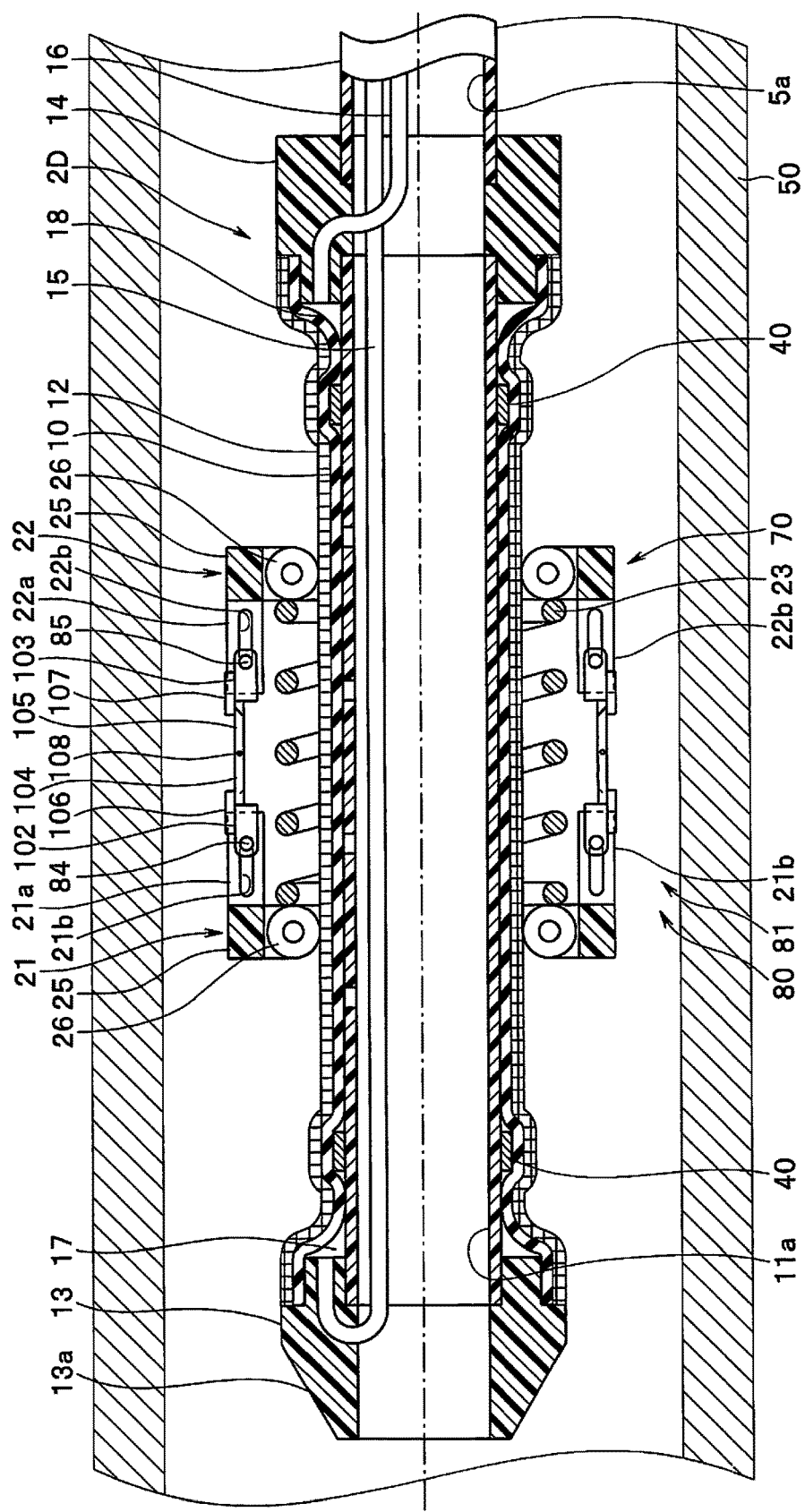
FIG. 37 relates to a second modification of the fifth embodiment and is a main part sectional view schematically showing a driving unit at the time when the brake is in the unactuated state in the pipe.
Figure 38:
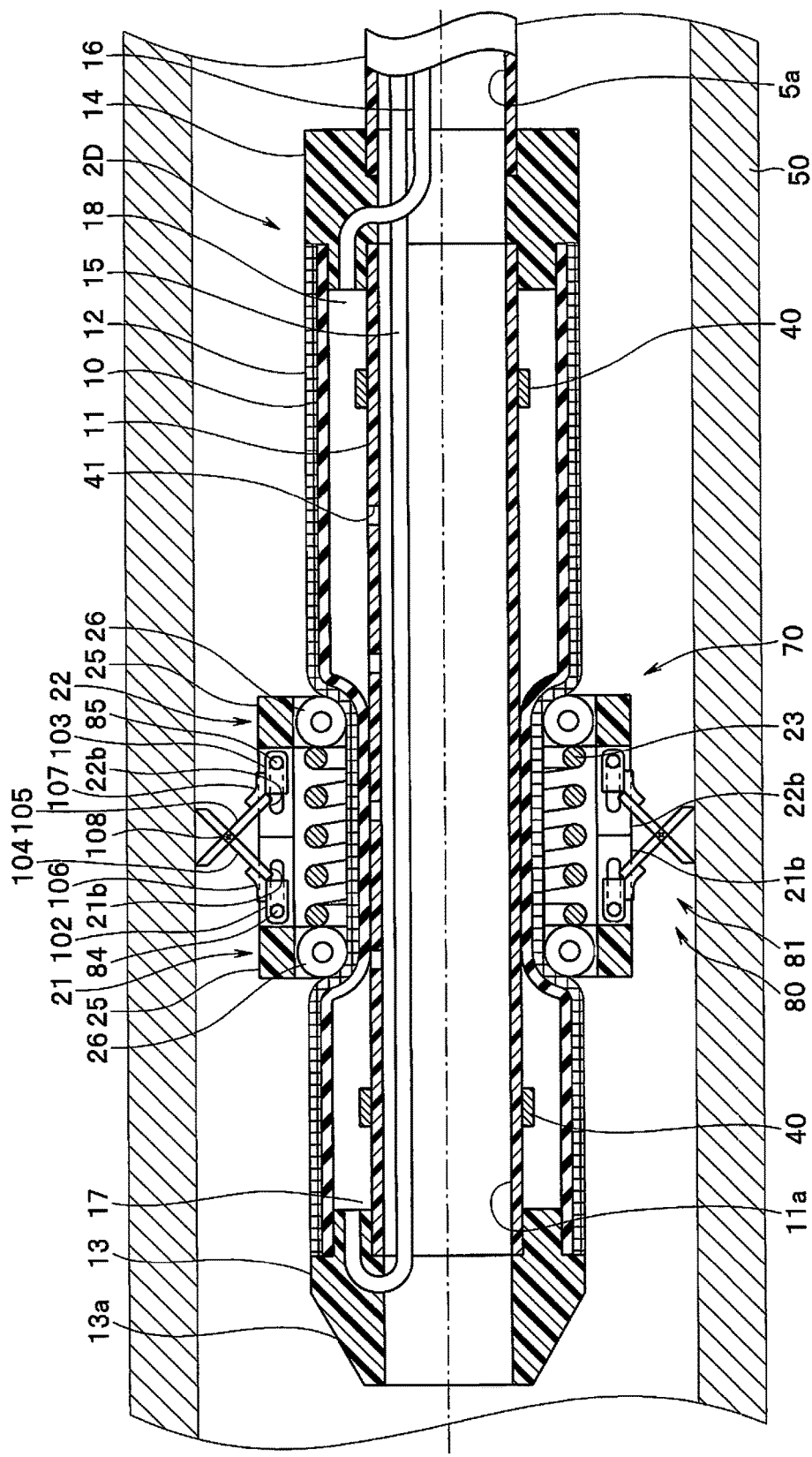
FIG. 38 relates to the second modification and is a main part sectional view schematically showing the driving unit at the time when the brake is in the actuated state in the pipe.

For example, in a modification shown in FIGS. 37 and 38, a first moving body 102 capable of moving forward and backward along the guide groove 21b is provided between the respective protrusions for guide 21a provided in the first slider 21. A second moving body 103 capable of moving forward and backward along the guide groove 22b is provided between the respective protrusions for guide 22a provided in the second slider 22.

A locking claw section 104 functioning as a contact member is coupled to a proximal end side of the first moving body 102 via an elastic body 106. A locking claw section 105 functioning as a contact member is coupled to a distal end side of the second moving body 103 via an elastic body 107.

Further, halfway parts of the respective locking claw sections 104 and 105 provided in the first and second moving bodies 102 and 103 opposed to each other are coupled via a shaft section 108.

In the configuration explained above, it is possible to achieve action and effects substantially the same as the action and effects in the embodiments explained above.

Figure 39:
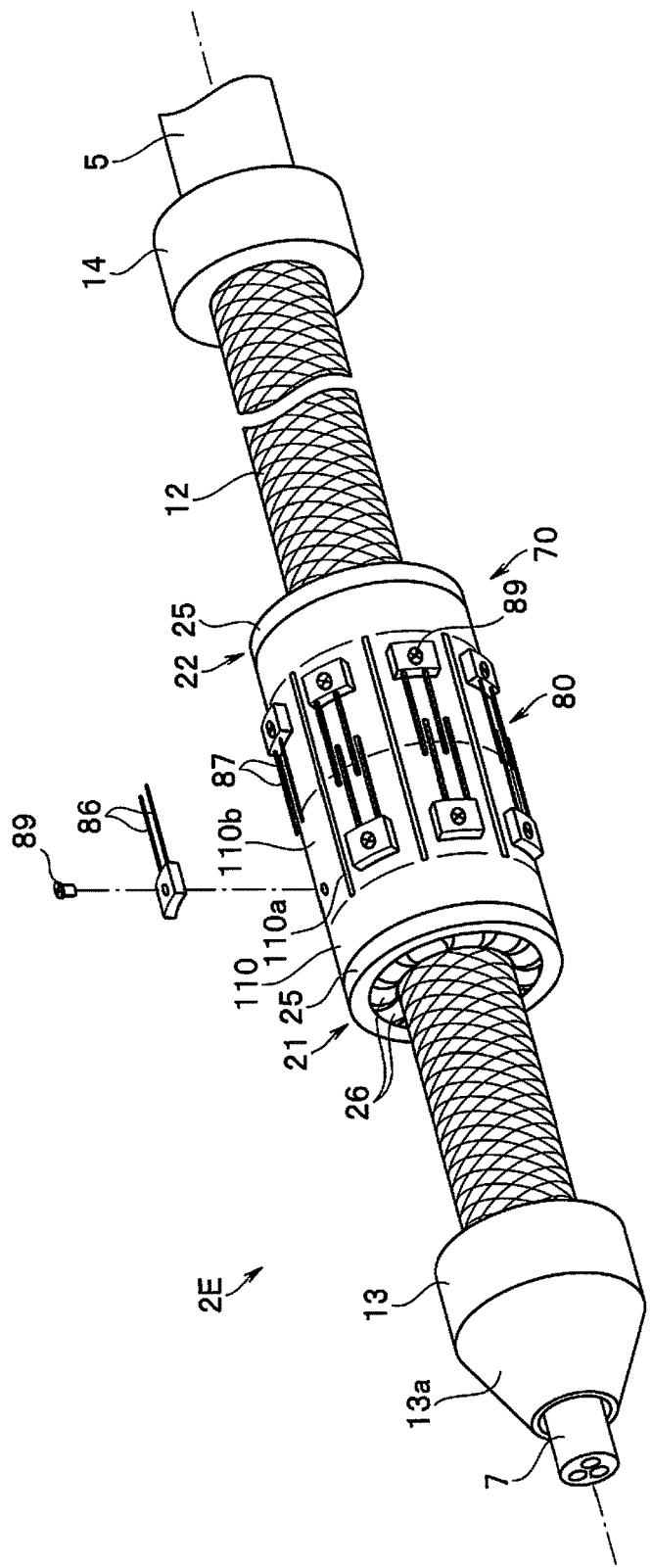
FIG. 39 relates to a sixth embodiment of the present invention and is a perspective view of a driving unit.
Figure 40:
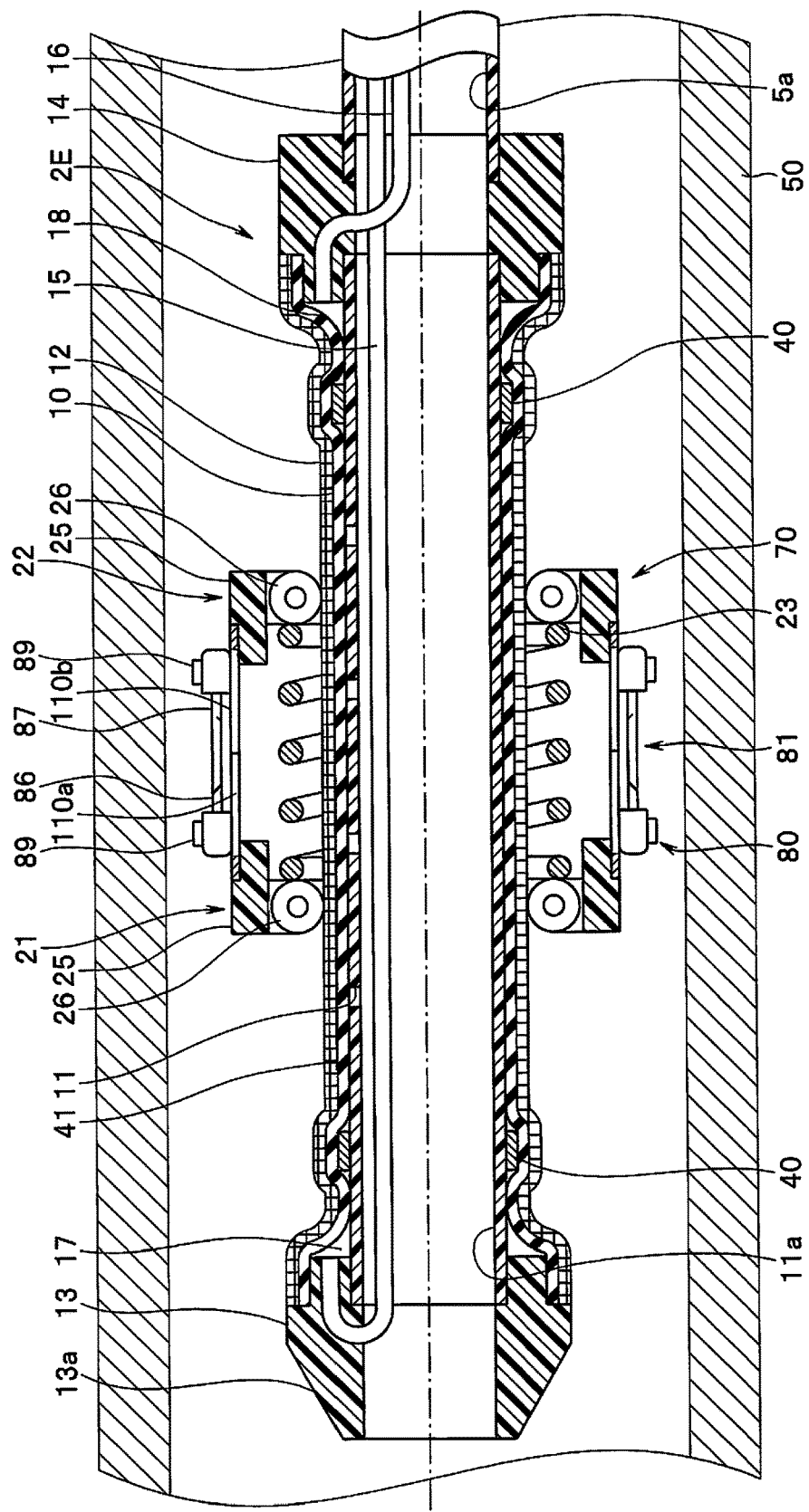
FIG. 40 relates to the sixth embodiment and is a main part sectional view schematically showing the driving unit at a time when a brake is in an unactuated state in a pipe.
Figure 41:
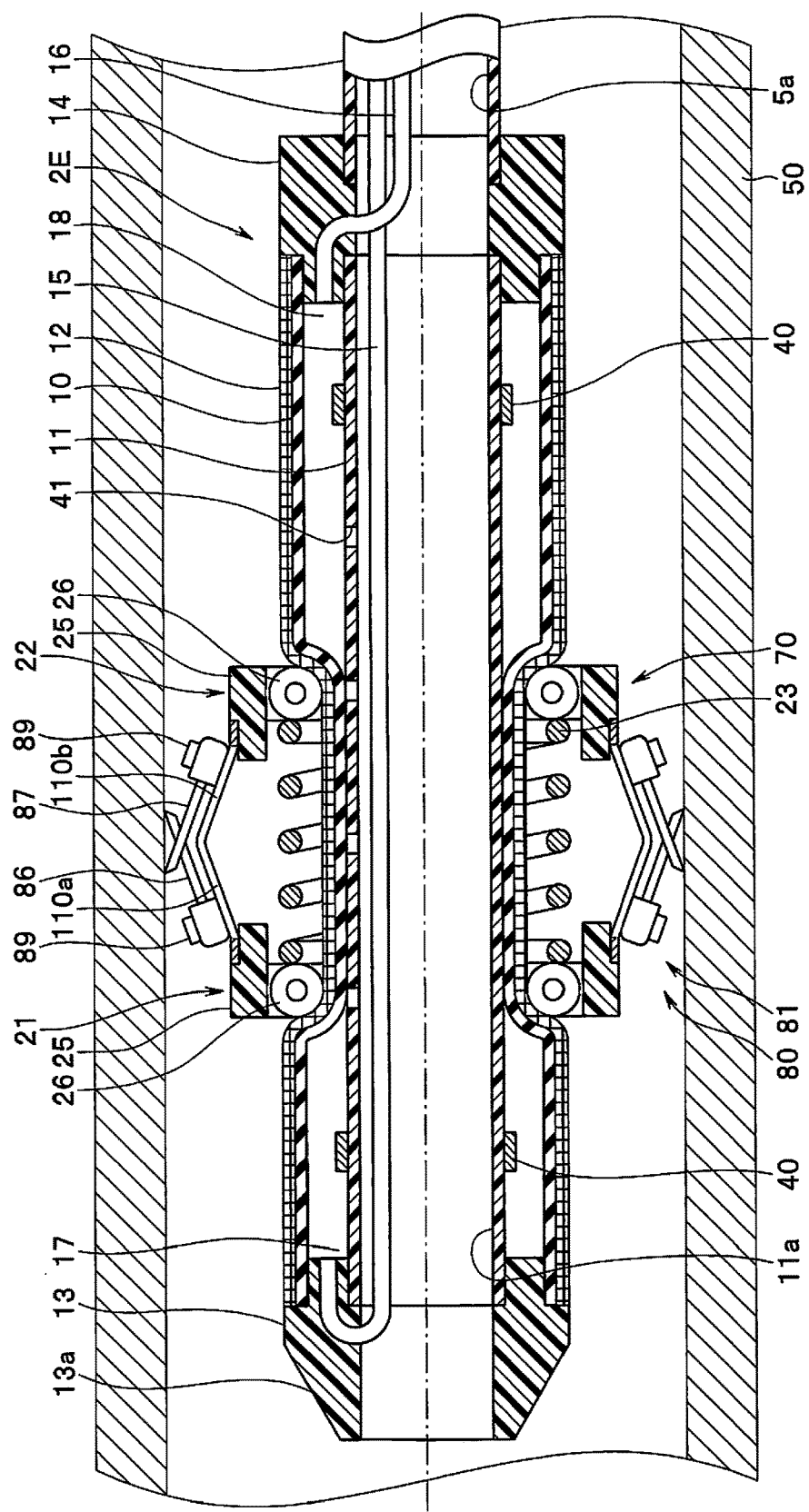
FIG. 41 relates to the sixth embodiment and is a main part sectional view schematically showing the driving unit at a time when the brake is in an actuated state in the pipe.

FIG. 39 to FIG. 41 relate to a sixth embodiment of the present invention. FIG. 39 is a perspective view of a driving unit. FIG. 40 is a main part sectional view schematically showing the driving unit at a time when a brake is in an unactuated state in a pipe. FIG. 41 is a main part sectional view schematically showing the driving unit at a time when the brake is in an actuated state in the pipe. Note that the present embodiment is mainly different from the fourth embodiment in a supporting structure for first and second swinging bodies. Otherwise, components substantially the same as the components in the fourth embodiment are denoted by the same reference numerals and signs and explanation of the components is omitted.

As shown in FIG. 39 to FIG. 41, a brake 80 configuring a driving unit 2E of the present embodiment includes a cylinder member 110 suspended between the first and second sliders 21 and 22.

A plurality of slits 110a extending in the axial direction of the first and second sliders 21 and 22 are provided at each predetermined interval halfway in the cylinder member 110. Tabular sections 110b formed among the slits 110a are capable of bending in a diameter expansion direction.

That is, in the cylinder member 110 of the present embodiment, distal ends and proximal ends of the respective tabular sections 110b are capable of bending in a valley fold direction when viewed from an outer circumference side of the cylinder member 110. Centers of the respective tabular sections 110b are capable of bending in a mountain fold direction.

Consequently, when the first and second sliders 21 and 22 are urged in a direction in which the first and second sliders 21 and 22 approach each other, it is possible to bend and deform (see FIG. 41) the respective tabular sections 110b formed in the cylinder member 110 in the diameter expansion direction from a flat state (see FIG. 38).

The locking claw sections 86 and 87 are detachably fixed to the respective tabular sections 110b in target positions based on centers of the respective tabular sections 110b using the screws 89.

According to the embodiment explained above, it is possible to achieve action and effects substantially the same as the action and effects in the fourth embodiment.

Figure 42:
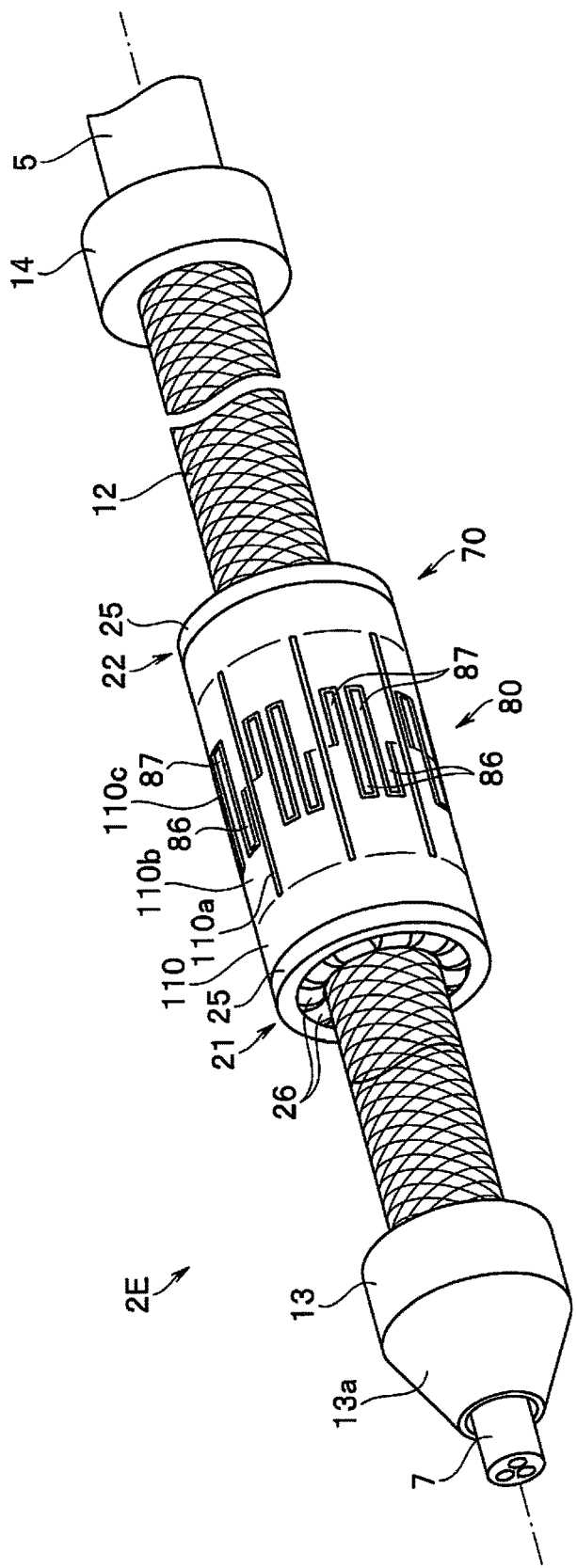
FIG. 42 relates to a first modification of the sixth embodiment and is a perspective view showing a cylinder member in which a brake is integrally formed.

It is also possible to adopt a configuration in which the first and second locking claw sections 86 and 87 of the brake 80 are integrally formed in the cylinder member 110 by only slits 110c. That is, a structure may be adopted in which, for example, as shown in FIG. 42, slits in the longitudinal direction are provided in a plurality of places and the slits 110c having a comb-tooth shape are inserted among the slits. With the configuration explained above, when the cylinder member 110 is pushed in from both sides, mountain-folded portions are bent and expanded in diameter. The first and second locking claw sections 86 and 87 formed by the comb-tooth shaped slits 110c expand in the radial direction and can be brought into contact with the pipe.

Figure 43:
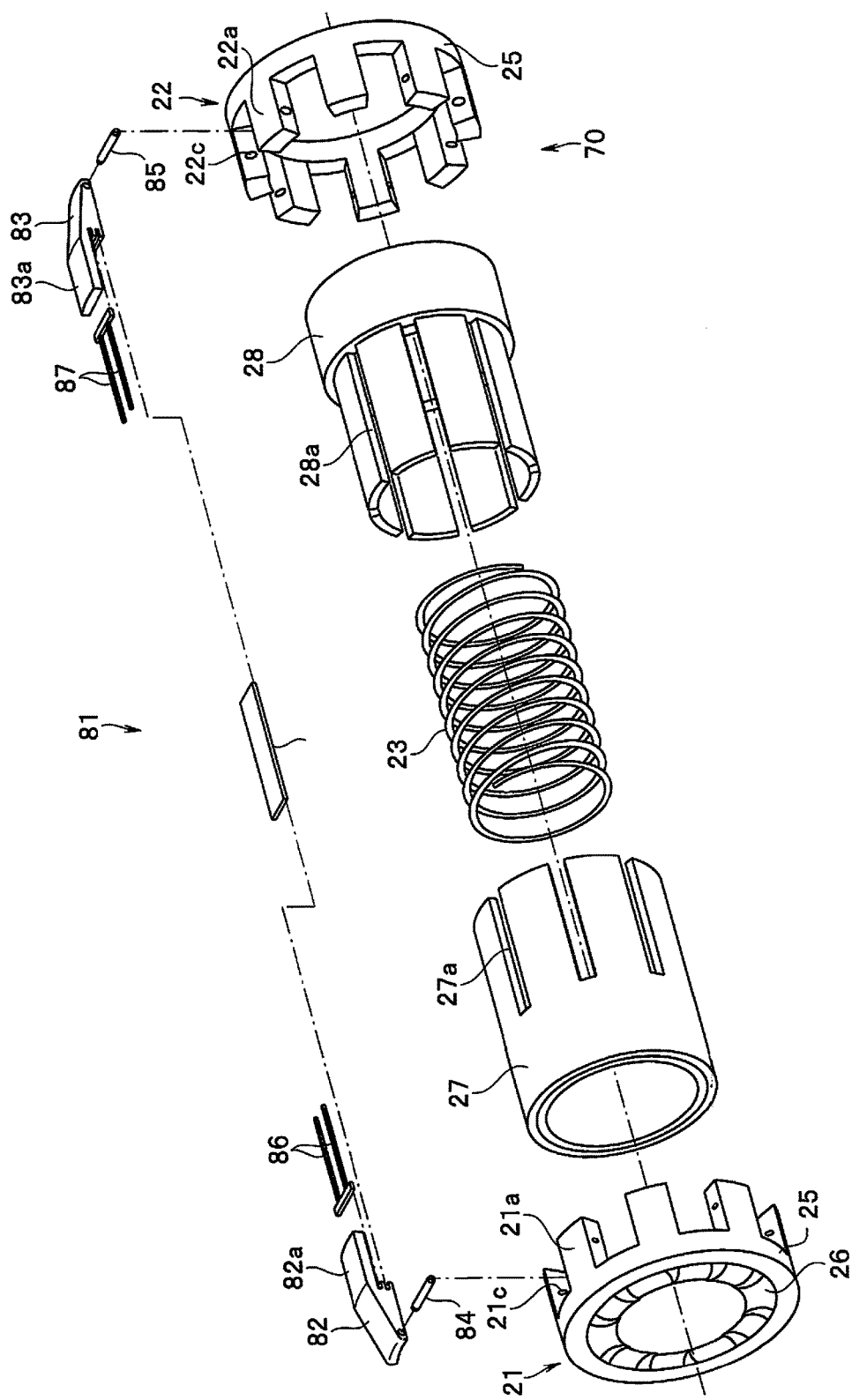
FIG. 43 relates to a seventh embodiment of the present invention and is an exploded perspective view showing main parts of a slider unit and a brake.
Figure 44:
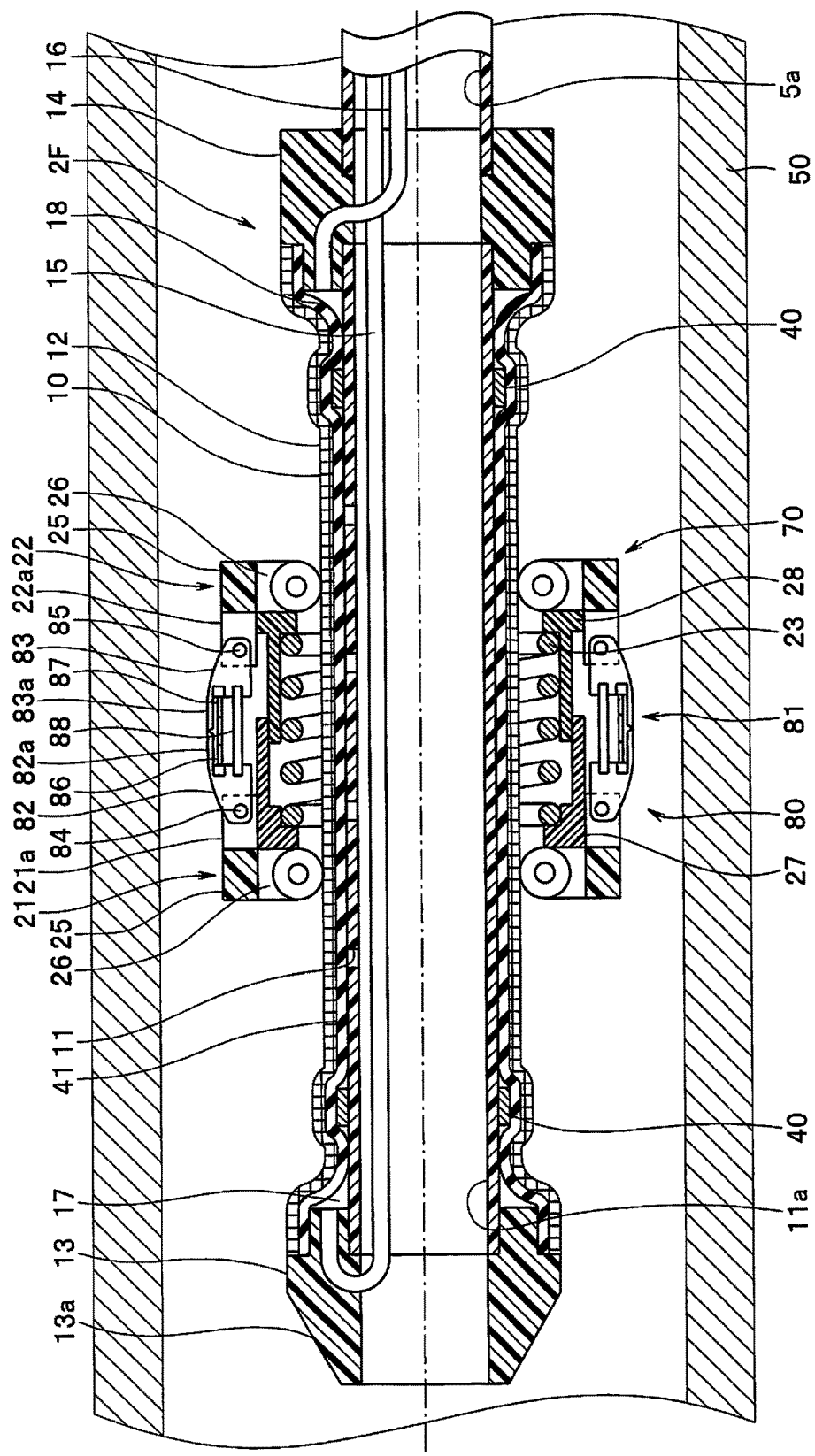
FIG. 44 relates to the seventh embodiment and is a main part sectional view schematically showing a driving unit at a time when the brake is in an unactuated state in a pipe.
Figure 45:
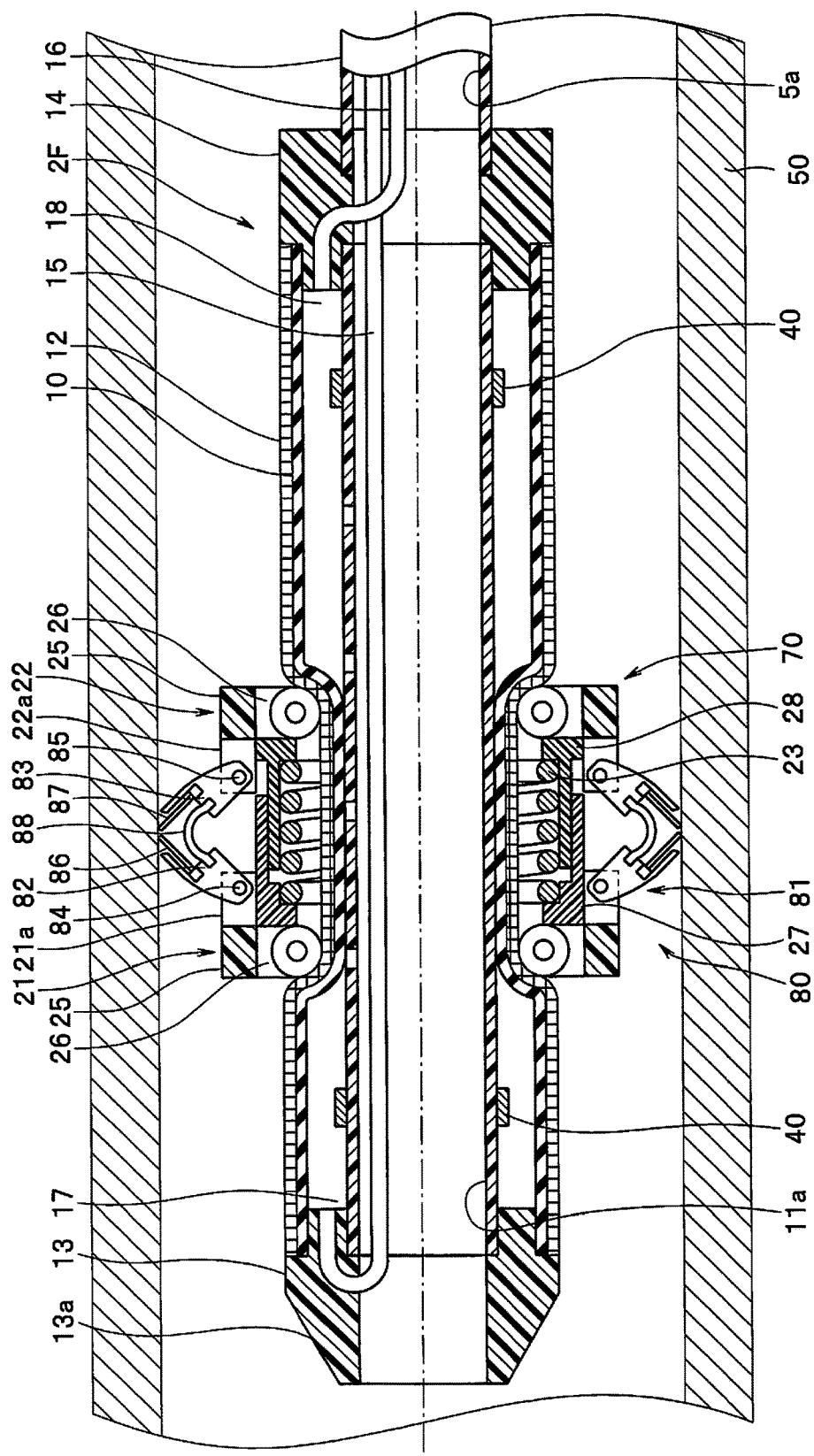
FIG. 45 relates to the seventh embodiment and is a main part sectional view schematically showing the driving unit at a time when the brake is in an actuated state in the pipe.

FIG. 43 to FIG. 45 relate to a seventh embodiment of the present invention. FIG. 43 is an exploded perspective view showing main parts of a slider unit and a brake. FIG. 44 is a main part sectional view schematically showing a driving unit at a time when the brake is in an unactuated state in a pipe. FIG. 45 is a main part sectional view schematically showing the driving unit at a time when the brake is in an actuated state in the pipe. Note that the present embodiment is mainly different from the fourth embodiment in a configuration of the slider unit 70. Otherwise, components same as the components in the fourth embodiment are denoted by the same reference numerals and signs as appropriate and explanation of the components is omitted.

As shown in FIG. 43 to FIG. 45, the slider unit 70 configuring a driving unit 2F of the present embodiment includes the first slider 21 attached to the outer circumference side of the elastic tube 10 via the mesh tube 12, the second slider 22 attached to the outer circumference side of the elastic tube 10 via the mesh tube 12 further on the proximal end side than the first slider 21, the coil spring 23 functioning as the urging member configured to urge the first and second sliders 21 and 22 in separating directions, and first and second inner cylinder members 27 and 28 disposed on the outer circumference side of the coil spring 23.

In the first slider 21, a plurality of protrusions for guide 21a extending to a proximal end side (the second slider 22 side) along an axial direction of the first slider 21 are provided. The protrusions for guide 21a are annularly arrayed each predetermined interval apart from one another on the outer circumference side of the coil spring 23 (see FIG. 43). Bearing holes 21c are respectively provided in both side portions of the respective protrusions for guide 21a.

In the second slider 22, a plurality of protrusions for guide 22a extending to a distal end side (the first slider 21 side) along an axial direction of the second slider 22 are provided. The protrusions for guide 22a are annularly arrayed each predetermined interval apart from one another on the outer circumference side of the coil spring 23 to be respectively opposed to the protrusions for guide 21a of the first slider 21 (see FIG. 43). Bearing holes 22c are respectively provided in both side portions of the respective protrusions for guide 22a.

The shaft sections 84 and 85 provided in the first and second swinging bodies 82 and 83 are engaged in the bearing holes 21c and 22c.

The first inner cylinder member 27 is configured by a member formed in a substantially cylindrical shape. The protrusions for guide 21a of the first slider 21 are externally fit in a distal end side of the first inner cylinder member 27. A plurality of slits 27a extending in the axial direction are provided at each equal interval on a proximal end side of the first inner cylinder member 27.

The second inner cylinder member 28 is configured by a member formed in a substantially cylindrical shape. The protrusions for guide 22a of the second slider 22 are externally fit in a proximal end side of the second inner cylinder member 28. A plurality of slits 28a extending in the axial direction are provided at each equal interval on a distal end side of the second inner cylinder member 28. Further, the distal end side of the second inner cylinder member 28 is fit in the proximal end side of the first inner cylinder member 27 to be capable of relatively moving in the axial direction.

According to the embodiment explained above, it is possible to achieve action and effects substantially the same as the action and effects in the fourth embodiment.

Figure 46:
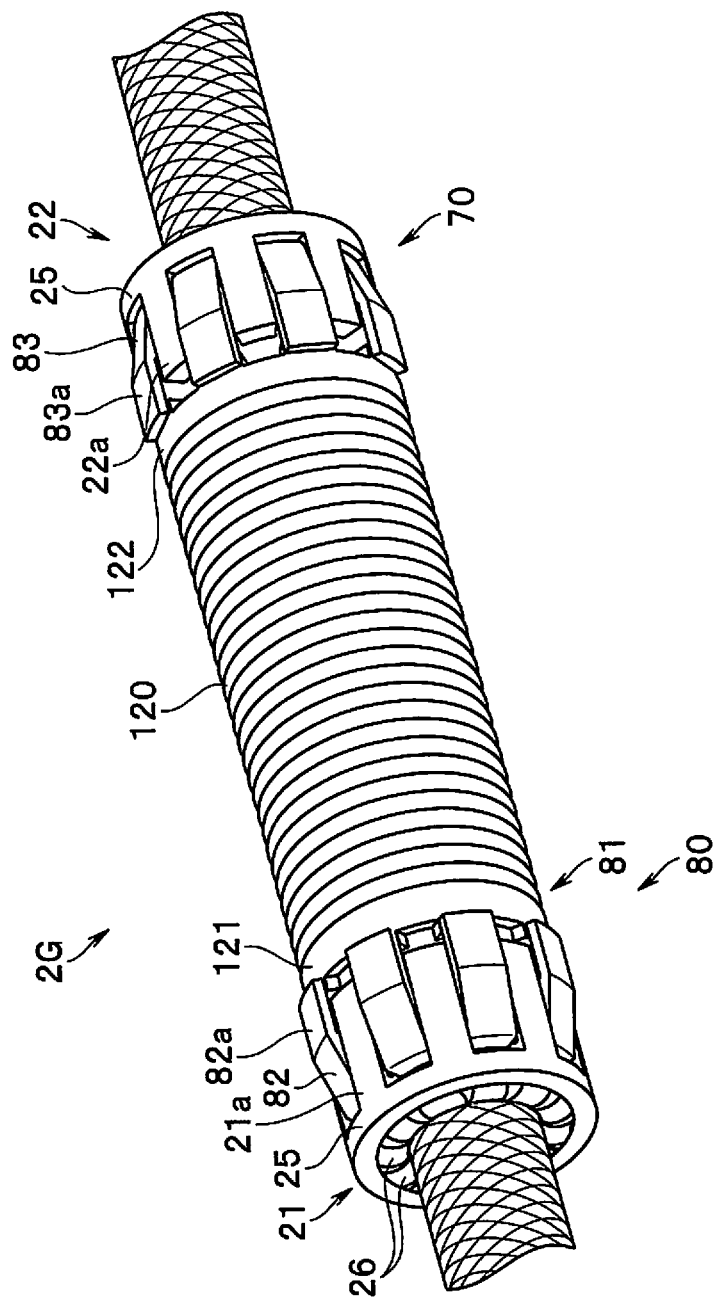
FIG. 46 relates to an eighth embodiment of the present invention and is a perspective view of a driving unit.
Figure 47:
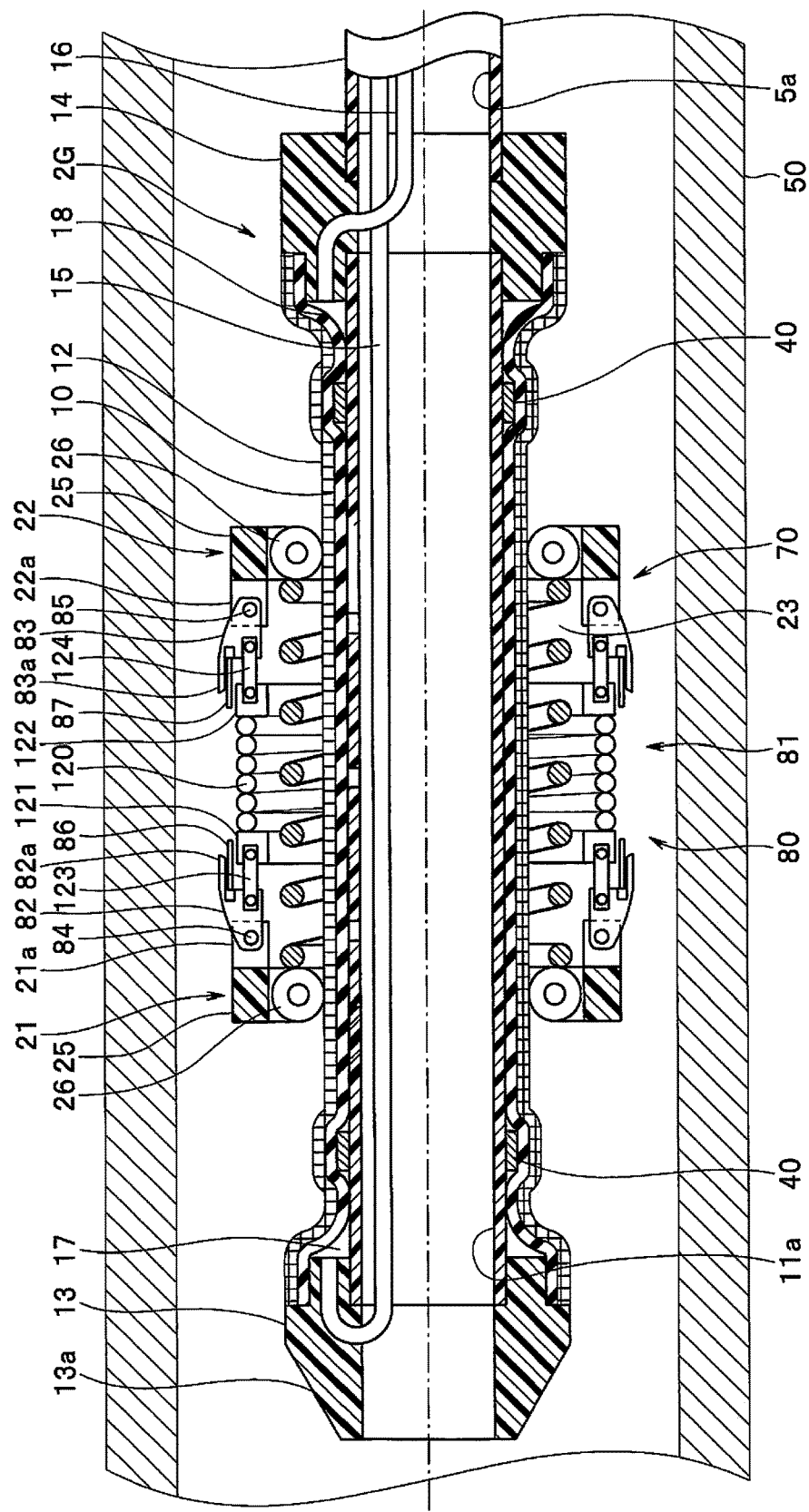
FIG. 47 relates to the eighth embodiment and is a main part sectional view schematically showing the driving unit at a time when a brake is in an unactuated state in a pipe.
Figure 48:
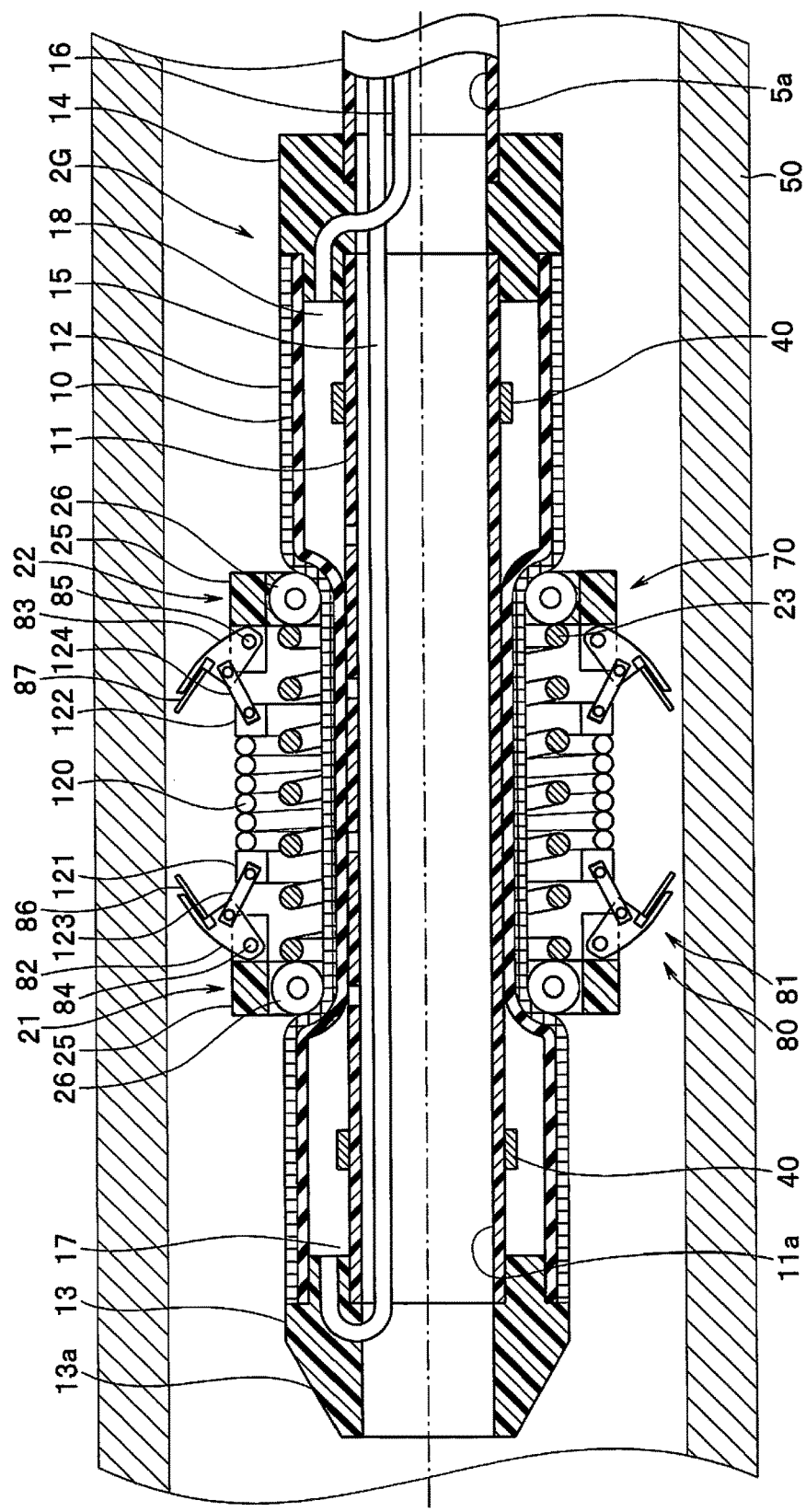
FIG. 48 relates to the eighth embodiment and is a main part sectional view schematically showing the driving unit at a time when the brake is in an actuated state in the pipe.

FIG. 46 to FIG. 48 relate to an eighth embodiment of the present invention. FIG. 46 is a perspective view of a driving unit. FIG. 47 is a main part sectional view schematically showing the driving unit at a time when a brake is in an unactuated state in a pipe. FIG. 48 is a main part sectional view schematically showing the driving unit at a time when the brake is in an actuated state in the pipe. Note that the present embodiment is mainly different from the fourth embodiment in that a coil member 120 is interposed between the first swinging body 82 and the second swinging body 83. Otherwise, components same as the components in the seventh embodiment are denoted by the same reference numerals and signs as appropriate and explanation of the components is omitted.

As shown in FIG. 46 to FIG. 48, the slider unit 70 configuring a driving unit 2G of the present embodiment includes the first slider 21 attached to the outer circumference side of the elastic tube 10 via the mesh tube 12, the second slider 22 attached to the outer circumference side of the elastic tube 10 via the mesh tube 12 further on the proximal end side than the first slider 21, and the coil spring 23 functioning as the urging member configured to urge the first and second sliders 21 and 22 in separating directions.

In the first slider 21, the plurality of protrusions for guide 21a extending to the proximal end side (the second slider 22 side) along the axial direction of the first slider 21 are provided. The protrusions for guide 21a are annularly arrayed each predetermined interval apart from one another on the outer circumference side of the coil spring 23 (see FIG. 44). Bearing holes are respectively provided in both side portions of the respective protrusions for guide 21a (not shown in the figure).

In the second slider 22, the plurality of protrusions for guide 22a extending to the distal end side (the first slider 21 side) along the axial direction of the second slider 22 are provided. The protrusions for guide 22a are annularly arrayed each predetermined interval apart from one another on the outer circumference side of the coil spring 23 to be respectively opposed to the protrusions for guide 21a of the first slider 21 (see FIG. 44). Bearing holes are respectively provided in both side portions of the respective protrusions for guide 22a (not shown in the figure).

A plurality of brake members 81 configuring the brake 80 are provided between the first and second sliders 21 and 22 of the slider unit 70.

The respective brake members 81 of the present embodiment include the first swinging bodies 82 supported by the first slider 21 and the second swinging bodies 83 supported by the second slider 22.

The first swinging body 82 is disposed between the protrusions for guide 21a, 21a adjacent to each other in the first slider 21. The shaft section 84 is provided on the distal end side (the fixed end side) of the first swinging body 82. Both the ends of the shaft section 84 are respectively engaged in bearing holes provided in the protrusions for guide 21a, 21a. Consequently, the first swinging body 82 is supported between the protrusions for guide 21a, 21a to be capable of swinging in the diameter expansion direction of the first slider 21.

The locking claw section 86 is provided on the proximal end side (the free end side) of the first swinging body 82. The locking claw section 86 is capable of swinging integrally with the first swinging body 82. When the first swinging body 82 is displaced in the diameter expansion direction by swinging, the locking claw section 86 is capable of coming into sliding contact with an inner circumferential surface of a pipe or the like. Note that the claw cover 82a for covering a part of the locking claw section 86 is integrally formed in the first swinging body 82.

The second swinging body 83 is disposed between the protrusions for guide 22a, 22a adjacent to each other in the second slider 22. The shaft section 85 is provided on the proximal end side (the fixed end side) of the second swinging body 83. Both the ends of the shaft section 85 are respectively engaged in bearing holes provided in the protrusions for guide 22a, 22a. Consequently, the second swinging body 83 is supported between the protrusions for guide 22a, 22a in the position opposed to the first swinging body 82 to be capable of swinging in the diameter expansion direction of the second slider 22.

The locking claw section 87 is provided on the distal end side (the free end side) of the second swinging body 83. The locking claw section 87 is capable of swinging integrally with the second swinging body 83. When the second swinging body 83 is displaced in the diameter expansion direction by swinging, the locking claw section 87 is capable of coming into sliding contact with an inner circumferential surface of a pipe or the like. Note that the claw cover 83a for covering a part of the locking claw section 87 is integrally formed in the second swinging body 83.

Further, the coil member 120 is interposed between first and second swinging bodies 82 and 83.

A first ring member 121 opposed to end faces of the respective protrusions for guide 21a provided in the first slider 21 is provided on a distal end side of the coil member 120. The first ring member 121 is coupled to the proximal end side of the first swinging body 82 respectively via link arms 123.

A second ring member 122 opposed to end faces of the respective protrusions for guide 22a provided in the second slider 22 is provided on a proximal end side of the coil member 120. The second ring member 122 is coupled to the distal end side of the second swinging body 83 respectively via link arms 124.

According to the embodiment explained above, in addition to the action and effects obtained in the fourth embodiment, since the first and second swinging bodies 83 and 84 are separated via the coil member 120, it is possible to set a maximum rigid length on the brake 80 short. It is possible to improve insertability into a bent pipe or the like as well.

Note that the present invention is not limited to the respective embodiments explained above. Various modifications and changes are possible. The modifications and the changes are within the technical scope of the present invention.

For example, in the respective embodiments, the example is explained in which the air is adopted as the fluid for actuating the driving unit. However, the present invention is not limited to this. The fluid can be changed as appropriate as long as the fluid can give internal pressure to an elastic tube. It is also possible to use various kinds of gas other than the air or liquid such as water or oil.

In the respective embodiments, the moving device for moving in a pipe provided in a building or the like is explained as an example. However, the present invention is not limited to this. It is also possible to apply the present invention to various moving devices for moving in a narrow space formed by wall sections having a narrow interval such as insides of pipes provided in various machines, a space between flanges of H steel, a space between rips of I steel or a channel steel, or an inside of debris.

In the respective embodiments, the example of the configuration in which the flexible tube is inserted through the inner circumference side of the elastic tube and the outer circumference side is covered with the mesh tube is explained. However, the flexible tube, the mesh tube, and the like can be omitted as appropriate according to an elasticity characteristic of the elastic tube, a use of the moving device, and the like.

In the respective embodiments, the example is explained in which the moving device is configured using the one or two driving units. However, the present invention is not limited to this. It is also possible to configure the moving device using three or more driving units.

In the respective embodiments, the series of procedures are executed according to the operation input by the user or the like. However, the present invention is not limited to this. For example, it is also possible to automatically perform the series of procedures in, for example, a computer for control.

It goes without saying that the configurations of the respective embodiments may be combined as appropriate.

What is claimed is:

1. A moving device comprising:
    an elastic tube, a sectional shape of which is elastically deformable according to an internal pressure given by fluid;
    a slider unit capable of moving forward and backward in a longitudinal direction of the elastic tube according to a change in the sectional shape of the elastic tube;
    a brake provided in the slider unit and configured to be deformed in a radial direction of the elastic tube to be capable of coming into sliding contact with a target object;
    a first fluid supply pipe configured to communicate with an inside on a distal end side of the elastic tube;
    a second fluid supply pipe configured to communicate with an inside on a proximal end side of the elastic tube; and
    a fluid adjusting section configured to supply the fluid to or discharge the fluid from the elastic tube respectively via the first fluid supply pipe and the second fluid supply pipe.

2. The moving device according to claim 1, wherein the slider unit includes:
    a first slider configured to partially restrict expansion of the elastic tube to form a first pressure chamber communicating with the first fluid supply pipe on the distal end side of the elastic tube and receive pressure from the first pressure chamber to be capable of moving on the elastic tube; and
    a second slider configured to partially restrict the expansion of the elastic tube to form a second pressure chamber communicating with the second fluid supply pipe on the proximal end side of the elastic tube and receive pressure from the second pressure chamber to be capable of moving on the elastic tube, and
    the brake includes a brake member configured to be displaced to project in the radial direction of the elastic tube when a relative interval between the first slider and the second slider is narrow and displaced to retract along a radial direction of the elastic tube when the relative interval between the first slider and the second slider is wide.

3. The moving device according to claim 2, further comprising a flexible tube inserted through the elastic tube, wherein
    the first slider brings an inner circumferential surface of the elastic tube into contact with an outer circumferential surface of the flexible tube to thereby form the first pressure chamber, and
    the second slider brings the inner circumferential surface of the elastic tube into contact with the outer circumferential surface of the flexible tube to thereby form the second pressure chamber.

4. The moving device according to claim 3, wherein the flexible tube includes leak holes for discharging the fluid in the elastic tube at a flow rate smaller than a flow rate of the fluid allowed by the first fluid supply pipe and the second fluid supply pipe.

5. The moving device according to claim 3, further comprising a stopper configured to restrict movement of the slider unit with respect to the elastic tube, wherein
    the stopper is disposed between the elastic tube and the flexible tube.

6. The moving device according to claim 2, wherein the brake member is a brake belt that bends to project in a diameter expansion direction of the elastic tube when the relative interval between the first slider and the second slider is narrowed and extends to retract along a radial direction of the elastic tube when the relative interval between the first slider and the second slider is widened.

7. The moving device according to claim 2, wherein the brake member includes a swinging body, a free end side of which is displaced to project in a diameter expansion direction of the elastic tube by swinging when the relative interval between the first slider and the second slider is narrowed and is displaced to retract along a radial direction of the elastic tube by the swinging when the relative interval between the first slider and the second slider is widened.

8. The moving device according to claim 7, wherein
    the slider unit includes a guide groove extending along the longitudinal direction of the elastic tube, and
    a fixed end side of the swinging body is supported via a shaft section movable along the guide groove.

9. The moving device according to claim 7, wherein the brake member includes a contact member projecting from the free end side of the swinging body.

10. The moving device according to claim 9, wherein
    the brake member includes a plurality of locking claw sections having different projecting lengths as the contact member, and
    among the plurality of locking claw sections, the locking claw section having a shorter projecting length is disposed further on an outer side in the diameter expansion direction on the free end side of the swinging body.

11. The moving device according to claim 2, wherein the brake member includes a contact member configured to be displaced to project in a diameter expansion direction of the elastic tube by a link mechanism when the relative interval between the first slider and the second slider is narrowed and displaced to retract along a radial direction of the elastic tube by the link mechanism when the relative interval between the first slider and the second slider is widened.

12. The moving device according to claim 11, wherein the contact member is a brake plate having rigidity.

13. The moving device according to claim 12, wherein a friction member is provided on a surface side of the brake plate.

14. The moving device according to claim 12, wherein the contact member is a locking claw section.

15. The moving device according to claim 1, further comprising a mesh tube interposed between the elastic tube and the slider unit and configured to limit elastic deformation of the elastic tube.

16. The moving device according to claim 2, wherein the slider unit includes an urging member configured to urge the first slider and the second slider in separating directions.

17. The moving device according to claim 16, wherein the urging member is a coil spring interposed on an outer circumference side of the elastic tube between the first slider and the second slider.

18. The moving device according to claim 1, further comprising a plurality of driving units respectively including the elastic tube, the slider unit, and the brake in plurality and provided to lie in a row in a front-rear direction, wherein
the first fluid supply pipe is disposed in plurality to respectively communicate with insides on distal end sides of the elastic tubes of the respective driving units,
the second fluid supply pipe is disposed in plurality to respectively communicate with insides on proximal end sides of the elastic tubes of the respective driving units, and
the fluid adjusting section individually supplies the fluid to or discharges the fluid from insides of the elastic tubes of the respective driving units respectively via the first fluid supply pipe and the second fluid supply pipe.

19. The moving device according to claim 18, further comprising:
a guide tube continuously provided on a proximal end side of the driving unit located at a most proximal end; and
an endoscope inserted through insides of the respective driving units and the guide tube.

20. The moving device according to claim 1, further comprising:
a guide tube continuously provided on a proximal end side of a driving unit including the elastic tube, the slider unit, and the brake; and
an endoscope inserted through insides of the driving unit and the guide tube.

21. The moving device according to claim 1, further comprising:
an insertion section continuously provided on a proximal end side of a driving unit including the elastic tube, the slider unit, and the brake; and
an observing section disposed on a distal end side of the driving unit.

22. A moving method of a moving device comprising:
a slider-unit moving procedure for controlling, unequally on a distal end side and a proximal end side of an elastic tube, a pressure of fluid supplied to or discharged from the elastic tube via at least either one of a first fluid supply pipe that communicates with an inside on the distal end side of the elastic tube, a sectional shape of which is elastically deformable according to an internal pressure, and a second fluid supply pipe that communicates with an inside on the proximal end side of the elastic tube and relatively moving, in a desired moving direction, a slider unit capable of moving forward and backward in a longitudinal direction of the elastic tube according to a change in the sectional shape of the elastic tube;
a brake actuating procedure for deforming a brake provided in the slider unit in a radial direction and bringing the brake into sliding contact with a target object;
an elastic-tube moving procedure for controlling, unequally on the distal end side and the proximal end side of the elastic tube, the pressure of the fluid supplied to or discharged from the elastic tube via at least either one of the first fluid supply pipe and the second fluid supply pipe and relatively moving the elastic tube in the moving direction with respect to the slider unit; and
a brake releasing procedure for releasing the sliding contact of the brake with the target object.

23. The moving method of the moving device according to claim 22, further comprising a retaining procedure for equally controlling, on the distal end side and the proximal end side of the elastic tube, the pressure of the fluid supplied to or discharged from the inside of the elastic tube via at least one of the first fluid supply pipe and the second fluid supply pipe by a fluid adjusting section halfway in the elastic-tube moving procedure and retaining a relative position of the elastic tube with respect to the slider unit.

24. The moving method of the moving device according to claim 22, wherein
the moving method includes, before the slider-unit moving procedure, an other-brake actuating procedure for other brakes provided continuously in a front-rear direction of the brake, and
the moving method includes, between the brake actuating procedure and the elastic-tube moving procedure, an other-brake releasing procedure for the other brakes, an other-slider moving procedure for moving other sliders in which the other brakes are provided, and the other-brake actuating procedure.

* * * * *